United States Patent
Pedersen et al.

(10) Patent No.: US 7,511,024 B2
(45) Date of Patent: Mar. 31, 2009

(54) FACTOR VII OR VIIA-LIKE MOLECULES

(75) Inventors: Anders Hjelholt Pedersen, Lyngby (DK); Kim Vilbour Andersen, Broenshoej (DK); Claus Bornaes, Hellerup (DK)

(73) Assignee: Bayer HealthCare LLC, Tarrytown, NY (US)

( * ) Notice: Subject to any disclaimer, the term of this patent is extended or adjusted under 35 U.S.C. 154(b) by 287 days.

(21) Appl. No.: 11/279,541

(22) Filed: Apr. 12, 2006

(65) Prior Publication Data

US 2007/0243588 A1    Oct. 18, 2007

Related U.S. Application Data

(62) Division of application No. 10/950,747, filed on Sep. 27, 2004, now Pat. No. 7,371,543, and a division of application No. 09/782,587, filed on Feb. 12, 2001, now Pat. No. 6,806,063.

(60) Provisional application No. 60/241,916, filed on Oct. 18, 2000, provisional application No. 60/184,036, filed on Feb. 22, 2000.

(30) Foreign Application Priority Data

Feb. 11, 2000    (DK) ............................... 2000 00218

(51) Int. Cl.
*C07H 21/04* (2006.01)
(52) U.S. Cl. ........................ 514/44; 536/23.1
(58) Field of Classification Search ........................ None
See application file for complete search history.

(56) References Cited

U.S. PATENT DOCUMENTS

| | | | |
|---|---|---|---|
| 4,784,950 A | 11/1988 | Hagen et al. | |
| 4,904,584 A | 2/1990 | Shaw | |
| 5,041,376 A | 8/1991 | Gething et al. | |
| 5,093,317 A | 3/1992 | Lewis et al. | |
| 5,180,583 A | 1/1993 | Hedner | |
| 5,225,537 A | 7/1993 | Foster | |
| 5,258,288 A | 11/1993 | Wydro et al. | |
| 5,288,629 A | 2/1994 | Berkner | |
| 5,460,950 A | 10/1995 | Barr et al. | |
| 5,504,064 A | 4/1996 | Morrisey et al. | |
| 5,516,640 A | 5/1996 | Watanabe et al. | |
| 5,580,560 A | 12/1996 | Nicolaisen et al. | |
| 5,648,254 A | 7/1997 | Mulvihill et al. | |
| 5,788,965 A | 8/1998 | Berkner et al. | |
| 5,817,788 A | 10/1998 | Berkner et al. | |
| 5,824,634 A | 10/1998 | Merchant | |
| 5,824,639 A | 10/1998 | Berkner | |
| 5,833,982 A | 11/1998 | Berkner et al. | |
| 5,837,843 A | 11/1998 | Smirnov et al. | |
| 5,847,085 A | 12/1998 | Esmon et al. | |
| 5,861,374 A | 1/1999 | Berkner | 514/8 |
| 5,891,843 A | 4/1999 | Turecek et al. | |
| 5,965,425 A | 10/1999 | Barr et al. | |
| 5,986,079 A | 11/1999 | Barr et al. | |
| 6,013,620 A | 1/2000 | Turecek et al. | |
| 6,017,882 A | 1/2000 | Nelsestuen | |
| 6,100,061 A | 8/2000 | Reiter et al. | |
| 6,423,826 B1 | 7/2002 | Nelsestuen et al. | |
| 6,475,725 B1 | 11/2002 | Reiter et al. | |
| 6,693,075 B1 | 2/2004 | Nelsestuen | |
| 6,747,003 B1 | 6/2004 | Nelsestuen | |
| 6,762,286 B2 | 7/2004 | Nelsestuen | |
| 6,806,063 B2 | 10/2004 | Pedersen et al. | |
| 6,903,069 B2 | 6/2005 | Pingel et al. | |
| 7,026,524 B2 | 4/2006 | Persson et al. | |
| 7,220,837 B1 | 5/2007 | Nelsestuen | |
| 2003/0100506 A1 | 5/2003 | Nelsestuen | |
| 2003/0100740 A1 | 5/2003 | Persson et al. | |
| 2003/0104978 A1 | 6/2003 | Persson et al. | |
| 2003/0211094 A1 | 11/2003 | Nelsestuen | |
| 2003/0211460 A1 | 11/2003 | Nelsestuen | |
| 2005/0164932 A1 | 7/2005 | Haaning | |
| 2006/0019336 A1 | 1/2006 | Pedersen | |
| 2006/0111282 A1 | 5/2006 | Haaning | |
| 2006/0166874 A1 | 7/2006 | Haaning | |
| 2006/0228782 A1 | 10/2006 | Pedersen | |
| 2006/0240524 A1 | 10/2006 | Pedersen | |
| 2006/0240525 A1 | 10/2006 | Pedersen | |

(Continued)

FOREIGN PATENT DOCUMENTS

EP    0 296 413 A2    12/1988

(Continued)

OTHER PUBLICATIONS

Cheung, W.F. et al., "Localization of a metal-dependent epitope to the amino terminal residues 33-40 of human factor IX", *Thrombosis Research*, 80(5):419-427 (1995).

(Continued)

*Primary Examiner*—Christopher R. Tate
*Assistant Examiner*—Roy Teller
(74) *Attorney, Agent, or Firm*—Susan M. Pellegrino

(57) ABSTRACT

Conjugates of Factor VII (FVII) and Factor VIIa (FVIIA) are provided, as are methods for preparing them. Methods for producing novel polypeptides contributing to the production of such conjugates are provided. Methods of treatment by administering a FVII or FVIIa conjugate are provided.

10 Claims, No Drawings

U.S. PATENT DOCUMENTS

| | | |
|---|---|---|
| 2006/0240526 A1 | 10/2006 | Haaning |
| 2006/0241041 A1 | 10/2006 | Haaning |
| 2006/0252127 A1 | 11/2006 | Pedersen |
| 2006/0252128 A1 | 11/2006 | Haaning |
| 2006/0252689 A1 | 11/2006 | Pedersen |
| 2006/0252690 A1 | 11/2006 | Pedersen |
| 2006/0258585 A1 | 11/2006 | Pedersen |
| 2006/0270000 A1 | 11/2006 | Haaning |
| 2006/0270001 A1 | 11/2006 | Haaning |
| 2006/0270002 A1 | 11/2006 | Haaning |
| 2006/0276377 A1 | 12/2006 | Haaning |
| 2007/0054366 A1 | 3/2007 | Andersen |
| 2007/0117756 A1 | 5/2007 | Haaning |
| 2007/0142280 A1 | 6/2007 | Pedersen |

FOREIGN PATENT DOCUMENTS

| | | |
|---|---|---|
| EP | 0 354 504 A2 | 2/1990 |
| EP | 0 370 205 A2 | 5/1990 |
| EP | 0 512 011 B1 | 11/1992 |
| WO | WO 88/10295 | 12/1988 |
| WO | WO 91/11514 | 8/1991 |
| WO | WO 92/15686 | 9/1992 |
| WO | WO 94/27631 A1 | 12/1994 |
| WO | WO 96/00577 | 1/1996 |
| WO | WO 98/32466 | 7/1998 |
| WO | WO 98/35026 | 8/1998 |
| WO | WO 99/03498 | 1/1999 |
| WO | WO 99/03887 | 1/1999 |
| WO | WO 99/20767 | 4/1999 |
| WO | WO 99/66031 | 12/1999 |
| WO | WO 00/26230 | 5/2000 |
| WO | WO 00/26354 | 5/2000 |
| WO | WO 00/28065 | 5/2000 |
| WO | WO 00/54787 | 9/2000 |
| WO | WO 00/66753 | 11/2000 |
| WO | WO 01/83725 A1 | 11/2001 |
| WO | WO 02/02764 | 1/2002 |
| WO | WO 02/03075 | 1/2002 |
| WO | WO 02/22776 | 3/2002 |
| WO | WO 02/38162 | 5/2002 |
| WO | WO 03/093465 | 11/2003 |
| WO | WO 2004/029091 | 4/2004 |
| WO | WO 2004/083361 | 9/2004 |

OTHER PUBLICATIONS

Database EMBL, "Gallus gallus anticoagulant protein C precursor (PROC) mRNA, complete cds", Database Accession No. AF465270, Feb. 2, 2003.

Hedner, U. "NovoSeven as a universal haemostatic agent." *Blood Coagul. Fibrinolysis* 11 Suppl 1:S107-S111 (2000).

Higashi, S. et al. "Molecular mechanism of tissue factor-mediated acceleration of factor VIIa activity," *J. Biol. Chem.* 271(43):26569-74 (1996).

Iakhiaev, A. et al. "The role of catalytic cleft and exosite residues of factor VIIa for complex formation with tissue factor pathway inhibitor", *Thromb. Haemost.* 85(3):458-463 (2001).

Sorensen, B.B. et al. "Incorporation of an active site inhibitor in factor VIIa alters the affinity for tissue factor," *J. Biol. Chem.* 272(18):11863-11868 (1997).

Sridhara S. et al. "Activation of a recombinant human factor VII structural analogue alters its affinity of binding to tissue factor," *Am. J. Hematol.* 53(2):66-71 (1996).

Zhang E, et al. "Structure of extracellular tissue factor complexed with factor VIIa inhibited with a BPTI mutan". J. Mo.l Biol. 1999;285(5):2089-2104.

Database Uniprot "Coalgulation Factor VII (EC 3.4.21.21) (Serum prothrombin converstion accelerator)", Database Accession No. P22457 Aug. 1, 1991.

Bharadwaj, D., et al., "Factor VII Central—A Novel Mutation in the Catalytic Domain that Reduces Tissue Factor Binding, Impairs Activation by Factor XA, and Abolishes Amidolytic and Coagulant Activity," *J. Biological Chemistry* 271(48):30685-30691 (1996).

Bjoern, S., et al., "Human Plasma and Recombinant Factor VII—Characterization of O-Glycosylations at Serine Residues 52 and 60 and Effects of Site-Directed Mutagenesis of Serine 52 to Alanine," *J. Biological Chemistry* 266(17):11051-11057 (1991).

Chang, J-Y., et al., "Replacing the First Epidermal Growth Factor-like Domain of Factor IX with That of Factor VII Enhances Activity In Vitro and in Canine Hemophilia B," *J. Clin. Invest.* 100(4):886-892 (1997).

Chang, Y-J., et al., "Engineered Recombinant Factor VII $Q^{217}$ Variants with Altered Inhibitor Specificities," *Biochemistry* 38:10940-10948 (1999).

Kemball-Cook, G., et al., "Coagulation Factor VII $Gln^{100} \rightarrow Arg$—Amino Acid Substitution at the Epidermal Growth Factor 2-Protease Domain Interface Results in Severely Reduced Tissue Factor Binding and Procoagulant Function," *J. Biological Chemistry* 273(14):8516-8521 (1998).

Dickinson, C.D., et al., "Active Site Modification of Factor VIIa Affects Interactions of the Protease Domain with Tissue Factor," *J. Biological Chemistry* 272(32):19875-19879 (1997).

Dickinson, C.D., et al., "identification of surface residues mediating tissue factor binding and catalytic function of the serine protease factor VIIa," *Proc. Natl. Acad. Sci. USA* 93:14379-14384 (1996).

Huang, Q., et al., "Substrate Recognition by Tissue Factor-Factor VIIa—Evidence for Interaction of Residues $Lys^{165}$ and $Lys^{166}$ of Tissue Factor with the 4-Carboxyglutamate-Rich Domain of Factor X," *J. Biological Chemistry* 271(36):21752-21757 (1996).

Iino, M., et al., "Functional Consequences of Mutations in Ser-52 and Ser-60 in Human Blood Coagulation Factor VII," *Archives of Biochemistry and Biophysics* 352(2):182-192 (1998).

Jin, J., et al., "Factor VIIa's First Epidermal Growth Factor-like Domain's Role in Catalytic Activity," *Biochemistry* 38:1185-1192 (1999).

Kelly, C.R., et al., "$Ca^{2+}$ Binding to the First Epidermal Growth Factor Module of Coagulation Factor VIIa Is Important for Cofactor Interaction and Proteolytic Function," *J. Biological Chemistry* 272(28):17467-17472 (1997).

Leonard, B.J.N., et al., "Activation and Active Site Occupation Alter Conformation in the Region of the First Epidermal Growth Factor-like Domain of Human Factor VII," *J. Biological Chemistry* 275(45):34894-34900 (2000).

Persson, E., "Characterization of the interaction between the light chain of factor VIIa and tissue factor," *FEBS Letters* 413:359-363 (1997).

Persson, E., et al., "Site-directed mutagenesis but not γ-carboxylation of Glu-35 in factor VIIa affects the association with tissue factor," *FEBS Letters* 385:241-243 (1996).

Persson, E., et al., "$Ca^{2+}$ Binding to the First Epidermal Growth Factor-like Domain of Factor VIIa Increases Amidolytic Activity and Tissue Factor Affinity," *J. Biological Chemistry* 272(32):19919-19924 (1997).

Petersen, L.C., et al., "Binding of $Zn^{2+}$ to a $Ca^{2+}$ loop allosterically attenuates the activity of factor VIIa and reduces its affinity for tissue factor," *Protein Science* 9:859-866 (2000).

Petrovan, R.J., et al., "Role of Residue $Phe^{225}$ in the Cofactor-Mediated, Allosteric Regulation of the Serine Protease Coagulation Factor VIIa," *Biochemistry* 39:14457-14463 (2000).

Ruf, W., et al., "Importance of Factor VIIa Gla-Domain Residue Arg-36 for Recognition of the Macromolecular Substrate Factor X Gla-Domain," *Biochemistry* 38:1957-1966 (1999).

Shah, A.M., et al., "Manipulation of the membrane binding site of vitamin K-dependent proteins: Enhanced biological function of human factor VII," *Proc. Natl. Acad. Sci. USA* 95:4229-4234 (1998).

Shobe, J., et al., "Macromolecular Substrate Affinity for the Tissue Factor-Factor VIIa Complex is Independent of Scissile Bond Docking," *J. Biological Chemistry* 274(34):24171-24175 (1999).

Shobe, J., et al., "Regulation of the Catalytic Function of Coagulation Factor VIIa by a Conformational Linkage of Surface Residue Glu 154 to the Active Site," *Biochemistry* 38:2745-2751 (1999).

Pending claims of U.S. Appl. No. 10/031,005, Nelsestuen which is a national phase of WO 00/66753 which was cited on previously filed IDS/1449), WO 00/66753.

Arnlijots et al., "Prevention of experimental arterial thrombosis by topical administration of active site-inactivated factor VIIa," J. Vasc. Surg., 1997, 25(2):341-346.

Bauer, "Treatment of factor VII deficiency with recombinant factor VIIa," Haemostasis, 1996, 26 (Suppl. 1):155-158.

Broze et al., "Monoclonal anti-human factor VII antibodies. Detection in plasma of a second protein antigenically and genetically related to factor VII," J. Clin. Invest., 1985, 76:937-946.

Choudhri et al., "Targeted Inhibition of Intrinsic Coagulation Limits Cerebral Injury in Stroke without Increasing Intracerebral Hemorrhage," J. Exp. Med., 1999, 190:91-99.

Christiansen et al., "Hydrophobic Amino Acid Residues of Human Anticoagulation Protein C that Contribute to its Functional Binding to Phospholipid Vesicles," Biochemistry, 1995, 34:10376-10382.

Dackiw et al., "Prevention of endotoxin-induced mortality by antitissue factor immunization," Arch. Surg., 1996, 131:1273-1278.

Dahlback, "Inherited Thrombophilia: Resistance to Activated Protein C as a Pathogenic Factor of Venous Thromboemolism," Blood, 1995, 85:607-614.

Database EMBL, "Coagulation factor VII (EC 3.4.21.21)(Serum prothrombin conversion accelerator)," "Bovine Factor VII. Its purification and complete amino acid sequence," ID FA7_BOVIN, Aug. 1, 1991 (3 pages).

"Docking of Tissue Factor and Factor VIIa Initiates Blood Coagulation," at http://www.sdsc.edu.IOTW/week46.96/ (1996).

Esmon et al., "Isolation of a membrane-bound cofactor for thrombin-catalyzed activation of protein C," J. Biol. Chem., 1982, 257:859-864.

Evans, Jr. and Nelsestuen, "Importance of cis-Proline 22 in the Membrane-Binding Conformation of Bovine Prothrombin," Biochemistry, 1996, 35:8210-8215.

Evans and Nelsestuen, "Importance of Cis-Proline 22 and the Aromatic Stack (Residues 41-45) for Prothrombin-Membrane Binding," Protein Sci., 1996, 5(Suppl. 1):163, Abstract #606-S.

Felgner et al., "Lipofection: a highly efficient, lipid-mediated DNA-transfection procedure," Proc. Natl. Acad. Sci. USA, 1987, 84:7413-7417.

Fiore et al., "The biochemical basis for the apparent defect of soluble mutant tissue factor in enhancing the proteolytic activities of factor VIIa," J. Biol. Chem., 1994, 269:143-149.

Freedman et al., "Identification of the phospholipid binding site in the vitamin K-dependent blood coagulation protein factor IX," J. Biol. Chem., 1996, 271(27):16227-16236.

Furie and Furie, "The molecular basis of blood coagulation," Cell, 1988, 53:505-518.

Han et al., "Isolation of a protein Z-dependent plasma protease inhibitor," Proc. Natl. Acad. Sci. USA, 1998, 95:9250-9255.

He et al., "Expression and functional characterization of chimeras between human and bovine vitamin-K-dependent protein-S-defining modules important for the species specificity of the activated protein C cofactor activity," Eur. J. Biochem., 1995, 227:433-440.

Hedner et al., "Recombinant Activated Factor VII in the Treatment of Bleeding Episodes in Patients with Inherited and Acquired Bleeding Disorders," Transfus. Med. Rev., 1993, 7:78-83.

Hope et al., "Production of Large Unilamellar Vesicles by a Rapid Extrusion Procedure. Characterization of Size Distribution, Trapped Volume and Ability to Maintain a Membrane Potential," Biochem. Biophys. Acta, 1985, 812:55-65.

Hoskins et al., "Cloning and characterization of human liver cDNA encoding a protein S precursor," Proc. Natl. Acad. Sci. USA, 1987, 84:349-353.

Huang, "Studies on Phosphatidylcholine Vesicles. Formation and Physical Characteristics," Biochemistry, 1969, 8:344-352.

Humphries et al., "Chemical methods of protein synthesis and modification," Curr. Opin. Biotechnol., 1991, 2(4):539-543.

Leff, "Genetically Stripped-Down Factor VIII Corrects Bleeding Disorder in Hemophiliac Mice," BioWorld Today, 1997, 8(209):1,6.

Lu and Nelsestuen, "Dynamic Features of Prothrombin Interaction with Phospholipid Vesicles of Different Size and Composition: Implications for Protein—Membrane Contact," Biochemistry, 1996, 35:8193-8200.

Lu and Nelsestuen, "The prothrombinase reaction: "mechanism switching" between Michaelis-Menten and non-Michaelis-Menten behaviors," Biochemistry, 1996, 35:8201-8209.

Matsubara et al., "A receptor tyrosine kinase, Sky, and its ligand Gas 6 are expressed in gonads and support primordial germ cell growth or survival in culture," Dev. Biol., 1996, 180:499-510.

Mayer et al., "Prothrombin Association with Phospholipid Monolayers," Biochemistry, 1983 22(2):316-321.

McDonald et al., "Comparison of Naturally Occurring Vitamin K-dependent Proteins: Correlation of Amino Acid Sequences and Membrane Binding Properties Suggests a Membrane Contact Site," Biochemistry, 1997, 36:5120-5127.

McDonald et al., "Ionic Properties of Membrane Association by Vitamin K-Dependent Proteins: The Case for Univalency," Biochemistry, 1997, 36(50):15589-15598.

Morrissey et al., "Quantitation of Activated Factor VII Levels in Plasma Using a Tissue Factor Mutant Selectively Deficient in Promoting Factor VII Activation," Blood, 1993, 81(3):734-744.

Muir et al., "The chemical synthesis of proteins," Curr. Opin. Biotechnol., 1993, 4(4):420-427.

Nakagaki et al., "Initiation of the Extrinsic Pathway of Blood Coagulation: Evidence for the Tissue Factor Dependent Autoactivation of Human Coagulation Factor VII," Biochemistry, 1991, 30:10819-10824.

Nelsestuen et al., "Membrane association with multiple calcium ions: vitamin-K-dependent proteins, annexins and pentraxins," Current Opinion in Structural Biology 9:433-437 (1999).

Nelsestuen, "Enhancement of Vitamin-K-Dependent Protein Function by Modification of the gamma-Carboxyglutamic Acid Domain: Studies of Protein C and Factor VII," Trends Cardiovasc. Med. 9(6):162-167 (1999).

Nelsestuen et al., "Vitamin K-Dependent Proteins," in 58 Vitamins and Hormones: Advances in Research and Applications (Gerald Litwack ed., Academic Press, 2000), pp. 355-389.

Nelsestuen et al., "Elevated Function of Blood Clotting Factor VIIa Mutants That Have Enhanced Affinity for Membranes," J. Biol. Chem., 2001, 276(43):39825-39831.

Nelsestuen et al., "Equilibria Involved in Prothrombin- and Blood Clotting Factor X-Membrane Binding," Biochemistry, 1977, 16(19):4164-4171.

Nelsestuen and Suttie, "Properties of Asialo and Aglycoprothrombin," Biochem. Biophys. Res. Commun., 1971, 45:198-203.

Nicolaes et al., "A prothrombinase-based assay for detection of resistance to activated protein C," Thromb. Haemost., 1996, 76:404-410.

Nicolaisen et al., "Immunological aspects of recombinant factor VIIa (rFVIIa) in clinical use," Thromb. Haemost., 1996, 76:200-204.

Okafuji et al., EMBL Data Library, Accession No. S18994, Sep. 10, 1999 (protein C activated precursor, sequence) (Score Search).

Perera et al., "Trans-cis Isomerization of Proline 22 in Bovine Prothrombin Fragment 1: A Surprising Result of Structural Characterization," Biochemistry, 1998, 37:10920-10927.

Petersen et al., "Quenching of the amidolytic activity of one-chain tissue-type plasminogen activator by mutation of lysine-416," Biochemistry, 1990, 29:3451-3457.

Petrovan et al., "Residue Met$^{156}$ contributes to the labile enzyme conformation of coagulation factor VIIa," J. Biol. Chem. 2001, 276(9):6616-6620.

Ratcliffe et al., "The Importance of Specific γ-Carboxyglutamic Acid Residues in Prothrombin," J. Biol. Chem., 1993, 268(32):24339-24345.

Resnick and Nelsestuen, "Prothrombin-Membrane Interaction. Effects of Ionic Strength, pH, and Temperature," Biochemistry, 1980, 19(13):3028-3033.

Rezaie and Esmon, "The function of calcium in protein C activation by thrombin and the thrombin-thrombomodulin complex can be distinguished by mutational analysis of protein C derivatives," J. Biol. Chem., 1992, 267:26104-26109.

Sakai et al., "The γ-carboxyglutamic Acid Domain of Human Factor VIIA is Essential for Its Interaction with Cell Surface Tissue Factor," J. Biol. Chem., 1990, 265(4):1890-1894.

Schmidel et al., "Organization of the Human Protein S Genes," J. Biol. Chem., 1990, 29(34):7845-7852.

Schulman et al., "Feasibility of using recombinant factor VIIa in continuous infusion," Thromb. Haemost., 1996, 75(3):432-436.

Schwalbe et al., "Protein Structural Requirements and Properties of Membrane Binding by γ-Carboxyglutamic Acid-containing Plasma Proteins and Peptides," J. Biol. Chem., 1989, 264:20288-20296.

Seffernick et al., "Melamine Deaminase and Atrazine Chlorohydrolase: 98 Percent Identical but Functionally Different," J. Bacteriol. 183(8):2405-2410 (2001).

Seshadri et al., "Differences in the Metal Ion Structure between Sr- and Ca-Prothrombin Fragment 1," Biochemistry, 1994, 33:1087-1092.

Shen et al., "Enhancing the Activity of Protein C by Mutagenesis to Improve the Membrane-Biding Site: Studies Related to Proline 10," Biochemistry, 1997, 36(51):16025-16031.

Shen et al., "Enhancement of Human Protein C Function by Site-directed Mutagenesis of the γ-Carboxyglutamic Acid Domain," J. Biol. Chem., 1998, 273(47):31086-31091.

Smirnov et al., "A Chimeric Protein C Containing the Prothrombin Gla Domain Exhibits Increased Anticoagulant Activity and Altered Phospholipid Specificity," J. Biol. Chem., 1998, 273(15):9031-9040.

Thariath et al., "Highly conserved residue arginine-15 is required for the $Ca^{2+}$-dependent properties of the γ-carboxyglutamic acid domain of human anticoagulation Protein C and activated Protein C," Biochem. J., 1997, 322:309-315.

Thim et al., "Amino Acid Sequence and Posttranslational Modification of Human Factor VIIa from Plasma and Transfected Baby Hamster Kidney Cells," Biochemistry, 1988, 27:7785-7793.

Thomsen et al., "Pharmacokinetics of recombinant factor VIIa in the rat—a comparison of bio-, immuno- and isotope assays," Thromb. Haemost., 1993, 70(3):458-464.

Vallette et al., "Construction of mutant and chimeric genes using the polymerase chain reaction," Nucleic Acids Res., 1989, 17(2):723-733.

Vrana et al., "Expression of tissue factor in tumor stroma correlates with progression to invasive human breast cancer: paracrine regulation by carcinoma cell-derived members of the transforming growth factor beta family," Cancer Res., 56:5063-5070 (1996).

Weber et al., "Modifications of Bovine Prothrombin Fragment 1 in the Presence and Absence of Ca(II) Ions," J. Biol. Chem., 1992, 267(7):4564-4569.

Wei et al., "Kinetic and Mechanistic Analysis of Prothrombin-Membrane Binding by Stopped-Flow Light Scattering," Biochemistry, 1982, 21:1949-1959.

Wells, "Additivity of Mutational Effects in Proteins," Biochem. 29(17):8509-8517 (1990).

Welsch et al., "Chemical Modification of Prothrombin Fragment 1: Documentation of Sequential, Two-Stage Loss of Protein Function," Biochemistry, 1988, 27:4933-4938.

Welsch and Nelsestuen, "Amino-terminal alanine functions in a calcium-specific process essential for membrane binding by prothrombin fragment 1," Biochemistry, 1988, 27:4939-4945.

Yan et al., "Characterization and Novel Purification of Recombinant Human Protein C from Three Mammalian Cell Lines," Bio/Technology, 1990, 8:655-661.

Zhang et al., "Role of Individual γ-Caboxyglutamic Acid Residues of Activated Human Protein C in Defining its In Vitro Anticoagulant Activity," Blood, 1992, 80(4):942-952.

Zwaal et al., "Lipid-protein interactions in blood coagulation," Biochimica et Biophysica Acta, 1998, 1376:433-453.

Cheung, Wing-Fai et al., "Localization Of An E0pitope Of A Calcium-Dependent Monoclonal Antibody To The N-Terminal Region Of The GLA Domain Of Human Factor VII", Thrombois Research, (1995), 79(2): 199-206.

Dickinson, Craig D. et al., "Influence of Cofactor Binding and Active Site Occupancy on the Conformation of the Macromolecular Substrate Exosite Of Factor VIIa", J. Mol. Bio. (1998) 277:959-971.

Jin, Jianping et al., "Four Loops of the Catalytic Domain of Factor VIIa Mediate the Effect of the First EGF-like Domain Substitution on Factor VIIa Catalytic Activity", J. Mol. Bio. (2001) 307:1503-1517.

Neuenschwander, Pierre F. et al., "Alteration of the Substrate and Inhibitor Specificities of Blood Coagulation Factor VIIa: Importance of Amino Acid Residue K192", Biochemistry, (1995) 34:8701-8707.

J. Toomey et al., Localization of the Human Tissue Factor Recognition Determinant of Human Factor VIIa, J. Biol. Chem. 266(29):19198-19202 (1991).

Harvey, Stephen B., et al., "Mutagenesis of the γ-carboxyglutamic acid domain of human factor VII to generate maximum enhancement of the membrane contact site," The Journal of Biological Chemistry 278(10):8363-8369 (Mar. 2003).

Henderson, Nicole et al., "Response of factor VII and IX-deficient blood to wild type and high membrane affinity mutant factor VIIa in an in vitro whole blood clotting assay: possible correlation to clinical outcome," Thromb Haemost 88:98-103 (2002).

Stone, Matthew et al., "Unusual benefits of macromolecular shielding by polyethylene glycol for reactions at the diffusional limit: the case of factor VIIai and tissue factor," Biochemistry 41:15820-15825 (2002).

Zhang, Li et al., "The contributions of individual γ-carboxyglutamic acid residues in the calcium-dependent binding of recombinant human protein c to acidic phospholipid vesicles," The Journal of Biological Chemistry 268 (16):12040-12045 (Jun. 1993).

FACTOR VII OR VIIA-LIKE MOLECULES

CROSS-REFERENCES TO RELATED APPLICATIONS

The present application claims priority to and benefit of the following United States and international patent applications: Danish Patent Application Number PA 2000 00218, filed Feb. 11, 2000; U.S. Provisional Patent Application No. 60/184, 036, filed Feb. 22, 2000; and, U.S. Provisional Patent Application No. 60/241,916, filed Oct. 18, 2000.

COPYRIGHT NOTIFICATION

Pursuant to 37 C.F.R. 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The present invention relates to novel Factor VII (FVII) or Factor VIIa (FVIIa) polypeptide conjugates, to their preparation and use in therapy, in particular for the treatment of a variety of coagulation-related disorders.

BACKGROUND OF THE INVENTION

Blood coagulation is a process consisting of a complex interaction of various blood components (or factors) that eventually gives rise to a fibrin clot. Generally, the blood components participating in what has been referred to as the coagulation "cascade" are proenzymes or zymogens, i.e., enzymatically inactive proteins that are converted into an active form by the action of an activator. One of these coagulation factors is FVII.

FVII is a vitamin K-dependent plasma protein synthesized in the liver and secreted into the blood as a single-chain glycoprotein with a molecular weight of 53 kDa (Broze & Majerus, J. Biol. Chem 1980; 255:1242-1247). The FVII zymogen is converted into an activated form (FVIIa) by proteolytic cleavage at a single site, R152-I153, resulting in two chains linked by a single disulfide bridge. FVIIa in complex with tissue factor (FVIIa complex) is able to convert both factor IX and factor X into their activated forms, followed by reactions leading to rapid thrombin production and fibrin formation (Østerud & Rapaport, Proc Natl Acad Sci USA 1977; 74:5260-5264).

FVII undergoes post-translational modifications, including vitamin K-dependent carboxylation resulting in ten γ-carboxyglutamic acid residues in the N-terminal region of the molecule. Thus, residue number 6, 7, 14, 16, 19, 20, 25, 26, 29 and 35 shown in SEQ ID NO:1 are γ-carboxyglutamic acids residues in the Gla domain important for FVII activity. Other post-translational modifications include sugar moiety attachment at two naturally occurring N-glycosylation sites at position 145 and 322, respectively, and at two naturally occurring O-glycosylation sites at position 52 and 60, respectively.

The gene coding for human FVII (hFVII) has been mapped to chromosome 13 at q34-qter 9 (de Grouchy et al., Hum Genet 1984; 66:230-233). It contains nine exons and spans 12.8 Kb (O'Hara et al., Proc Natl Acad Sci USA 1987; 84:5158-5162). The gene organisation and protein structure of FVII are similar to those of other vitamin K-dependent procoagulant proteins, with exons 1a and 1b encoding for signal sequence; exon 2 the propeptide and Gla domain; exon 3 a short hydrophobic region; exons 4 and 5 the epidermal growth factor-like domains; and exon 6 through 8 the serine protease catalytic domain (Yoshitake et al., Biochemistry 1985; 24: 3736-3750).

Reports exist on experimental three-dimensional structures of hFVIIa (Pike et al., PNAS. U.S.A., 1999; 96:8925-30 and Kemball-Cook et al., J. Struct. Biol, 1999; 127:213-223), of hFVIIa in complex with soluble tissue factor using X-ray crystallographic methods (Banner et al., Nature, 1996; 380: 41 and Zhang et al., J. Mol. Biol, 1999; 285: 2089), and of smaller fragments of hFVII (Muranyi et al., Biochemistry, 1998; 37:10605 and Kao et al., Biochemistry, 1999; 38:7097).

Relatively few protein-engineered variants of FVII have been reported (Dickinson & Ruf, J Bio Chem, 1997; 272: 19875-19879, Kemball-Cook et al., J Biol Chem, 1998; 273: 8516-8521, Bharadwaj et al., J Biol Chem, 1996; 271:30685-30691, Ruf et al., Biochemistry, 1999; 38:1957-1966).

Reports exist on expression of FVII in BHK or other mammalian cells (WO92/15686, WO91/11514 and WO88/10295) and co-expression of FVII and kex2 endoprotease in eukaryotic cells (WO 00/28065).

Commercial preparations of human recombinant FVIIa are sold as NovoSeven®. NovoSeven® is indicated for the treatment of bleeding episodes in hemophilia A or B patients. NovoSeven® is the only rFVIIa for effective and reliable treatment of bleeding episodes available on the market.

An inactive form of FVII in which arginine 152 and/or isoleucine 153 is/are modified has been reported in WO91/1154. These amino acids are located at the activation site. WO 96/12800 describes inactivation of FVIIa by a serine proteinase inhibitor; inactivation by carbamylation of FVIIa at the α-amino acid group I153 has been described by Petersen et al., Eur J Biochem, 1999; 261:124-129. The inactivated form is capable of competing with wild-type FVII or FVIIa for binding to tissue factor and inhibiting clotting activity. The inactivated form of FVIIa is suggested to be used for treatment of patients being in hypercoagulable states, such as patients with sepsis, in risk of myocardial infarction or of thrombotic stroke.

A circulating rFVIIa half-life of 2.3 hours was reported in "Summary Basis for Approval for NovoSeven®," FDA reference number 96-0597. Relatively high doses and frequent administration are necessary to reach and sustain the desired therapeutic or prophylactic effect. As a consequence adequate dose regulation is difficult to obtain and the need of frequent intravenous administrations imposes restrictions on the patient's way of living.

Another problem in current rFVIIa treatment is the relative instability of the molecule with respect to proteolytic degradation. Proteolytic degradation is a major obstacle for obtaining a preparation in solution as opposed to a lyophilised product. The advantage of obtaining a stable soluble preparation lies in easier handling for the patient, and, in the case of emergencies, quicker action, which potentially can become life saving. Attempts to prevent proteolytic degradation by site directed mutagenesis at major proteolytic sites have been disclosed in WO88/10295.

A molecule with a longer circulation half-life would decrease the number of necessary administrations. Given the association of current FVIIa product with frequent injections, and the potential for obtaining more optimal therapeutic FVIIa levels with concomitant enhanced therapeutic effect, there is a clear need for improved FVII or FVIIa-like molecules.

One way to increase the circulation half-life of a protein is to ensure that renal clearance of the protein is reduced. This can be achieved by conjugating the protein to a chemical moiety, which is capable of conferring reduced renal clearance to the protein.

Furthermore, attachment of a chemical moiety to the protein or substitution of amino acids exposed to proteolysis can effectively block a proteolytic enzyme from contact leading to proteolytic degradation of the protein. Polyethylene glycol (PEG) is one such chemical moiety that has been used in the preparation of therapeutic protein products.

WO98/32466 suggests that FVII, among many other proteins, can be PEGylated but does not provide any further information in this respect.

SUMMARY OF THE INVENTION

This application discloses improved FVII and FVIIa molecules, in particular recombinant hFVII and hFVIIa molecules, providing one or more of the aforementioned desired benefits. Thus, the conjugate of the present invention has one or more improved properties as compared to commercially available rFVIIa, including increased functional in vivo half-life and/or increased plasma half-life, and/or increased bioavailability and/or reduced sensitivity to proteolytic degradation. Consequently, medical treatment with a conjugate of the invention offers a number of advantages over the currently available rFVIIa compound, such as longer duration between injections.

Accordingly, in a first aspect, the invention relates to a conjugate comprising at least one non-polypeptide moiety covalently attached to a polypeptide, wherein the amino acid sequence of the polypeptide differs from that of wild-type FVII or FVIIa shown in SEQ ID NO:1 in that at least one amino acid residue comprising an attachment group for said non-polypeptide moiety has been introduced or removed.

In another aspect, the invention relates to a polypeptide, wherein the amino acid sequence of the polypeptide differs from that of wild-type FVII or hFVIIa shown in SEQ ID NO:1 in that at least one amino acid residue comprising an attachment group for a non-polypeptide moiety has been introduced or removed. Such novel FVII polypeptides are contemplated to be useful as such for therapeutic, diagnostic or other purposes, but find particular interest as intermediate products for the preparation of a conjugate of the invention.

In further aspects, the invention relates to: a nucleotide sequence encoding the polypeptide of the invention or the polypeptide part of the conjugate of the invention; an expression vector harbouring the nucleotide sequence of the invention; a host cell comprising the nucleotide sequence of the invention or the expression vector of the invention.

In still further aspects, the invention relates to pharmaceutical compositions comprising the conjugate of the invention as well as to methods for preparing and using such conjugates.

DETAILED DISCUSSION

Definitions

In the context of the present application and invention the following definitions apply:

The term "conjugate" (or interchangeably "conjugated polypeptide") is intended to indicate a heterogeneous (in the sense of composite or chimeric) molecule formed by the covalent attachment of one or more polypeptide(s) to one or more non-polypeptide moieties such as polymer molecules, lipophilic compounds, sugar moieties or organic derivatizing agents. Preferably, the conjugate is soluble at relevant concentrations and conditions, i.e., soluble in physiological fluids such as blood. Examples of conjugated polypeptides of the invention include glycosylated and/or PEGylated polypeptides.

The term "covalent attachment" means that the polypeptide and the non-polypeptide moiety are either directly covalently joined to one another, or else are indirectly covalently joined to one another through an intervening moiety or moieties, such as a bridge, spacer, or linkage moiety or moieties.

The term "non-conjugated polypeptide" can be used about the polypeptide part of the conjugate.

When used herein, the term "non-polypeptide moiety" means a molecule that is capable of conjugating to an attachment group of the polypeptide of the invention. Preferred examples of such molecules include polymer molecules, sugar moieties, lipophilic compounds, or organic derivatizing agents. When used in the context of a conjugate of the invention it will be understood that the non-polypeptide moiety is linked to the polypeptide part of the conjugate through an attachment group of the polypeptide. As explained above, the non-polypeptide moiety can be directly covalently joined to the attachment group or it can be indirectly covalently joined to the attachment group through an intervening moiety or moieties, such as a bridge, spacer, or linkage moiety or moieties.

The "polymer molecule" is a molecule formed by covalent linkage of two or more monomers, wherein none of the monomers is an amino acid residue, except where the polymer is human albumin or another abundant plasma protein. The term "polymer" can be used interchangeably with the term "polymer molecule." The term is intended to cover carbohydrate molecules attached by in vitro glycosylation, i.e., a synthetic glycosylation performed in vitro normally involving covalently linking a carbohydrate molecule to an attachment group of the polypeptide, optionally using a cross-linking agent.

Carbohydrate molecules attached by in vivo glycosylation, such as N- or O-glycosylation (as further described below) are referred to herein as a "sugar moiety." Except where the number of non-polypeptide moieties, such as polymer molecule(s) or sugar moieties in the conjugate is expressly indicated every reference to "a non-polypeptide moiety" contained in a conjugate or otherwise used in the present invention shall be a reference to one or more non-polypeptide moieties, such as polymer molecule(s) or sugar moieties.

The term "attachment group" is intended to indicate a functional group of the polypeptide, in particular of an amino acid residue thereof or a carbohydrate moiety, capable of attaching a non-polypeptide moiety such as a polymer molecule, a lipophilic molecule, a sugar moiety or an organic derivatizing agent. Useful attachment groups and their matching non-polypeptide moieties are apparent from the table below.

| Attachment group | Amino acid | Examples of non-polypeptide moiety | Conjugation method/-Activated PEG | Reference |
|---|---|---|---|---|
| —NH$_2$ | N-terminal, Lys | Polymer, e.g., PEG, with amide or imine group | mPEG-SPA Tresylated mPEG | Shearwater Inc. Delgado et al, critical reviews in Therapeutic Drug Carrier Systems 9(3, 4): 249-304 (1992) |
| —COOH | C-terminal, Asp, Glu | Polymer, e.g., PEG, with ester or amide group Carbohydrate moiety | mPEG-Hz In vitro coupling | Shearwater Inc. |
| —SH | Cys | Polymer, e.g., PEG, with disulfide, maleimide or vinyl sulfone group Carbohydrate moiety | PEG-vinylsulphone PEG-maleimide In vitro coupling | Shearwater Inc. Delgado et al, critical reviews in Therapeutic Drug Carrier Systems 9(3, 4): 249-304 (1992) |
| —OH | Ser, Thr, Lys, OH— | Sugar moiety PEG with ester, ether, carbamate, carbonate | In vivo O-linked glycosylation | |
| —CONH$_2$ | Asn as part of an N-glycosylation site | Sugar moiety Polymer, e.g., PEG | In vivo N-glycosylation | |
| Aromatic residue | Phe, Tyr, Trp | Carbohydrate moiety | In vitro coupling | |
| —CONH$_2$ | Gln | Carbohydrate moiety | In vitro coupling | Yan and Wold, Biochemistry, 1984, Jul 31; 23(16): 3759-65 |
| Aldehyde Ketone | Oxidized oligosaccharide | Polymer, e.g., PEG, PEG-hydrazide | PEGylation | Andresz et al., 1978, Makromol. Chem. 179: 301, WO 92/16555, WO 00/23114 |
| Guanidino | Arg | Carbohydrate moiety | In vitro coupling | Lundblad and Noyes, Chimical Reagents for Protein Modification, CRC Press Inc., Florida, USA |
| Imidazole ring | His | Carbohydrate moiety | In vitro coupling | As for guanidine |

For in vivo N-glycosylation, the term "attachment group" is used in an unconventional way to indicate the amino acid residues constituting a N-glycosylation site (with the sequence N-X-S/T/C, wherein X is any amino acid residue except proline, N is asparagine and S/T/C is either serine, threonine or cysteine, preferably serine or threonine, and most preferably threonine). Although the asparagine residue of the N-glycosylation site is the one to which the sugar moiety is attached during glycosylation, such attachment cannot be achieved unless the other amino acid residues of the N-glycosylation site is present.

Accordingly, when the non-polypeptide moiety is a sugar moiety and the conjugation is to be achieved by N-glycosylation, the term "amino acid residue comprising an attachment group for the non-polypeptide moiety" as used in connection with alterations of the amino acid sequence of the polypeptide of interest is to be understood as meaning that one or more amino acid residues constituting an N-glycosylation site are to be altered in such a manner that either a functional N-glycosylation site is introduced into the amino acid sequence or removed from said sequence.

In the present application, amino acid names and atom names (e.g., CA, CB, CD, CG, SG, NZ, N, O, C, etc) are used as defined by the Protein DataBank (PDB) (www.pdb.org) based on the IUPAC nomenclature (IUPAC Nomenclature and Symbolism for Amino Acids and Peptides (residue names, atom names, etc.), *Eur. J. Biochem.*, 138, 9-37 (1984) together with their corrections in *Eur. J. Biochem.*, 152, 1 (1985)).

The term "amino acid residue" is intended to indicate an amino acid residue contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues.

The terminology used for identifying amino acid positions is illustrated as follows: G124 indicates that position 124 is occupied by a glycine residue in the amino acid sequence shown in SEQ ID NO:1. G124R indicates that the glycine residue of position 124 has been substituted with an arginine residue. Alternative substitutions are indicated with a "/," e.g., K32D/E means an amino acid sequence in which lysine in position 32 is substituted with either aspartic acid or glutamic acid. Multiple substitutions are indicated with a "+," e.g., K143N+N145S/T means an amino acid sequence which comprises a substitution of the lysine residue in position 143 with an asparagine residue and a substitution of the asparagine residue in position 145 with a serine or a threonine residue. The insertion of an additional amino acid residue, such as insertion of an alanine residue after G124 is indicated by G124GA. A deletion of an amino acid residue is indicated by an asterix. For example, deletion of a glycine in position 124 is indicated by G124*. Unless otherwise indicated, the numbering of amino acid residues made herein is made relative to the amino acid sequence of wild-type FVII/FVIIa shown in SEQ ID NO:1.

The term "differs from" as used in connection with specific mutations is intended to allow for additional differences being present apart from the specified amino acid difference. For instance, in addition to the removal and/or introduction of amino acid residues comprising an attachment group for the non-polypeptide moiety the FVII or FVIIa polypeptide can comprise other substitutions that are not related to introduction and/or removal of such amino acid residues. Thus, in addition to the amino acid alterations disclosed herein aimed at removing and/or introducing attachment sites for the non-polypeptide moiety, it will be understood that the amino acid sequence of the polypeptide of the invention can, if desired, contain other alterations that need not be related to introduction or removal of attachment sites, i.e., other substitutions, insertions or deletions. These can, for example, include truncation of the N- and/or C-terminus by one or more amino acid residues, or addition of one or more extra residues at the N- and/or C-terminus, e.g., addition of a methionine residue at the N-terminus as well as "conservative amino acid substitutions," i.e., substitutions performed within groups of amino acids with similar characteristics, e.g., small amino acids, acidic amino acids, polar amino acids, basic amino acids, hydrophobic amino acids and aromatic amino acids.

Preferred substitutions in the present invention can in particular be selected from the conservative substitution groups listed in the table below.

| 1 | Alanine (A) | Glycine (G) | Serine (S) | Threonine (T) |
|---|---|---|---|---|
| 2 | Aspartic acid (D) | Glutamic acid (E) | | |
| 3 | Asparagine (N) | Glutamine (Q) | | |
| 4 | Arginine (R) | Histidine (H) | Lysine (K) | |
| 5 | Isoleucine (I) | Leucine (L) | Methionine (M) | Valine (V) |
| 6 | Phenylalanine (F) | Tyrosine (Y) | Tryptophan (W) | |

The terms "mutation" and "substitution" are used interchangeably herein.

The term "nucleotide sequence" is intended to indicate a consecutive stretch of two or more nucleotide molecules. The nucleotide sequence can be of genomic, cDNA, RNA, semi-synthetic, synthetic origin, or any combinations thereof.

The term "polymerase chain reaction" or "PCR" generally refers to a method for amplification of a desired nucleotide sequence in vitro, as described, for example, in U.S. Pat. No. 4,683,195. In general, the PCR method involves repeated cycles of primer extension synthesis, using oligonucleotide primers capable of hybridising preferentially to a template nucleic acid.

"Cell," "host cell," "cell line" and "cell culture" are used interchangeably herein and all such terms should be understood to include progeny resulting from growth or culturing of a cell. "Transformation" and "transfection" are used interchangeably to refer to the process of introducing DNA into a cell.

"Operably linked" refers to the covalent joining of two or more nucleotide sequences, by means of enzymatic ligation or otherwise, in a configuration relative to one another such that the normal function of the sequences can be performed. For example, the nucleotide sequence encoding a presequence or secretory leader is operably linked to a nucleotide sequence coding for a polypeptide if it is expressed as a preprotein that participates in the secretion of the polypeptide: a promoter or enhancer is operably linked to a coding sequence if it affects the transcription of the sequence; a ribosome binding site is operably linked to a coding sequence if it is positioned so as to facilitate translation. Generally, "operably linked" means that the nucleotide sequences being linked are contiguous and, in the case of a secretory leader, contiguous and in reading phase. Linking is accomplished by ligation at convenient restriction sites. If such sites do not exist, then synthetic oligonucleotide adaptors or linkers are used, in conjunction with standard recombinant DNA methods.

The term "introduce" refers to introduction of an amino acid residue comprising an attachment group for a non-polypeptide moiety, in particular by substitution of an existing amino acid residue, or alternatively by insertion of an additional amino acid residue.

The term "remove" refers to removal of an amino acid residue comprising an attachment group for a non-polypeptide moiety, in particular by substitution of the amino acid residue to be removed by another amino acid residue, or alternatively by deletion (without substitution) of the amino acid residue to be removed The term "FVII" or "FVII polypeptide" refers to a FVII molecule provided in single chain form.

The term "FVIIa" or "FVIIa polypeptide" refers to a FVIIa molecule provided in its activated two-chain form, wherein the peptide bond between R152 and I153 of the single-chain form has been cleaved. When the amino acid sequence of SEQ ID NO;1 is used herein to describe the amino acid sequence of FVIIa it will be understood to that one of the chains comprises amino acid residues 1-152, the other chain amino acid residues 153-406.

The terms "rFVII" and "rFVIIa" refer to FVII and FVIIa molecules produced by recombinant techniques, respectively.

The terms "hFVII" and "hFVIIa" refer to wild-type human FVII and FVIIa, respectively.

The term "catalytic site" is used to mean the catalytic triad consisting of S344, D242 and H193 of the FVII polypeptide.

The term "active FVIIa," "active FVIIa polypeptide," "active FVIIa conjugate" or "active conjugate" is used to mean a FVIIa polypeptide or conjugate that possesses at least 10% of the catalytic activity of wild-type hFVIIa. Catalytic acitivity, as used herein, can suitably be determined in the assay described in the section entitled Method of measuring the catalytic activity or in the assay entitled Method of measuring low levels of catalytic activity (see the Materials and Methods section herein). Preferably, an active conjugate has at least 15%, such as at least 20%, e.g., at least 25%, more preferably at least 30%, such as at least 40%, most preferably at least 50%, e.g., at least 60% of the catalytic acitivity of wild-type hFVIIa, when tested in the assays described above.

Preferably, an active conjugate is able to bind to tissue factor and further activate plasma factor X and/or IX. Thus, in a preferred embodiment, the active FVIIa polypeptide or a conjugate thereof has a clotting activity of at least 25% as compared to wild type FVIIa, such as a clotting activity of at least 50% as compared to wild type FVIIa, e.g., a clotting activity of at least 75% as compared to wild type FVII. Thus, the clotting activity of the active FVIIa polypeptide or conjugate thereof is preferably in the range of 25-200% as compared to the wild type FVIIa. In particular, it is preferred that the FVIIa polypeptide or conjugate has a clotting activity in the range of 30-150% as compared to wild type FVIIa, such as a clotting activity in the range of 30-100% as compared to wild type FVIIa. The clotting activity can be determined by any method known in the art as further discussed in the Materials and Methods section hereinafter. It is particularly preferred, however, that the clotting activity is determined in accordance with the method described in the section entitled "Method of measuring the clotting Activity" (see the Materials and Method section).

The term "immunogenicity" as used in connection with a given substance is intended to indicate the ability of the substance to induce a response from the immune system. The immune response can be a cell or antibody mediated response (see, e.g., Roitt: Essential Immunology ($8^{th}$ Edition, Blackwell) for further definition of immunogenicity). Normally, reduced antibody reactivity will be an indication of reduced immunogenicity. The reduced immunogenicity can be determined by use of any suitable method known in the art, e.g., in vivo or in vitro.

The term "inactive FVIIa," "inactive FVIIa polypeptide," "inactive FVIIa conjugate" or "inactive conjugate" is used to mean a FVIIa polypeptide or conjugate that possesses less than 10% of the catalytic activity of wild-type hFVIIa. Catalytic acitivity, as used herein, can suitably be determined in the assay described in the section entitled Method of measuring the catalytic activity or in the assay entitled Method of measuring low levels of catalytic activity (see the Materials and Methods section herein). Preferably, an inactive conjugate has less than 8%, such as less than 6%, e.g., less than 5%, more preferably less than 4%, such as less than 3%, most preferably less than 2%, e.g., less than 1% of the catalytic activity of wild-type hFVIIa, when tested in the assays described above.

Typically, an inactive conjugate has significantly reduced in vitro or in vivo clotting activity as compared to wild-type hFVIIa. The inactive FVII or FVIIa polypeptide or conjugate can be capable of competing with wild-type FVII or FVIIa for binding tissue factor, thereby inhibiting clotting activity. Preferably, the inactive FVII or FVIIa polypeptide or conjugate has less than 1% clotting activity compared to wild-type hFVII or hFVIIa. More preferably the inactive FVII or FVIIa polypeptide or conjugate has less than 0.05% clotting activity compared to wild type hFVII or hFVIIa. Most preferably the inactive FVII or FVIIa polypeptide or conjugate has less than 0.01% clotting activity as compared to wild type hFVII or hFVIIa. In a similar way as described above, the clotting activity can be determined by any method known in the art as further discussed in the Materials and Method section hereinafter, but is preferably determined in accordance with the method described in the section entitled "Method of measuring the clotting activity."

The term "functional in vivo half-life" is used in its normal meaning, i.e., the time at which 50% of the biological activity of the polypeptide or conjugate is still present in the body/ target organ, or the time at which the activity of the polypeptide or conjugate is 50% of the initial value. As an alternative to determining functional in vivo half-life, "serum half-life" can be determined, i.e., the time at which 50% of the polypeptide or conjugate molecules circulate in the plasma or bloodstream prior to being cleared. Determination of serum half-life is often more simple than determining the functional in vivo half-life and the magnitude of serum half-life is usually a good indication of the magnitude of functional in vivo half-life. Alternatively terms to serum half-life include "plasma half-life," "circulating half-life," "serum clearance," "plasma clearance" and "clearance half-life." The polypeptide or conjugate is cleared by the action of one or more of the reticuloendothelial systems (RES), kidney, spleen or liver, by tissue factor, SEC receptor or other receptor mediated elimination, or by specific or unspecific proteolysis. Normally, clearance depends on size (relative to the cutoff for glomerular filtration), charge, attached carbohydrate chains, and the presence of cellular receptors for the protein. The functionality to be retained is normally selected from procoagulant, proteolytic or receptor binding activity. The functional in vivo half-life and the serum half-life can be determined by any suitable method known in the art as further discussed in the Materials Methods section below.

The term "increased" as used about the functional in vivo half-life or plasma half-life is used to indicate that the relevant half-life of the conjugate or polypeptide is statistically significantly increased relative to that of a reference molecule, such as a non-conjugated rFVIIa (e.g., NovoSeven®) as determined under comparable conditions. For instance, the relevant half-life can increased by at least about 25%, such as by at least about 50%, e.g., by at least about 100%, 150%, 200%, 250%, 300%, 500% or 1000%.

The term "renal clearance" is used in its normal meaning to indicate any clearance taking place by the kidneys, e.g., by glomerular filtration, tubular excretion or degradation in the tubular cells. Renal clearance depends on physical characteristics of the conjugate, including size (diameter), hydrodynamic volume, symmetry, shape/rigidity, and charge. Normally, a molecular weight of about 67 kDa is considered to be a cut-off-value for renal clearance. Renal clearance can be established by any suitable assay, e.g., an established in vivo assay. Typically, renal clearance is determined by administering a labelled (e.g., radiolabelled or fluorescence labelled) polypeptide conjugate to a patient and measuring the label activity in urine collected from the patient. Reduced renal clearance is determined relative to a corresponding reference polypeptide, e.g., the corresponding non-conjugated polypeptide, a non-conjugated corresponding wild-type polypeptide or another conjugated polypeptide (such as a conjugated polypeptide not according to the invention), under comparable conditions. Preferably, the renal clearance rate of the conjugate is reduced by at least 50%, preferably by at least 75%, and most preferably by at least 90% compared to a relevant reference polypeptide.

The ability of the conjugates of the invention to exhibit a reduced sensitivity to proteolytic degradation is of utmost importance; Compositions comprising degradation products will typically have less specific activity as compared to compositions in which none or only a minor part of the conjugate has been degraded. Furthermore, a content of non-physiological degradation products in the composition to be administered can trigger the immune system of the patient.

The term "reduced sensitivity to proteolytic degradation" is primarily intended to mean that the conjugate has reduced sensitivity to proteolytic degradation in comparison to non-conjugated wild type FVIIa as determined under comparable conditions. Preferably, the proteolytic degradation is reduced by at least 10%, such as at least 25% (e.g., by 10-25%), more preferably by at least 35%, such as at least 50%, (e.g., by 10-50%) even more preferably by at least 60%, such as by at least 75% or even at least 90%. Most preferably, the proteolytic degradation is reduced by 100%. Thus, preferably the conjugate of the invention is subjected to proteolytic degradation to a lesser extent than wild-type FVIIa, i.e., compared to non-conjugated wild type FVIIa the proteolytic degradation of the conjugate of the invention is preferably reduced by 10-100%, such as by 25-100%, more preferably by 50-100%, and most preferably by 75-100%.

The present inventors have developed a suitable preliminary in vitro test, which can be employed in the assessment of whether such conjugates possess reduced sensitivity to proteolytic cleavage (reduced autoproteolysis). Thus, in a preferred embodiment, of the invention, the conjugate of the invention has a reduced sensitivity to proteolytic degradation (as defined above) as compared to wild type FVIIa when determined by the method described in the section entitled "Measurement of reduced sensitivity to proteolytic degradation," when determined by the method described in the section entitled Method of measuring the catalytic activity or when determined by the method described in the section entitled Method of measuring low levels of catalytic activity (see the Materials and Methods section herein).

The term "parent FVII" or "parent polypeptide" is intended to indicate the molecule to be modified in accordance with the present invention. A typical parent FVII is the hFVII or hFVIIa (including rFVIIa (NovoSeven®)) with the amino acid sequence shown in SEQ ID NO:1.

A "variant" is a polypeptide, which differs in one or more amino acid residues from a parent polypeptide, normally in 1, 2, 3, 4, 5, 6, 7, 8, 9, 10, 11, 12, 13, 14 or 15 amino acid residues.

Conjugate of the Invention

The conjugates of the invention are the result of a generally new strategy for developing improved FVII or FVIIa molecules. More specifically, by removing and/or introducing an amino acid residue comprising an attachment group for the non-polypeptide moiety it is possible to specifically adapt the polypeptide so as to make the molecule more susceptible to conjugation to the non-polypeptide moiety of choice, to optimize the conjugation pattern (e.g., to ensure an optimal distribution and number of non-polypeptide moieties on the surface of the FVII or FVIIa molecule and to ensure that only the attachment groups intended to be conjugated is present in the molecule) and thereby obtain a new conjugate molecule, which has or has not FVII activity and in addition one or more improved properties as compared to FVII and FVIIa molecules available today. For instance, when the total number of amino acid residues comprising an attachment group for the non-polypeptide of choice is increased or decreased to an optimized level, the renal clearance of the conjugate is typically significantly reduced due to the altered shape, size and/or charge of the molecule achieved by the conjugation.

In preferred embodiments of the present invention more than one amino acid residue of the FVII or FVIIa polypeptide is altered, e.g., the alteration embraces removal as well as introduction of amino acid residues comprising an attachment group for the non-polypeptide moiety of choice. In addition to the removal and/or introduction of amino acid residues the polypeptide can comprise other substitutions or glycosylations that are not related to introduction and/or removal of amino acid residues comprising an attachment group for the non-polypeptide moiety. Also, the polypeptide can be attached, e.g., to a serine proteinase inhibitor to inhibit the catalytic site of the polypeptide.

The amino acid residue comprising an attachment group for a non-polypeptide moiety, either it be removed or introduced, is selected on the basis of the nature of the non-polypeptide moiety of choice and, in most instances, on the basis of the method in which conjugation between the polypeptide and the non-polypeptide moiety is to be achieved. For instance, when the non-polypeptide moiety is a polymer molecule such as a polyethylene glycol or polyalkylene oxide derived molecule amino acid residues comprising an attachment group can be selected from the group consisting of lysine, cysteine, aspartic acid, glutamic acid, histidine, and tyrosine, preferably cysteine and lysine, in particular lysine.

Whenever an attachment group for a non-polypeptide moiety is to be introduced into or removed from the FVII or FVIIa polypeptide in accordance with the present invention, the position of the polypeptide to be modified is preferably located at the surface of the poly-peptide, and more preferably occupied by an amino acid residue which has more than 25% of its side chain exposed to the solvent, preferably more than 50% of its side chain exposed to the solvent. Such positions have been identified on the basis of an analysis of a 3D structure of the human FVII or FVIIa molecule as described in the Materials and Methods section herein. Furthermore, the position is preferably selected from a part of the FVII molecule that is located outside a tissue factor binding site region and/or an active site region. These regions are identified in the Materials and Methods section hereinafter. It should be emphasized, however, that in certain situations, e.g., in case an inactivated conjugate is desired, it can be advantageous to perform modifications in or close to such regions. For example, it is contemplated that one or more attachment groups for the non-polypeptide moieties, such as attachment groups for in vivo N-glycosylation sites, can advantageously be inserted in the active site region or at the ridge of the active site binding cleft of the FVII molecule. The active site region and the ridge of the active site binding cleft are defined in the Materials and Methods section herein and is constituted by the following residues:

I153, Q167, V168, L169, L170, L171, Q176, L177, C178, G179, G180, T181, V188, V189, S190, A191, A192, H193, C194, F195, D196, K197, I198, W201, V228, I229, I230, P231, S232, T233, Y234, V235, P236, G237, T238, T239, N240, H241, D242, I243, A244, L245, L246, V281, S282, G283, W284, G285, Q286, T293, T324, E325, Y326, M327, F328, D338, S339, C340, K341, G342, D343, S344, G345, G346, P347, H348, L358, T359, G360, I361, V362, S363, W364, G365, C368, V376, Y377, T378, R379, V380, Q382, Y383, W386, L387, L400 and F405 (active site region); and N173, A175, K199, N200, N203, D289, R290, G291, A292, P321 and T370 (the ridge of the active site binding cleft).

In order to determine an optimal distribution of attachment groups, the distance between amino acid residues located at the surface of the FVII or FVIIa molecule is calculated on the basis of a 3D structure of the polypeptide. More specifically, the distance between the CB's of the amino acid residues comprising such attachment groups, or the distance between the functional group (NZ for lysine, CG for aspartic acid, CD for glutamic acid, SG for cysteine) of one and the CB of another amino acid residue comprising an attachment group are determined. In case of glycine, CA is used instead of CB. In the FVII or FVIIa polypeptide part of a conjugate of the invention, any of said distances is preferably more than 8 Å, in particular more than 10 Å in order to avoid or reduce heterogeneous conjugation.

In case of removal of an attachment group, the relevant amino acid residue comprising such group and occupying a position as defined above is preferably substituted with a different amino acid residue that does not comprise an attachment group for the non-polypeptide moiety in question. Normally, the amino acid residue to be removed is one to which conjugation is disadvantageous, e.g., an amino acid residue located at or near a functional site of the polypeptide (since conjugation at such a site can result in inactivation or reduced FVII or FVIIa activity of the resulting conjugate due to impaired receptor recognition). In the present context the term "functional site" is intended to indicate one or more amino acid residues which is/are essential for or otherwise involved in the function or performance of FVII or FVIIa. Such amino acid residues are a part of the functional site. The functional site can be determined by methods known in the art and is preferably identified by analysis of a structure of the FVIIa-tissue factor complex (See Banner et al., Nature 1996; 380:41-46).

In case of introduction of an attachment group, an amino acid residue comprising such group is introduced into the position, preferably by substitution of the amino acid residue occupying such position.

The exact number of attachment groups present and available for conjugation in the FVII or FVIIa polypeptide is dependent on the effect desired to be achieved by the conjugation. The effect to be obtained is, e.g., dependent on the nature and degree of conjugation (e.g., the identity of the non-polypeptide moiety, the number of non-polypeptide moieties desirable or possible to conjugate to the polypeptide, where they should be conjugated or where conjugation should be avoided, etc.).

Functional in vivo half-life is i.a. dependent on the molecular weight of the conjugate, and the number of attachment groups needed for providing increased half-life thus depends on the molecular weight of the non-polypeptide moiety in question. In one embodiment, the conjugate of the invention has a molecular weight of at least 67 kDa, in particular at least 70 kDa, e.g., as measured by SDS-PAGE according to Laemmli, U.K., Nature Vol 227 (1970), p 680-85. FVII has a molecular weight of about 53 kDa, and therefore additional 10-20 kDa is required to obtain the desired effect. This can, e.g., be provided by conjugating 2-4 10 kDa PEG molecules or as otherwise described herein.

In order to avoid too much disruption of the structure and function of the parent molecule the polypeptide part of the conjugate will typically have an amino acid sequence having more than 90% identity with SEQ ID NO:1, preferably more than 95%, such as more than 96%. In particular, the polypeptide part of the conjugate will typically have an amino acid sequence having more than 97% identity with SEQ ID NO:1, such as more than 98%, more than 99%, more than 99.25%, more than 99.25% or more than 99.5%.

Amino acid sequence homology/identity is conveniently determined from aligned sequences, using e.g., the ClustalW program, version 1.8, June 1999, using default parameters (Thompson et al., 1994, ClustalW: Improving the sensitivity of progressive multiple sequence alignment through sequence weighting, position-specific gap penalties and weight matrix choice, Nucleic Acids Research, 22: 4673-4680) or from the PFAM families database version 4.0 (http://pfam.wustl.edu/) (*Nucleic Acids Res.* 1999 Jan. 1; 27(1):260-2) by use of GENEDOC version 2.5 (Nicholas, K. B., Nicholas H. B. Jr., and Deerfield, D. W. II. 1997 GeneDoc: Analysis and Visualization of Genetic Variation, EMBNEW.NEWS 4:14; Nicholas, K. B. and Nicholas H. B. Jr. 1997 GeneDoc: Analysis and Visualization of Genetic Variation).

Stated differently, the total number of amino acid residues to be altered in accordance with the present invention (as compared to the amino acid sequence shown in SEQ ID NO:1) will typically not exceed 15. Preferably, the FVII or FVIIa polypeptide part of the conjugate of the invention or the polypeptide of the invention comprises an amino acid sequence differing in 1-15 amino acid residues from the amino acid sequence shown in SEQ ID NO:1, typically in 1-10 or in 2-10 amino acid residues, e.g., in 1-8 or in 2-8 amino acid residues, such as in 3-7 or in 4-6 amino acid residues from the amino acid sequence shown in SEQ ID NO:1. Thus, normally the polypeptide part of the conjugate or the polypeptide of the invention comprises an amino acid sequence which differs from the amino acid sequence shown in SEQ ID NO:1 in at the most 15 amino acid residues (such as 15 amino acid residues), in at the most 14 amino acid residues (such as 14 amino acid residues), in at the most 13 amino acid residues (e.g., 13 amino acid residues), in at the most 12 amino acid residues (such as 12 amino acid residues), in at the most 11 amino acid residues (such as 11 amino acid residues), in at the most 10 amino acid residues (e.g., 10 amino acid residues), in at the most 9 amino acid residues (such as 9 amino acid residues), in at the most 8 amino acid residues (such as 8 amino acid residues), in at the most 7 amino acid residues (such as 7 amino acid residues), in at the most 6 amino acid residues (such as 6 amino acid residues), in at the most 5 amino acid residues (such as 5 amino acid residues), in at the most 4 amino acid residues (such as 4 amino acid residues), in at the most 3 amino acid residues (such as 3 amino acid residues) or in at the most 2 amino acid residues (such as 2 amino acid residues).

Analogously, the conjugate of the invention typically contains, e.g., 1-15 non-polypeptide moieties, typically 1-10 non-polypeptide moieties or 2-10 non-polypeptide moieties, such as 1-8 or 2-8 non-polypeptide moieties, e.g., 1-6, 1-4, 3-7 or 4-6 non-polypeptide moieties.

Preferably, the conjugate of the invention has one or more of the following improved properties: Increased functional in vivo half-life, increased plasma half-life, reduced renal clearance and reduced sensitivity to proteolytic degradation as compared to rFVIIa (e.g. NovoSeven®).

It is known from, inter alia, WO 88/10295 that proteolytic degradation of FVII/FVIIa primarily takes place at various proteolytic sites in the molecule, namely at the positions K32, K38, I42, Y44, K143, R290, R315, K341, R392, R396 and R402 (or rather between the positions K32-D33, K38-L39, I42-S43, Y44-S45, K143-R144, R290-G291, R315-K316, K341-G342, R392-S393, R396-P397 and R402-A403). Thus, one preferred strategy for increasing e.g., the functional in vivo half-life, the increased plasma half-life or for reducing the sensitivity to proteolytic degradation is to modify the parent polypeptide at and/or around one or more of these proteolytic degradation sites, e.g., by introducing non-polypeptide moieties at and/or around these sites. Thus, in a preferred embodiment, of the invention, an attachment group has been introduced in one or more of the above-mentioned identified positions or at position −4, −3, −2, −1, 1, 2, 3, 4, preferably position −2, −1, 1, 2, such as position −1, 1, relative to the position directly involved in proteolytic degradation.

More specifically, it is preferred that a non-naturally occurring in vivo glycosylation site, in particular a non-naturally occurring in vivo N-glycosylation site (see further below) has been introduced in positions selected from the group consisting of 28-48, 139-147, 286-294, 311-319, 338-345, and 388-406. In particular, it is preferred that the in vivo glycosylation site, such as an in vivo N-glycosylation site (see further below) has been introduced in positions selected from the group consisting of 30-34, 36-46, 141-144, 288-292, 313-317, 341-343, 390-398 and 400-404. More preferably, the in vivo glycosylation site, such as an in vivo N-glycosylation site (see further below) has been introduced in positions selected from the group consisting of 31-33 (e.g., positions 31, 32 or 33), 37-39 (e.g., positions 37, 38 or 39), 41-46 (e.g., positions 41, 42, 43, 44, 45 or 46), 142-144 (e.g., positions 142, 143 or 144), 289-291 (e.g., positions 289, 290 or 291), 314-316, (e.g., positions 314, 315 or 316), 341-342 (e.g., positions 341, 342 or 343), 391-393 (e.g., positions 391, 392 or 393), 395-397 (e.g., positions 395, 396 or 397) and 401-403 (e.g., positions 401, 402 or 403). The introduction is preferably performed by substitution.

Conjugate of the Invention, wherein the Non-polypeptide Moiety is a Molecule that has Lysine as an Attachment Group In another embodiment of the invention, the non-polypeptide moiety has lysine as an attachment group, i.e., the conjugate of the invention is one which comprises at least one non-polypeptide moiety covalently attached to a polypeptide, wherein the amino acid sequence of the polypeptide differs from that of wild-type FVII or FVIIa shown in SEQ ID NO:1 in that at least one lysine residue has been introduced or removed.

FVII/FVIIa contains 17 lysine residues. Three lysine residues (K18, K62 and K85) are located in the tissue factor binding domain and two lysine residues (K197 and K341) are located in the active site region.

Due to the relative high amount of lysine residues in the parent polypeptide it is envisaged that at least one lysine residue should preferably be removed, in particular by substitution of a lysine residue with a non-lysine residue, in order to avoid excessive conjugation to non-polypeptide moieties.

Thus, in one embodiment, the amino acid sequence of the FVII or FVIIa polypeptide part of the conjugate differs from that shown in SEQ ID NO:1 in that at least one lysine residue, such as 1-15 lysine residues, in particular 1-10, 1-6 or 2-4 lysine residues, has been removed, preferably by substitution. For example, the lysine residue(s) to be removed, preferably by substitution, is selected from the group consisting of K18, K32, K38, K62, K85, K109, K137, K143, K148, K157, K161, K197, K199, K316, K337, K341, K389 and combinations thereof. In particular, it is preferred to remove one or more lysine residues, which constitute part of tissue factor binding site and/or the active site region, i.e., the residues K18, K62, K85, K197, K341 or combinations thereof. The lysine residue can be substituted with any other amino acid residue, but is preferably substituted with R, Q, N or H, more preferably R.

In another embodiment, the amino acid sequence of the FVII or FVIIa polypeptide part of the conjugate differs from that shown in SEQ ID NO:1 in that at least one lysine residue, such as 1-15 lysine residues, in particular 1-10, 1-6 or 2-4 lysine residues, has been introduced, preferably by substitution. It will be understood that it is particularly preferred that at least one of the lysines residues, which are introduced at a predetermined site in the parent molecule, is combined with at least one of the above-mentioned removals of lysine residues. Thus, in a preferred embodiment of the invention, the amino acid sequence of the FVII or FVIIa polypeptide part of the conjugate differs from that shown in SEQ ID NO:1 in that at least one lysine residue has been removed and at least one lysine residue has been introduced.

Examples of positions, wherein lysine residues can be introduced include, but is not limited to, positions at or in the vicinity of the proteolytic degradation sites described above. Thus, in a preferred embodiment, the substitution of a non-lysine residue with a lysine residue is selected from the group consisting of I42K, Y44K, L288K, D289K, R290K, G291K, A292K, T293K, Q313K, S314K, R315K, V317K, L390K, M391K, R392K, S393K, E394K, P395K, R396K, P397K, G398K, V399K, L400K, L401K, R402K, A403K, P404K, F405K and combinations thereof, in particular selected from the group consisting of R290K, R315K, R392K, R396K, R402K and combinations thereof.

While the non-polypeptide moiety of the conjugate according to this aspect of the invention can be any molecule which, when using the given conjugation method has lysine as an attachment group it is preferred that the non-polypeptide moiety is a polymer molecule. The polymer molecule can be any of the molecules mentioned in the section entitled "Conjugation to a polymer molecule," but is preferably selected from the group consisting of linear or branched polyethylene glycol or another polyalkylene oxide. Examples of preferred polymer molecules are, e.g., SS-PEG, NPC-PEG, aldehyde-PEG, mPEG-SPA, mPEG-SCM, mPEG-BTC from Shearwater Polymers, Inc, SC-PEG from Enzon, Inc., tresylated mPEG as described in U.S. Pat. No. 5,880,255, or oxycarbonyl-oxy-N-dicarboxylmide-PEG (U.S. Pat. No. 5,122,614).

Normally, for conjugation to a lysine residue the non-polypeptide moiety has a molecular weight of from about 5 to about 20 kDa, such as from about 5 to about 10 kDa, e.g., about 5 kDa or about 10 kDa It will be understood that any of the amino acid changes, in particular substitutions, specified in this section can be combined with any of the amino acid changes, preferably substitutions specified in the other sections herein disclosing specific amino acid modifications, including introduction and/or removal of glycosylation sites.

Conjugate of the Invention wherein the Non-polypeptide Moiety is a Molecule that has Cysteine as an Attachment Group In a further embodiment of the invention, the non-polypeptide moiety has cysteine as an attachment group, i.e., the conjugate of the invention is one which comprises at least one non-polypeptide moiety covalently attached to a polypeptide, wherein the amino acid sequence of the polypeptide differs from that of wild-type FVII or FVIIa shown in SEQ ID NO:1 in that at least one cysteine residue has been introduced or removed.

FVII/FVIIa contains 24 cysteine residues and disulfide bridges are established between the following cysteine residues: C17 and C22, C50 and C61, C55 and C70, C72 and C81, C91 and C102, C98 and C112, C114 and C127, C135 and C262, C159 and C164, C178 and C194, C310 and C329, and between C340 and C368.

In a further interesting embodiment, the amino acid sequence of the FVII or FVIIa polypeptide differs from that shown in SEQ ID NO:1 in that at least one cysteine residue, such as 1-15 cysteine residues, in particular 1-10, 1-6 or 2-4 cysteine residues, has been introduced, preferably by substitution.

Examples of positions, wherein cysteine residues can be introduced include, but is not limited to, positions at or in the vicinity of the proteolytic degradation sites described above.

Thus, in an interesting embodiment of the invention, the lysine residue(s) to be introduced, preferably by substitution, is selected from the group consisting of I30C, K32C, D33C, A34C, T37C, K38C, W41C, Y44C, S45C, D46C, L141C, E142C, K143C, R144C, L288C, D289C, R290C, G291C, A292C, S314C, R315C, K316C, V317C, L390C, M391C, R392C, S393C, E394C, P395C, R396C, P397C, G398C, V399C, L401C, R402C, A403C, P404C and combinations thereof, in particular selected from the group consisting of K32C, Y44C, K143C, R290C, R315C, K341C, R392C, R396C, R402C and combinations thereof.

In a further embodiment of the invention, the cysteine residue(s) is/are introduced into a position that in wildtype hFVII is occupied by a threonine or serine residue having at least 25% of its side chain exposed to the surface. For instance, in the FVII or FVIIa polypeptide a cysteine residue is introduced, preferably by substitution, into at least one position selected from the group consisting of S12, S23, S43, S45, S52, S53, S60, S67, T83, S103, T106, T108, S111, S119, S126, T128, T130, S147, T185, S214, S222, S232, T233, T238, T239, T255, T267, T293, T307, S320, T324, S333, S336, T370 and S393. Even more preferably the cysteine residue is introduced into at least one position of hFVII containing an S residue, the position being selected from the group consisting of S12, S23, S43, S45, S52, S53, S60, S67, S103, S111, S119, S126, S147, S214, S222, S232, S320, S333, S336 and S393.

In a further embodiment, the cysteine residue(s) is/are introduced into a position that in wildtype hFVII is occupied by a threonine or serine residue having at least 50% of its side chain exposed to the surface. For instance, in the FVII or FVIIa polypeptide a cysteine residue is introduced, preferably by substitution, into at least one position selected from the group consisting of S23, S43, S52, S53, S60, S67, T106, T108, S111, S119, S147, S214, T238, T267 and T293, even more preferably a position selected from the group consisting of S23, S43, S52, S53, S60, S67, S111, S119, S147 and S214.

In a still further embodiment, a cysteine residue is introduced into at least one position selected from any of the above-mentioned positions, which is not located in an active site region. Preferably, the position is one occupied by a T or an S residue. As an example, the FVII polypeptide comprises a cysteine residue introduced into at least one position selected from the group consisting of S12, S23, S43, S45, S52, S53, S60, S67, T83, S103, T106, T108, S111, S119, S126, T128, T130, S147, T185, S214, S222, T255, T267, T307, S320, S333, S336, T370 and S393 (having more than 25% of its side chain exposed to the surface), in particular selected from the group consisting of S12, S23, S43, S45, S52, S53, S60, S67, S103, S111, S119, S126, S147, S214, S222, S320, S333, S336 and S393 (occupied by S residue), and more preferably from the group consisting of S23, S43, S52, S53, S60, S67, T106, T108, S111, S119, S147, S214 and T267 (having more than 50% of its side chain exposed to the surface), in particular from the group consisting of S23, S43, S52, S53, S60, S67, S111, S119, S147 and S214 (occupied by an S residue).

In an even further embodiment, a cysteine residue is introduced into at least one position selected from any of the above lists, which is not located in a tissue factor binding site region. Preferably, the position is one occupied by a T or an S residue. As an example, the FVII polypeptide comprises a cysteine residue introduced into at least one position selected from the group consisting of S12, S23, S45, S52, S53, S67, T83, S103, T106, T108, S111, S119, S126, T128, T130, S147, T185, S214, S222, S232, T233, T238, T239, T255, T267, T293, S320, T324, S333, S336, T370 and S393 (having more than 25% of its side chain exposed to the surface), in particular selected from the group consisting of S12, S23, S45, S52, S53, S67, S103, S111, S119, S126, S147, S214, S222, S232, S320, S333, S336 and S393 (occupied by S residue), and more preferably from the group consisting of S23, S52, S53, S67, T106, T108, S111, S119, S147, S214, T238, T267 and T293 (having more than 50% of its side chain exposed to the surface), in particular from the group consisting of S23, S52, S53, S67, S111, S119, S147 and S214 (occupied by an S residue).

In a still further embodiment, a cysteine residue is introduced into at least one position selected from any of the above lists, which is neither located in a tissue factor binding site region nor in an active site region. Preferably, the position is one occupied by a T or an S residue. As an example, the FVII polypeptide comprises a cysteine residue introduced into at least one position selected from the group consisting of S12, S23, S45, S52, S53, S67, T83, S103, T106, T108, S111, S119, S126, T128, T130, S147, T185, S214, S222, T255, T267, S320, S333, S336, T370 and S393 (having more than 25% of its side chain exposed to the surface), in particular selected from the group consisting of S12, S23, S45, S52, S53, S67, S103, S111, S119, S126, S147, S214, S222, S320, S333, S336 and S393 (occupied by S residue), and more preferably from the group consisting of S23, S52, S53, S67, T106, T108, S111, S119, S147, S214 and T267 (having more than 50% of its side chain exposed to the surface), in particular from the group consisting of S23, S52, S53, S67, S111, S119, S147 and S214 (occupied by an S residue).

While the non-polypeptide moiety of the conjugate according to this aspect of the invention can be any molecule which, when using the given conjugation method has cysteine as an attachment group it is preferred that the non-polypeptide moiety is a polymer molecule. The polymer molecule can be any of the molecules mentioned in the section entitled "Conjugation to a polymer molecule," but is preferably selected from the group consisting of linear or branched polyethylene glycol or another polyalkylene oxide. In another embodiment, the polymer molecule is PEG, such as VS-PEG. The conjugation between the polypeptide and the polymer can be achieved in any suitable manner, e.g., as described in the section entitled "Conjugation to a polymer molecule," e.g., in using a one step method or in the stepwise manner referred to in said section. When the FVII or FVIIa polypeptide comprises only one conjugatable cysteine residue, this is preferably conjugated to a non-polypeptide moiety with a molecular weight of from about 5 kDa to about 20 kDa, e.g., from about 10 kDa to about 20 kDa, such as a molecular weight of about 5 kDa, about 10 kDa, about 12 kDa, about 15 kDa or about 20 kDa, either directly conjugated or indirectly through a low molecular weight polymer (as disclosed in WO 99/55377). When the conjugate comprises two or more conjugatable cysteine residue, normally each of the non-polypeptide moieties has a molecular weight of from about 5 to about 10 kDa, such as about 5 kDa or about 10 kDa.

It will be understood that any of the amino acid changes, in particular substitutions, specified in this section can be combined with any of the amino acid changes, preferably substitutions specified in the other sections herein disclosing specific amino acid modifications, including introduction and/or removal of glycosylation sites.

Conjugate of the Invention wherein the Non-polypeptide Moiety is a Molecule that has Aspartic Acid or Glutamic Acid as an Attachment Group.

In a still further interesting embodiment of the invention, the non-polypeptide moiety has aspartic acid or glutamic acid as an attachment group, i.e., the conjugate of the invention is one which comprises at least one non-polypeptide moiety covalently attached to a polypeptide, wherein the amino acid sequence of the polypeptide differs from that of wild-type FVII or FVIIa shown in SEQ ID NO:1 in that at least one aspartic acid residue and/or at least one glutamic acid residue has been introduced or removed.

In a further interesting embodiment, the amino acid sequence of the FVII or FVIIa polypeptide differs from that shown in SEQ ID NO:1 in that at least one aspartic acid residue and/or glutamic acid residue, such as 1-15 aspartic acid residues and/or glutamic acid residues, in particular 1-10, 1-6 or 2-4 aspartic acid residues and/or glutamic acid residues, has been introduced, preferably by substitution.

Examples of positions, wherein aspartic acid residues or glutamic acid residues can be introduced include, but is not limited to, positions at or in the vicinity of the proteolytic degradation sites described above.

Thus, in an interesting embodiment of the invention, the aspartic acid residue and/or the glutamic acid residue to be introduced, preferably by substitution, is selected from the group consisting of I30D/E, K32D/E, A34D/E, T37D/E, K38D/E, W41D/E, Y44D/E, S45D/E, D46C, L141D/E, E142D/E, K143D/E, R144D/E, L288D/E, R290D/E, G291D/E, A292D/E, Q313D/E, S314D/E, R315D/E, K316D/E, V317D/E, L390D/E, M391D/E, R392DE, S393D/E, P395DE, R396D/E, P397D/E, G398D/E, V399D/E, L401DE, R402D/E, A403D/E, P404D/E, and combinations thereof, in particular selected from the group consisting of K32D/E, Y44D/E, K143D/E, R290D/E, R315D/E, K341D/E, R392D/E, R396D/E, R402D/E and combinations thereof.

In addition to the above listed substitution(s), the polypeptide of the conjugate according to the above embodiment can comprise removal, preferably by substitution, of at least one of the aspartic acid residue and/or at least one glutamic acid residue.

Due to the relative high amount of lysine residues in the parent polypeptide it is envisaged that at least one aspartic acid or glutamic acid residue should preferably be removed, in particular by substitution, in order to avoid excessive conjugation to non-polypeptide moieties.

Thus, in one embodiment, the amino acid sequence of the FVII or FVIIa polypeptide part of the conjugate differs from that shown in SEQ ID NO:1 in that at least one aspartic acid or glutamic acid residue, such as 1-15 aspartic acid or glutamic acid residues, in particular 1-10, 1-6 or 2-4 aspartic acid or glutamic acid residues, has been removed, preferably by substitution. For example, the aspartic acid and glutamic acid residue(s) to be removed, preferably by substitution, is selected from the group consisting of D33, D46, D48, E77, E82, D86, D87, E94, E99, D104, E116, D123, E132, E142, E163, D196, E210, D212, E215, D217, D219, E220, D256, E265, E270, D289, E296, D309, D319, E325, D334, D338, D343, E385, E394 and combinations thereof.

It will be understood that it is particularly preferred that at least one of the aspartic acid or glutamic acid residues, which are introduced at a predetermined site in the parent molecule, is combined with at least one of the above-mentioned removals of aspartic acid or glutamic acid residues. Thus, in a preferred embodiment of the invention, the amino acid sequence of the FVII or FVIIa polypeptide part of the conjugate differs from that shown in SEQ ID NO:1 in that at least one aspartic acid or glutamic acid residue has been removed, preferably by substitution, and at least one aspartic acid or glutamic acid residue has been introduced, preferably by substitution.

While the non-polypeptide moiety of the conjugate according to this aspect of the invention, which has an aspartic acid group or a glutamic acid group as an attachment group, can be any non-polypeptide moiety with such property, it is presently preferred that the non-polypeptide moiety is a polymer molecule or an organic derivatizing agent, in particular a polymer molecule, and the conjugate is prepared, e.g., as described by Sakane and Pardridge, Pharmaceutical Research, Vol. 14, No. 8, 1997, pp 1085-1091.

It will be understood that any of the amino acid changes, in particular substitutions, specified in this section can be combined with any of the amino acid changes, in particular substitutions specified in the other sections herein disclosing specific amino acid changes, including introduction and/or removal of glycosylation sites.

Conjugate of the Invention wherein the Non-polypeptide Moiety is a Sugar Moiety

In a further interesting embodiment of the invention, an attachment group for a sugar moiety, such as a glycosylation site, in particular an in vivo glycosylation site, has been inserted and/or removed.

Preferably, the conjugate of the invention is one which comprises at least one sugar moiety covalently attached to a polypeptide, wherein the amino acid sequence of the polypeptide differs from that of wild-type FVII or FVIIa shown in SEQ ID NO:1 in that at least one non-naturally occurring glycosylation site has been introduced and/or at least one naturally occurring glycosylation site has been removed. In particular, a non-naturally occurring glycosylation site has been introduced, or a non-naturally occurring glycosylation site has been introduced in combination with the removal of a natural occurring glycosylation site. The introduced glycosylation site can be an O-glycosylation site or an N-glycosylation site. Preferably the glycosylation site is an in vivo O-glycosylation site or an in vivo N-glycosylation site, in particular an in vivo N-glycosylation site.

When used in the present context, the term "naturally occurring glycosylation site" covers the glycosylation sites at postions N145, N322, S52 and S60. In a similar way, the term "naturally occurring in vivo O-glycosylation site" includes the positions S52 and S60, whereas the term "naturally occurring in vivo N-glycosylation site" includes positions N145 and N322.

Typically, the amino acid sequence of the FVII or FVIIa polypeptide differs from that shown in SEQ ID NO:1 in that at least one non-naturally occurring glycosylation site (e.g., at least one non-naturally occurring in vivo N-glycosylation site), such as 1-15 non-naturally occurring glycosylation sites (e.g., 1-15 non-naturally occurring in vivo N-glycosylation sites), in particular 1-10, 1-6 or 2-4 non-naturally occurring glycosylation sites (e.g., 1-10, 1-6 or 2-4 non-naturally occurring in vivo N-glycosylation sites), has been introduced, preferably by substitution.

It will be understood that in order to prepare a conjugate, wherein the polypeptide of the conjugate comprises one or more glycosylation sites, the polypeptide must be expressed in a host cell capable of attaching sugar (oligosaccharide) moieties at the glycosylation site(s) or alternatively subjected to in vitro glycosylation. Examples of glycosylating host cells are given in the section further below entitled "Coupling to a sugar moiety."

In an interesting embodiment of this aspect, an in vivo glycosylation site is introduced into a position of the parent FVII or FVIIa molecule occupied by an amino acid residue exposed to the surface of the molecule, preferably with more than 25% of the side chain exposed to the solvent, in particular more than 50% exposed to the solvent (these positions are identified in the Methods section herein). The N-glycosylation site is then introduced in such a way that the N-residue of said site is located in said position. Analogously, an O-glycosylation site is introduced so that the S or T residue making up such site is located in said position. Examples of such positions include K32S/T, I42S/T, Y44S/T, K143S/T, R290S/T, R315S/T, K341S/T, R392S/T, R396S/T, R402S/T and combinations thereof.

With respect to N-glycosylation, the in vivo glycosylation site is introduced into a position wherein only one mutation is required to create the site (i.e., where any other amino acid residues required for creating a functional glycosylation site is already present in the molecule).

In other words, the conjugate according to the invention is preferably a conjugate, wherein the amino acid sequence of the polypeptide differs from SEQ ID NO:1 in that at least one naturally occurring N-X'-X sequence is substituted with a N-X'-S or N-X'-T sequence, wherein X' is any amino acid except P, and X is any amino acid except for S and T.

In a similar way, the conjugate according to the invention is preferably a conjugate, wherein the amino acid sequence of the polypeptide differs from SEQ ID NO:1 in that at least one naturally occurring X-X'-S or X-X'-T sequence naturally present in SEQ ID NO:1 is substituted with a N-X'-S or a N-X'-T sequence, wherein X' is any amino acid except P, and X is any amino acid except for N.

Specific examples of such substitutions creating an in vivo N-glycosylation site include a substitution selected from the group consisting of F4S/T, P10N, Q21N, W41N, S43N, A51N, G58N, L65N, G59S/T, E82S/T, N95S/T, G97S/T, Y101N, D104N, T106N, K109N, G117N, G124N, S126N, T128N, A175S/T, G179N, I186S/T, V188N, R202S/T, I205S/T, D212N, E220N, I230N, P231N, P236N, G237N, V253N, E265N, T267N, E270N, R277N, L280N, G291N, P303S/T, L305N, Q312N, G318N, G331N, D334N, K337N, G342N, H348N, R353N, Y357N, I361N, V376N, R379N, M391N, and combinations thereof. Preferably, the substitution is selected from the group consisting of F4S/T, P10N, Q21N, W41N, A51N, G58N, G59S/T, N95S/T, G97S/T, Y101N, D104N, T106N, K109N, G117N, G124N, S126N, T128N, A175S/T, I186S/T, V188N, R202S/T, I205S/T, D212N, E220N, V253N, E265N, T267N, E270N, L280N, G291N, P303S/T, G318N, G331N, D334N, K337N, R353N, Y357N, M391N, and combinations thereof.

Alternatively, the in vivo glycosylation site is introduced in a position occupied by a lysine residue or an arginine residue, preferably occupied by an lysine residue, in particular so that the N-residue of the N-glycosylation site or the S or T residue of an O-glycosylation site substitutes the lysine residue.

Stated differently, the conjugate according to the invention is preferably a conjugate, wherein the amino acid sequence of the polypeptide differs from SEQ ID NO:1 in that at least one K-X'-X sequence or R-X'-X sequence, preferably a K-X'-X sequence, naturally present in SEQ ID NO:1 is substituted with a N-X'-S or a N-X'-T sequence, wherein X' is any amino acid except P, and X is any amino acid except for S and T.

Specific examples of such substitutions creating an in vivo N-glycosylation site include a substitution selected from the group consisting of K32N+A34S/T, K38N+F40S/T, K62N+Q64S/T, K85N+D87S/T, K137N+P139S/T, K143N+N145S/T, K148N+Q149S/T, K161N+E163S/T, K197N+K199S/T, K199N+W201S/T, K316N+G318S/T, K337N, K341N+D343S/T, K389N+M391S/T and combinations thereof.

In a further interesting embodiment of the glycosylation aspect described above, a glycosylation site, in particular an N-glycosylation site, can be introduced in positions at or in the vicinity of the proteolytic degradation sites described above (see the section entitled "Conjugate of the invention").

Thus, specific examples of such substitutions creating an in vivo N-glycosylation site include a substitution selected from the group consisting of K32N+A34S/T, F31N+D33S/T, I30N+K32S/T, A34N+R36S/T, K38N+F40S/T, T37N+ L39S/T, R36N+K38S/T, L39N+W41S/T, F40N+I42S/T, W41N, I42N+Y44S/T, S43N, Y44N+D46S/T, S45N+G47S/ T, D46N+D48S/T, G47N+Q49S/T, K143N+N145S/T, E142N+R144S/T, L141N+K143S/T, I140N+E142S/T, R144N+A146S/T, A146N+K148S/T, S147N+P149S/T, R290N+A292S/T, D289N+G291S/T, L288N+R290S/T, L287N+D289S/T, G291N, A292N+A294S/T, T293N+ L295S/T, R315N+V317S/T, S314N+K316S/T, Q313N+ R315S/T, Q312N, K316N+G318S/T, V317N+D319S/T, G318N, K341N+D343S/T, S339N+K341S/T, G342N, D343N+G345S/T, R392N+E394S/T, M391N, L390N+ R392S/T, K389N+M391S/T, S393N+P395S/T, E394N+ R396S/T, P395N+P397S/T, R396N+G398S/T, P397N+ V399S/T, G398N+L400S/T, V399N+L4011S/T, L400N+ R402S/T, L401N+A403S/T, R402N+P404S/T, A403N+ F405S/T, P404N+P406S/T and combinations thereof, such as K143N+N145S/T+R315N+V317S/T. Preferably, the substitution is selected from the group consisting of K32N+A34S/ T, K38N+F40S/T, Y44N+D46S/T, K143N+N145S/T, R290N+A292S/T, R315N+V317S/T, K341N+D343S/T, R392N+E394S/T, R396N+G398S/T, R402N+P404S/T and combinations thereof, such as K143N+N145S/T+R315N+ V317S/T. More preferably, the substitution is selected from the group consisting of K32N+A34T, K38N+F40T, Y44N+ D46T, K143N+N145T, R290N+A292T, R315N+V317T, 341N+D343T, R392N+E394T, R396N+G398T, R402N+ P404T and combinations thereof, in particular K143N+ N145T+R315N+V317T.

In a still further interesting embodiment of the invention, it is preferred that the in vivo glycosylation site is introduced in a position which does neither form part of the tissue factor binding nor form part of the active site region and the ridge of the active site binding cleft as defined herein. It is envisaged that such glycosylation variants will primarily belong to the class of active conjugates as defined hereinbefore.

Thus, specific examples of substitutions creating such an in vivo N-glycosylation site include substitutions selcted from the group consisting of K32N+A34S/T, I30N+K32S/T, A34N+R36S/T, K38N+F40S/T, T37N+L39S/T, W41N, Y44N+D46S/T, S45N+G47S/T, D46N+D48S/T, G47N+ Q49S/T, K143N+N145S/T, E142N+R144S/T, L141N+ K143S/T, I140N+E142S/T, R144N+A146S/T, A 146N+ K148S/T, S147N+P149S/T, L288N+R290S/T, L287N+ D289S/T, R315N+V317S/T, S314N+K316S/T, K316N+ G318S/T, V317N+D319S/T, G318N, R392N+E394S/T, M391N, L390N+R392S/T, K389N+M391S/T, S393N+ P395S/T, E394N+R396S/T, P395N+P397S/T, R396N+ G398S/T, P397N+V399S/T, G398N+L400S/T, V399N+ L401S/T, L401N+A403S/T, R402N+P404S/T, A403N+ F405S/T, P404N+P406S/T and combinations thereof, such as K143N+N145S/T+R315N+V317S/T. Preferably, the substitution is selected from the group consisting of K32N+A34S/ T, K38N+F40S/T, Y44N+D46S/T, K143N+N145S/T, R315N+V317S/T, R392N+E394S/T, R396N+G398S/T, R402N+P404S/T and combinations thereof, such as K143N+ N145S/T+R315N+V317S/T. More preferably, the substitution is selected from the group consisting of K32N+A34T, K38N+F40T, Y44N+D46T, K143N+N145T, R315N+ V317T, R392N+E394T, R396N+G398T, R402N+P404T and combinations thereof, in particular K143N+N145T+R315N+ V317T.

In an even further interesting embodiment of the invention, it is preferred that the in vivo glycosylation site is introduced in a position which does not form part of the tissue factor but which forms part of the active site region and the ridge of the active site binding cleft as defined herein. It is envisaged that such glycosylation variants will primarily belong to the class of inactive conjugates as defined hereinbefore.

Thus, specific examples of substitutions creating such an in vivo N-glycosylation site include substitutions selected from the group consisting of I153N+G155S/T, Q167N+L169S/T, V168N+L170S/T, L169N+L171S/T, L170N+V172S/T, L171N+N173S/T, A175S/T, A175N+L177S/T, L177N+G179S/T, G179N, G180N+L182S/T, T181N+I183S/T, V188N, V189N+A191S/T, S190N+A192S/T, A191N+H193S/T, H193N+F195S/T, F195N+K197S/T, D196N+I198S/T, K197N+K199S/T, I198N+N200S/T, K199N+W201S/T, W201N+N203S/T, R202S/T, I205S/T, V228N+I230S/T, I229N+P231S/T, I230N, P231N, S232N+Y234S/T, T233N+V235S/T, Y234N+P236S/T, V235N+G237S/T, P236N, G237N, T238N+N240S/T, T239N+H241S/T, H241N+I243S/T, D242S/T, I243N+L245S/T, A244N+L246S/T, L245N+R247S/T, L246N+L246S/T, V281N+G283S/T, S282N+W284S/T, G283N+G285S/T, W284N+Q286S/T, G285N+L287S/T, Q286N+L288S/T, D289N+G291S/T, R290N+A292S/T, G291N, A292N+A294S/T, T293N+L295S/T, P321N+I323S/T, T324N+Y326S/T, E325N+M327S/T, Y326N+F327S/T, F328N+A330S/T, S339N+K341S/T, K341N+D343S/T, G342N+S344S/T, D343N+G345S/T, S344N+G346S/T, G345N+P347S/T, P347N+A349S/T, H348N, L358N+G360S/T, T359N+I361S/T, G360N+V362S/T, I361N, V362N+W364S/T, S363N+G365S/T, W364N+Q366S/T, G365N+G367S/T, T370N+G372S/T, V376N, Y377N+R379S/T, T378N+V380S/T, R379N, V380N+Q382S/T, Q382N+I384S/T, Y383N+E385S/T, W386N+Q388S/T, L387N+K389S/T, L400N+R402S/T and combinations thereof. Preferably, the substitution is selected from the group consisting of D289N+G291S/T, R290N+A292S/T, G291N, A292N+A294S/T, T293N+L295S/T, S339N+K341S/T, K341N+D343S/T, G342N+S344S/T, D343N+G345S/T, and combinations thereof. More preferably, the substitution is selcted from the group consisting of D289N+G291T, R290N+A292T, G291N, A292N+A294T, T293N+L295T, S339N+K341T, K341N+D343T, G342N+S344T, D343N+G345T, and combinations thereof.

In addition to a sugar moiety, the conjugate according to the aspect of the invention described in the present section can contain additional non-polypeptide moieties, in particular a polymer molecule, as described in the present application, conjugated to one or more attachment groups present in the polypeptide part of the conjugate.

It will be understood that any of the amino acid changes, in particular substitutions, specified in this section can be combined with any of the amino acid changes, in particular substitutions, specified in the other sections herein disclosing specific amino acid changes.

For instance, any of the glycosylated variants disclosed in the present section having introduced and/or removed at least one glycosylation site, such as a variant comprising the substitutions R315N+V317T and/or K143N+N145T, can further be conjugated to a polymer molecule, such as PEG, or any other non-polypeptide moiety. For this purpose the conjugation can be achieved by use of attachment groups already present in the FVII or FVIIa polypeptide or attachment groups can have been introduced and/or removed, in particular such that a total of 1-6, in particular 3-4 or 1, 2, 3, 4, 5, or 6 attachment groups are available for conjugation.

Preferably, in a conjugate of the invention wherein the FVII or FVIIa polypeptide comprises two glycosylation sites, the number and molecular weight of the non-polypeptide moiety is chosen so as that the total molecular weight added by the non-polypeptide moiety is in the range of 5-25 kDa, such as in the range of 10-25 kDa, in particular about 5 kDa, about 12 kDa, about 15 kDa or about 20 kDa.

An Inactive Conjugate

The conjugates of the invention can be rendered inactive by removing at least one amino acid residue occupying a position selected from the group consisting of R152, I153, S344, D242 and H193 of SEQ ID NO:1. The removal can be effected by substitution or deletion of one or more of the above-identified amino acid residues. Preferably, the removal is effected by substitution, in particular by conservative substitution. Accordingly, the inactive FVII or FVIIa polypeptide used herein can comprise one or more of the following substitutions: R152X, I153X, S344X, D242X or H193X, wherein X is any amino acid residue, preferably one leading to a conservative substitution. For instance, the inactive FVII or FVIIa polypeptide comprises the mutations R152X, wherein X is any amino acid residue other than lysine (since lysine forms part of a protease cleavage site). Other examples of specific substitutions include I153A/V/L; S344T/AIG/Y; D242E/A and/or H193R/A.

Alternatively, an active FVII or FVIIa polypeptide can be rendered inactive by carbamylating the α-amino acid group I153 or by complexing the polypeptide to a serine proteinase inhibitor. A suitable serine inhibitor protein is, e.g., selected from the group consisting of an organophosphor compound, a sulfanylfluoride, a peptide halomethylketone, preferably a Dansyl-Phe-Pro-Arg chloromethylketone, Dansyl-Glu-Glu-Arg chlormethylketone, Dansyl-Phe-Phe-Arg chlormethylketone or a Phe-Phe-Arg chloromethylketone, or an azapeptide.

A conjugate can also be rendered inactive by introducing at least one glycosylation site in a position selected so that the subsequent glycosylation inactivates the conjugate.

As explained above in the last part of the section entitled "Conjugate of the invention wherein the non-polypeptide moiety is a sugar moiety" it is preferred that such glycosylation sites are introduced in a position which does not form part of the tissue factor but which forms part of the active site region and the ridge of the active site binding cleft as defined herein. Specific examples of preferred substitutions are given above in the section entitled "Conjugate of the invention wherein the non-polypeptide moiety is a sugar moiety".

Non-polypeptide Moiety of the Conjugate of the Invention

As indicated further above the non-polypeptide moiety of the conjugate of the invention is preferably selected from the group consisting of a polymer molecule, a lipophilic compound, a sugar moiety (by way of in vivo glycosylation) and an organic derivatizing agent. All of these agents can confer desirable properties to the polypeptide part of the conjugate, in particular increased functional in vivo half-life and/or increased plasma half-life. The polypeptide part of the conjugate is normally conjugated to only one type of non-polypeptide moiety, but can also be conjugated to two or more different types of non-polypeptide moieties, e.g., to a polymer molecule and a sugar moiety, to a lipophilic group and a sugar moiety, to an organic derivatizing agent and a sugar moiety, to a lipophilic group and a polymer molecule, etc. The conjugation to two or more different non-polypeptide moieties can be done simultaneous or sequentially.

Methods of Preparing a Conjugate of the Invention

In the following sections "Conjugation to a lipophilic compound," "Conjugation to a polymer molecule," "Conjugation to a sugar moiety" and "Conjugation to an organic derivatizing agent" conjugation to specific types of non-polypeptide moieties is described. In general, a polypeptide conjugate according to the invention can be produced by culturing an appropriate host cell under conditions conducive for the expression of the polypeptide, and recovering the polypeptide, wherein a) the polypeptide comprises at least one N- or O-glycosylation site and the host cell is a eukaryotic host cell capable of in vivo glycosylation, and/or b) the polypeptide is subjected to conjugation to a non-polypeptide moiety in vitro.

It will be understood that the conjugation should be designed so as to produce the optimal molecule with respect to the number of non-polypeptide moieties attached, the size and form of such molecules (e.g., whether they are linear or branched), and the attachment site(s) in the polypeptide. The molecular weight of the non-polypeptide moiety to be used can e.g., be chosen on the basis of the desired effect to be achieved. For instance, if the primary purpose of the conjugation is to achieve a conjugate having a high molecular weight (e.g., to reduce renal clearance) it is usually desirable to conjugate as few high molecular weight non-polypeptide moieties as possible to obtain the desired molecular weight. When a high degree of shielding is desirable this can be obtained by use of a sufficiently high number of low molecular weight non-polypeptide moieties (e.g., with a molecular weight of from about 300 Da to about 5 kDa, such as a molecular weight of from 300 Da to 2 kDa) to effectively shield all or most protease cleavage sites or other vulnerable sites of the polypeptide.

Conjugation to a Lipophilic Compound

The polypeptide and the lipophilic compound can be conjugated to each other, either directly or by use of a linker. The lipophilic compound can be a natural compound such as a saturated or unsaturated fatty acid, a fatty acid diketone, a terpene, a prostaglandin, a vitamine, a carotenoide or steroide, or a synthetic compound such as a carbon acid, an alcohol, an amine and sulphonic acid with one or more alkyl-, aryl-, alkenyl- or other multiple unsaturated compounds. The conjugation between the polypeptide and the lipophilic compound, optionally through a linker can be done according to methods known in the art, e.g., as described by Bodanszky in Peptide Synthesis, John Wiley, New York, 1976 and in WO 96/12505.

Conjugation to a Polymer Molecule, Including Conjugation of a Polymer Molecule to the N-terminal of the Polypeptide The polymer molecule to be coupled to the polypeptide can be any suitable polymer molecule, such as a natural or synthetic homo-polymer or hetero-polymer, typically with a molecular weight in the range of about 300-100,000 Da, such as about 500-20,000 Da, more preferably in the range of about 500-15,000 Da, even more preferably in the range of about 2-12 kDa, such as in the range of about 3-10 kDa. When the term "about" is used herein in connection with a certain molecular weight, the word "about" indicates an approximate average molecular weight and reflects the fact that there will normally be a certain molecular weight distribution in a given polymer preparation.

Examples of homo-polymers include a polyol (i.e., poly-OH), a polyamine (i.e., poly-$NH_2$) and a polycarboxylic acid (i.e., poly-COOH). A hetero-polymer is a polymer comprising different coupling groups, such as a hydroxyl group and an amine group.

Examples of suitable polymer molecules include polymer molecules selected from the group consisting of polyalkylene oxide (PAO), including polyalkylene glycol (PAG), such as polyethylene glycol (PEG) and polypropylene glycol (PPG), branched PEGs, poly-vinyl alcohol (PVA), poly-carboxylate, poly-(vinylpyrolidone), polyethylene-co-maleic acid anhydride, polystyrene-co-maleic acid anhydride, dextran, including carboxymethyl-dextran, or any other biopolymer suitable for reducing immunogenicity and/or increasing functional in vivo half-life and/or serum half-life. Another example of a polymer molecule is human albumin or another abundant plasma protein. Generally, polyalkylene glycol-derived polymers are biocompatible, non-toxic, non-antigenic, non-immunogenic, have various water solubility properties, and are easily excreted from living organisms.

PEG is the preferred polymer molecule, since it has only few reactive groups capable of cross-linking compared to, e.g., polysaccharides such as dextran. In particular, monofunctional PEG, e.g., methoxypolyethylene glycol (mPEG), is of interest since its coupling chemistry is relatively simple (only one reactive group is available for conjugating with attachment groups on the polypeptide). Consequently, the risk of cross-linking is eliminated, the resulting polypeptide conjugates are more homogeneous and the reaction of the polymer molecules with the polypeptide is easier to control.

To effect covalent attachment of the polymer molecule(s) to the polypeptide, the hydroxyl end groups of the polymer molecule must be provided in activated form, i.e., with reactive functional groups (examples of which include primary amino groups, hydrazide (HZ), thiol, succinate (SUC), succinimidyl succinate (SS), succinimidyl succinamide (SSA), succinimidyl proprionate (SPA), succinimidy carboxymethylate (SCM), benzotriazole carbonate (BTC), N-hydroxysuccinimide (NHS), aldehyde, nitrophenylcarbonate (NPC), and tresylate (TRES)). Suitable activated polymer molecules are commercially available, e.g., from Shearwater Polymers, Inc., Huntsville, Ala., USA, or from PolyMASC Pharmaceuticals plc, UK.

Alternatively, the polymer molecules can be activated by conventional methods known in the art, e.g., as disclosed in WO 90/13540. Specific examples of activated linear or branched polymer molecules for use in the present invention are described in the Shearwater Polymers, Inc. 1997 and 2000 Catalogs (Functionalized Biocompatible Polymers for Research and pharmaceuticals, Polyethylene Glycol and Derivatives, incorporated herein by reference).

Specific examples of activated PEG polymers include the following linear PEGs: NHS-PEG (e.g., SPA-PEG, SSPA-PEG, SBA-PEG, SS-PEG, SSA-PEG, SC-PEG, SG-PEG, and SCM-PEG), and NOR-PEG, BTC-PEG, EPOX-PEG, NCO-PEG, NPC-PEG, CDI-PEG, ALD-PEG, TRES-PEG, VS-PEG, IODO-PEG, and MAL-PEG, and branched PEGs such as PEG2-NHS and those disclosed in U.S. Pat. No. 5,932,462 and U.S. Pat. No. 5,643,575, both of which are incorporated herein by reference. Furthermore, the following publications, incorporated herein by reference, disclose useful polymer molecules and/or PEGylation chemistries: U.S. Pat. No. 5,824,778, U.S. Pat. No. 5,476,653, WO 97/32607, EP 229,108, EP 402,378, U.S. Pat. No. 4,902,502, U.S. Pat. No. 5,281,698, U.S. Pat. No. 5,122,614, U.S. Pat. No. 5,219,564, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, U.S. Pat. No. 5,736,625, WO 98/05363, EP 809 996, U.S. Pat. No. 5,629,384, WO 96/41813, WO 96/07670, U.S. Pat. No. 5,473,034, U.S. Pat. No. 5,516,673, EP 605 963, U.S. Pat. No. 5,382,657, EP 510 356, EP 400 472, EP 183 503 and EP 154 316.

The conjugation of the polypeptide and the activated polymer molecules is conducted by use of any conventional method, e.g., as described in the following references (which also describe suitable methods for activation of polymer molecules): R. F. Taylor, (1991), "Protein immobilisation. Fundamental and applications," Marcel Dekker, N.Y.; S. S. Wong, (1992), "Chemistry of Protein Conjugation and Crosslinking," CRC Press, Florida, USA; G. T. Hermanson et al., (1993), "Immobilized Affinity Ligand Techniques," Academic Press, N.Y.). The skilled person will be aware that the activation method and/or conjugation chemistry to be used depends on the attachment group(s) of the polypeptide (examples of which are given further above), as well as the functional groups of the polymer (e.g., being amine, hydroxyl, carboxyl, aldehyde, sulfydryl, succinimidyl, maleimide, vinysulfone or haloacetate). The PEGylation can be directed towards conjugation to all available attachment groups on the polypeptide (i.e., such attachment groups that are exposed at the surface of the polypeptide) or can be directed towards one or more specific attachment groups, e.g., the N-terminal amino group as described in U.S. Pat. No. 5,985,265. Furthermore, the conjugation can be achieved in one step or in a stepwise manner (e.g., as described in WO 99/55377).

It will be understood that the PEGylation is designed so as to produce the optimal molecule with respect to the number of PEG molecules attached, the size and form of such molecules (e.g., whether they are linear or branched), and the attachment site(s) in the polypeptide. The molecular weight of the polymer to be used can e.g., be chosen on the basis of the desired effect to be achieved. For instance, if the primary purpose of the conjugation is to achieve a conjugate having a high molecular weight (e.g., to reduce renal clearance) it is usually desirable to conjugate as few high molecular weight polymer molecules as possible to obtain the desired molecular weight. When a high degree of shielding is desirable this can be obtained by use of a sufficiently high number of low molecular weight polymer molecules (e.g., with a molecular weight of from about 300 Da to about 5 kDa) to effectively shield all or most protease cleavage sites or other vulnerable sites of the polypeptide. For instance, 2-8, such as 3-6 such polymers can be used.

In connection with conjugation to only a single attachment group on the protein (e.g., the N-terminal amino group), it can be advantageous that the polymer molecule, which can be linear or branched, has a high molecular weight, preferably about 10-25 kDa, such as about 15-25 kDa, e.g., about 20 kDa.

Normally, the polymer conjugation is performed under conditions aimed at reacting as many of the available polymer attachment groups with polymer molecules. This is achieved by means of a suitable molar excess of the polymer relative to the polypeptide. Typically, the molar ratios of activated polymer molecules to polypeptide are up to about 1000-1, such as up to about 200-1, or up to about 100-1. In some cases the ration can be somewhat lower, however, such as up to about 50-1, 10-1 or 5-1 in order to obtain optimal reaction.

It is also contemplated according to the invention to couple the polymer molecules to the polypeptide through a linker. Suitable linkers are well known to the skilled person. A preferred example is cyanuric chloride (Abuchowski et al., (1977), J. Biol. Chem., 252, 3578-3581; U.S. Pat. No. 4,179, 337; Shafer et al., (1986), J. Polym. Sci. Polym. Chem. Ed., 24, 375-378).

Subsequent to the conjugation, residual activated polymer molecules are blocked according to methods known in the art, e.g., by addition of primary amine to the reaction mixture, and the resulting inactivated polymer molecules are removed by a suitable method.

It will be understood that depending on the circumstances, e.g., the amino acid sequence of the polypeptide, the nature of the activated PEG compound being used and the specific PEGylation conditions, including the molar ratio of PEG to polypeptide, varying degrees of PEGylation can be obtained, with a higher degree of PEGylation generally being obtained with a higher ratio of PEG to polypeptide. The PEGylated polypeptides resulting from any given PEGylation process will, however, normally comprise a stochastic distribution of polypeptide conjugates having slightly different degrees of PEGylation.

In an interesting embodiment of the invention, the polypeptide conjugate of the invention comprises a polymer molecule covalently attached to the A1 N-terminal of the wild type FVII or FVIIa polypeptide shown in SEQ ID NO:1, where said polymer molecule is the only polymer molecule attached to the polypeptide. Preferably, such polypeptide conjugates are ones, which comprise a single PEG molecule attached to the N-terminal of the polypeptide and no other PEG molecules. In particular, a linear or branched PEG molecule with a molecular weight of at least about 5 kDa, in particular about 10-25 kDa, such as about 15-25 kDa, e.g., about 20 kDa is preferred. The polypeptide conjugate according to this embodiment can further comprise one or more sugar moieties attached to an N-linked or O-linked glycosylation site of the polypeptide or sugar moieties attached by in vitro glycosylation.

In a further interesting embodiment of the invention the polypeptide conjugate of the invention comprises polymer molecules covalently attached to the A1 N-terminal and to the I153 N-terminal of the wild type FVIIa polypeptide shown in SEQ ID NO:1, where said polymer molecules are the only polymer molecules attached to the polypeptide. Preferably, such polypeptide conjugates are ones, which comprise a PEG molecule attached to both of the N-terminals of FVIIa and no other PEG molecules. In particular, linear or branched PEG molecules with a molecular weight of at least about 5 kDa, in particular about 10-25 kDa, such as about 15-25 kDa, e.g., about 20 kDa are preferred. The polypeptide conjugate according to this embodiment can further comprise one or more sugar moieties attached to an N-linked or O-linked glycosylation site of the polypeptide or sugar moieties attached by in vitro glycosylation.

One preferred method for selectively coupling polymer molecules, such as PEG molecules, to the N-terminal of the polypeptide is the method disclosed in U.S. Pat. No. 5,985, 265. This method involves reductive alkylation (reaction of the N-terminal amino group of the polypeptide with an aldehyde-containing polypeptide, such as aldehylde-PEG, in the presence of a reducing agent, such as $NaCNBH_3$). This method exploits differential reactivity of different types of primary amino groups (lysine versus N-terminal) available for derivatization in the polypeptide, thereby achieving substantially selective derivatization of the polypeptide at the N-terminus with a carbonyl group-containing polymer molecule, such as aldehyde-PEG. The reaction is performed at a pH which allows one to take advantage of the $pK_a$ differences between the ε-amino groups of the lysine residues and that of the α-amino group of the N-terminal residue of the polypeptide. In order to achieve this differential reactivity, the reaction is typically carried at slightly acidic conditions. Specific examples of suitable pH ranges include pH 4.5-7, such as pH 4.5-6, e.g., pH 5-6, in particular about pH 5.

In another specific embodiment, the polypeptide conjugate of the invention comprises a PEG molecule attached to each of the lysine residues in the polypeptide available for PEGylation, in particular a linear or branched PEG molecule, e.g., with a molecular weight of about 1-15 kDa, typically about 2-12 kDa, such as about 3-10 kDa, e.g., about 5 or 6 kDa.

In yet another embodiment, the polypeptide conjugate of the invention comprises a PEG molecule attached to each of the lysine residues in the polypeptide available for PEGylation, and in addition to the N-terminal amino acid residue of the polypeptide.

Covalent in vitro coupling of carbohydrate moieties (such as dextran) to amino acid residues of the polypeptide can also be used, e.g., as described, for example in WO 87/05330 and in Aplin etl al., CRC Crit Rev. Biochem, pp. 259-306, 1981. The in vitro coupling of carbohydrate moieties or PEG to protein- and peptide-bound Gln-residues can be carried out by transglutaminases (TGases). Transglutaminases catalyse the transfer of donor amine-groups to protein- and peptide-bound Gln-residues in a so-called cross-linking reaction. The donor-amine groups can be protein- or peptide-bound, such as the ε-amino-group in Lys-residues or it can be part of a small or large organic molecule. An example of a small organic molecule functioning as amino-donor in TGase-catalysed cross-linking is putrescine (1,4-diaminobutane). An example of a larger organic molecule functioning as amino-donor in TGase-catalysed cross-linking is an amine-containing PEG (Sato et al., 1996, Biochemistry 35, 13072-13080).

TGases, in general, are highly specific enzymes, and not every Gln-residues exposed on the surface of a protein is accessible to TGase-catalysed cross-linking to amino-containing substances. On the contrary, only few Gln-residues are naturally functioning as TGase substrates but the exact parameters governing which Gln-residues are good TGase substrates remain unknown. Thus, in order to render a protein susceptible to TGase-catalysed cross-linking reactions it is often a prerequisite at convenient positions to add stretches of amino acid sequence known to function very well as TGase substrates. Several amino acid sequences are known to be or to contain excellent natural TGase substrates e.g., substance P, elafin, fibrinogen, fibronectin, $\alpha_2$-plasmin inhibitor, α-caseins, and β-caseins.

Coupling to a Sugar Moiety

In order to achieve in vivo glycosylation of a FVII molecule comprising one or more glycosylation sites the nucleotide sequence encoding the polypeptide must be inserted in a glycosylating, eucaryotic expression host. The expression host cell can be selected from fungal (filamentous fungal or yeast), insect or animal cells or from transgenic plant cells. In one embodiment, the host cell is a mammalian cell, such as a CHO cell, BHK or HEK, e.g., HEK 293, cell, or an insect cell, such as an SF9 cell, or a yeast cell, e.g., *S. cerevisiae* or *Pichia pastoris*, or any of the host cells mentioned hereinafter.

Coupling to an Organic Derivatizing Agent

Covalent modification of the polypeptide can be performed by reacting one or more attachment groups of the polypeptide with an organic derivatizing agent. Suitable derivatizing agents and methods are well known in the art. For example, cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(4-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. Histidyl residues are derivatized by reaction with diethylpyrocarbonate at pH 5.5-7.0 because this agent is relatively specific for the histidyl side chain. Para-bromophenacyl bromide also is useful. The reaction is preferably performed in 0.1 M sodium cacodylate at pH 6.0. Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione and transaminase-catalyzed reaction with glyoxylate. Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group.

Furthermore, these reagents can react with the groups of lysine as well as the arginine guanidino group. Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Blocking of Functional Site

It has been reported that excessive polymer conjugation can lead to a loss of activity of the polypeptide to which the non-polypeptide moiety is conjugated. This problem can be eliminated, e.g., by removal of attachment groups located at the functional site or by reversible blocking the functional site prior to conjugation so that the functional site is blocked during conjugation. The latter strategy constitutes further embodiments of the invention (the first strategy being exemplified further above, e.g., by removal of lysine residues which can be located close to the functional site). More specifically, according to the second strategy the conjugation between the polypeptide and the non-polypeptide moiety is conducted under conditions where the functional site of the polypeptide is blocked by a helper molecule e.g., tissue factor capable of binding to the functional site of the polypeptide or a serine protease inhibitor.

Preferably, the helper molecule is one, which specifically recognizes a functional site of the polypeptide, such as a receptor, in particular tissue factor, either full length or a suitably truncated form of tissue factor or two molecules, one being tissue factor the other one being a peptide or peptide inhibitor binding to and thus protecting the area around the catalytic triad (preferably defined as amino acid residues within 10 Å of any atom in the catalytic triad).

Alternatively, the helper molecule can be an antibody, in particular a monoclonal antibody recognizing the FVII polypeptide. In particular, the helper molecule can be a neutralizing monoclonal antibody.

The polypeptide is allowed to interact with the helper molecule before effecting conjugation. This ensures that the functional site of the polypeptide is shielded or protected and consequently unavailable for derivatization by the non-polypeptide moiety such, as a polymer. Following its elution from the helper molecule, the conjugate between the non-polypeptide moiety and the polypeptide can be recovered with at least a partially preserved functional site.

The subsequent conjugation of the polypeptide having a blocked functional site to a polymer, a lipophilic compound, a sugar moiety, an organic derivatizing agent or any other compound is conducted in the normal way, e.g., as described in the sections above entitled "Conjugation to . . . ".

Irrespectively of the nature of the helper molecule to be used to shield the functional site of the polypeptide from conjugation, it is desirable that the helper molecule is free from or comprises only few attachment groups for the non-polypeptide moiety of choice in part(s) of the molecule, where the conjugation to such groups will hamper the desorption of the conjugated polypeptide from the helper molecule. Hereby, selective conjugation to attachment groups present in non-shielded parts of the polypeptide can be obtained and it is possible to reuse the helper molecule for repeated cycles of conjugation. For instance, if the non-polypeptide moiety is a polymer molecule such as PEG, which has the epsilon amino group of a lysine or N-terminal amino acid residue as an attachment group, it is desirable that the helper molecule is substantially free from conjugatable epsilon amino groups, preferably free from any epsilon amino groups. Accordingly, in a preferred embodiment, the helper molecule is a protein or peptide capable of binding to the functional site of the polypeptide, which protein or peptide is free from any conjugatable attachment groups for the non-polypeptide moiety of choice.

In a further embodiment, the helper molecule is first covalently linked to a solid phase such as column packing materials, for instance Sephadex or agarose beads, or a surface, e.g., reaction vessel. Subsequently, the polypeptide is loaded onto the column material carrying the helper molecule and conjugation carried out according to methods known in the art, e.g., as described in the sections above entitled "Conjugation to . . . " This procedure allows the polypeptide conjugate to be separated from the helper molecule by elution. The polypeptide conjugate is eluted by conventional techniques under physico-chemical conditions that do not lead to a substantive degradation of the polypeptide conjugate. The fluid phase containing the polypeptide conjugate is separated from the solid phase to which the helper molecule remains covalently linked. The separation can be achieved in other ways: For instance, the helper molecule can be derivatised with a second molecule (e.g., biotin) that can be recognized by a specific binder (e.g., streptavidin). The specific binder can be linked to a solid phase thereby allowing the separation of the polypeptide conjugate from the helper molecule-second molecule complex through passage over a second helper-solid phase column which will retain, upon subsequent elution, the helper molecule-second molecule complex, but not the polypeptide conjugate. The polypeptide conjugate can be released from the helper molecule in any appropriate fashion. Deprotection can be achieved by providing conditions in which the helper molecule dissociates from the functional site of the FVII to which it is bound. For instance, a complex between an antibody to which a polymer is conjugated and an anti-idiotypic antibody can be dissociated by adjusting the pH to an acid or alkaline pH. Even more preferred is the use of a conformation specific antibody that recognizes a $Ca^{2+}$ specific conformation of FVII and consequently can be eluted with EDTA under mild conditions.

Attachment of Serine Protease Inhibitor

Attachment of a serine protease inhibitor can be performed in accordance with the method described in WO 96/12800.

Conjugation of a Tagged Polypeptide

In an alternative embodiment, the polypeptide is expressed as a fusion protein with a tag, i.e., an amino acid sequence or peptide stretch made up of typically 1-30, such as 1-20 amino acid residues. Besides allowing for fast and easy purification, the tag is a convenient tool for achieving conjugation between the tagged polypeptide and the non-polypeptide moiety. In particular, the tag can be used for achieving conjugation in microtiter plates or other carriers, such as paramagnetic beads, to which the tagged polypeptide can be immobilised via the tag. The conjugation to the tagged polypeptide in, e.g.,
microtiter plates has the advantage that the tagged polypeptide can be immobilised in the microtiter plates directly from the culture broth (in principle without any purification) and subjected to conjugation. Thereby, the total number of process steps (from expression to conjugation) can be reduced. Furthermore, the tag can function as a spacer molecule, ensuring an improved accessibility to the immobilised polypeptide to be conjugated. The conjugation using a tagged polypeptide can be to any of the non-polypeptide moieties disclosed herein, e.g., to a polymer molecule such as PEG.

The identity of the specific tag to be used is not critical as long as the tag is capable of being expressed with the polypeptide and is capable of being immobilised on a suitable surface or carrier material. A number of suitable tags are commercially available, e.g., from Unizyme Laboratories, Denmark. For instance, the tag can consist of any of the following sequences:

```
His-His-His-His-His-His

Met-Lys-His-His-His-His-His-His

Met-Lys-His-His-Ala-His-His-Gln-His-His

Met-Lys-His-Gln-His-Gln-His-Gln-His-Gln-His-Gln-
His-Gln

Met-Lys-His-Gln-His-Gln-His-Gln-His-Gln-His-Gln-
His-Gln-Gln
``` or any of the following:

```
EQKLISEEDL
(a C-terminal tag described in Mol. Cell. Biol.
5:3610-16, 1985)

DYKDDDDK
(a C- or N-terminal tag)

YPYDVPDYA
```

Antibodies against the above tags are commercially available, e.g., from ADI, Aves Lab and Research Diagnostics.

The subsequent cleavage of the tag from the polypeptide can be achieved by use of commercially available enzymes.

Methods of Preparing a Polypeptide of the Invention or the Polypeptide of the Conjugate of the Invention The polypeptide of the present invention or the polypeptide part of a conjugate of the invention, optionally in glycosylated form, can be produced by any suitable method known in the art. Such methods include constructing a nucleotide sequence encoding the polypeptide and expressing the sequence in a suitable transformed or transfected host. Preferably, the host cell is a gammacarboxylating host cell such as a mammalian cell. However, polypeptides of the invention can be produced, albeit less efficiently, by chemical synthesis or a combination of chemical synthesis or a combination of chemical synthesis and recombinant DNA technology.

A nucleotide sequence encoding a polypeptide or the polypeptide part of a conjugate of the invention can be constructed by isolating or synthesizing a nucleotide sequence encoding the parent FVII, such as hFVII with the amino acid sequence shown in SEQ ID NO:1 and then changing the nucleotide sequence so as to effect introduction (i.e., insertion or substitution) or removal (i.e., deletion or substitution) of the relevant amino acid residue(s).

The nucleotide sequence is conveniently modified by site-directed mutagenesis in accordance with conventional methods. Alternatively, the nucleotide sequence is prepared by chemical synthesis, e.g., by using an oligonucleotide synthesizer, wherein oligonucleotides are designed based on the amino acid sequence of the desired polypeptide, and preferably selecting those codons that are favored in the host cell in which the recombinant polypeptide will be produced. For example, several small oligonucleotides coding for portions of the desired polypeptide can be synthesized and assembled by PCR, ligation or ligation chain reaction (LCR) (Barany, PNAS 88:189-193, 1991). The individual oligonucleotides typically contain 5' or 3' overhangs for complementary assembly.

Alternative nucleotide sequence modification methods are available for producing polypeptide variants for high throughput screening, for instance methods which involve homologous cross-over such as disclosed in U.S. Pat. No. 5,093,257, and methods which involve gene shuffling, i.e., recombination between two or more homologous nucleotide sequences resulting in new nucleotide sequences having a number of nucleotide alterations when compared to the starting nucleotide sequences. Gene shuffling (also known as DNA shuffling) involves one or more cycles of random fragmentation and reassembly of the nucleotide sequences, followed by screening to select nucleotide sequences encoding polypeptides with desired properties. In order for homology-based nucleic acid shuffling to take place, the relevant parts of the nucleotide sequences are preferably at least 50% identical, such as at least 60% identical, more preferably at least 70% identical, such as at least 80% identical. The recombination can be performed in vitro or in vivo.

Examples of suitable in vitro gene shuffling methods are disclosed by Stemmer et al. (1994), Proc. Natl. Acad. Sci. USA; vol. 91, pp. 10747-10751; Stemmer (1994), Nature, vol. 370, pp. 389-391; Smith (1994), Nature vol. 370, pp. 324-325; Zhao et al., Nat. Biotechnol. 1998, March; 16(3): 258-61; Zhao H. and Arnold, F B, Nucleic Acids Research, 1997, Vol. 25. No. 6 pp. 1307-1308; Shao et al., Nucleic Acids Research 1998, Jan. 15; 26(2): pp. 681-83; and WO 95/17413.

An example of a suitable in vivo shuffling method is disclosed in WO 97/07205. Other techniques for mutagenesis of nucleic acid sequences by in vitro or in vivo recombination are disclosed e.g., in WO 97/20078 and U.S. Pat. No. 5,837,458. Examples of specific shuffling techniques include "family shuffling," "synthetic shuffling" and "in silico shuffling".

Family shuffling involves subjecting a family of homologous genes from different species to one or more cycles of shuffling and subsequent screening or selection. Family shuffling techniques are disclosed e.g., by Crameri et al. (1998), Nature, vol. 391, pp. 288-291; Christians et al. (1999), Nature Biotechnology, vol. 17, pp. 259-264; Chang et al. (1999), Nature Biotechnology, vol. 17, pp. 793-797; and Ness et al. (1999), Nature Biotechnology, vol. 17, 893-896.

Synthetic shuffling involves providing libraries of overlapping synthetic oligonucleotides based e.g., on a sequence alignment of homologous genes of interest. The synthetically generated oligonucleotides are recombined, and the resulting recombinant nucleic acid sequences are screened and if desired used for further shuffling cycles. Synthetic shuffling techniques are disclosed in WO 00/42561.

In silico shuffling refers to a DNA shuffling procedure, which is performed or modelled using a computer system, thereby partly or entirely avoiding the need for physically manipulating nucleic acids. Techniques for in silico shuffling are disclosed in WO 00/42560.

Once assembled (by synthesis, site-directed mutagenesis or another method), the nucleotide sequence encoding the polypeptide is inserted into a recombinant vector and operably linked to control sequences necessary for expression of the FVII in the desired transformed host cell.

It should of course be understood that not all vectors and expression control sequences function equally well to express the nucleotide sequence encoding a polypeptide described herein. Neither will all hosts function equally well with the same expression system. However, one of skill in the art can make a selection among these vectors, expression control sequences and hosts without undue experimentation. For example, in selecting a vector, the host must be considered because the vector must replicate in it or be able to integrate into the chromosome. The vector's copy number, the ability to control that copy number, and the expression of any other proteins encoded by the vector, such as antibiotic markers, should also be considered. In selecting an expression control sequence, a variety of factors should also be considered. These include, for example, the relative strength of the sequence, its controllability, and its compatibility with the nucleotide sequence encoding the polypeptide, particularly as regards potential secondary structures. Hosts should be selected by consideration of their compatibility with the chosen vector, the toxicity of the product coded for by the nucleotide sequence, their secretion characteristics, their ability to fold the polypeptide correctly, their fermentation or culture requirements, and the ease of purification of the products coded for by the nucleotide sequence.

The recombinant vector can be an autonomously replicating vector, i.e., a vector, which exists as an extrachromosomal entity, the replication of which is independent of chromosomal replication, e.g., a plasmid. Alternatively, the vector is one which, when introduced into a host cell, is integrated into the host cell genome and replicated together with the chromosome(s) into which it has been integrated.

The vector is preferably an expression vector, in which the nucleotide sequence encoding the polypeptide of the invention is operably linked to additional segments required for transcription of the nucleotide sequence. The vector is typically derived from plasmid or viral DNA. A number of suitable expression vectors for expression in the host cells mentioned herein are commercially available or described in the literature. Useful expression vectors for eukaryotic hosts, include, for example, vectors comprising expression control sequences from SV40, bovine papilloma virus, adenovirus and cytomegalovirus. Specific vectors are, e.g., pcDNA3.1 (+)\Hyg (Invitrogen, Carlsbad, Calif., USA) and pCI-neo (Stratagene, La Jola, Calif., USA). Useful expression vectors for yeast cells include the 2μ plasmid and derivatives thereof, the POT1 vector (U.S. Pat. No. 4,931,373), the pJSO37 vector described in Okkels, Ann. New York Acad. Sci. 782, 202-207, 1996, and pPICZ A, B or C (Invitrogen). Useful vectors for insect cells include pVL941, pBG311 (Cate et al., "Isolation of the Bovine and Human Genes for Mullerian Inhibiting Substance And Expression of the Human Gene In Animal Cells," Cell, 45, pp. 685-98 (1986), pBluebac 4.5 and pMelbac (both available from Invitrogen). Useful expression vectors for bacterial hosts include known bacterial plasmids, such as plasmids from E. coli, including pBR322, pET3a and pET12a (both from Novagen Inc., WI, USA), wider host range plasmids, such as RP4, phage DNAs, e.g., the numerous derivatives of phage lambda, e.g., NM989, and other DNA phages, such as M13 and filamentous single stranded DNA phages.

Other vectors for use in this invention include those that allow the nucleotide sequence encoding the polypeptide to be amplified in copy number. Such amplifiable vectors are well known in the art. They include, for example, vectors able to be amplified by DHFR amplification (see, e.g., Kaufman, U.S.

Pat. No. 4,470,461, Kaufman and Sharp, "Construction of A Modular Dihydrafolate Reductase cDNA Gene: Analysis Of Signals Utilized For Efficient Expression," Mol. Cell. Biol., 2, pp. 1304-19 (1982)) and glutamine synthetase ("GS") amplification (see, e.g., U.S. Pat. No. 5,122,464 and EP 338, 841).

The recombinant vector can further comprise a DNA sequence enabling the vector to replicate in the host cell in question. An example of such a sequence (when the host cell is a mammalian cell) is the SV40 origin of replication. When the host cell is a yeast cell, suitable sequences enabling the vector to replicate are the yeast plasmid 2μ replication genes REP 1-3 and origin of replication.

The vector can also comprise a selectable marker, e.g., a gene the product of which complements a defect in the host cell, such as the gene coding for dihydrofolate reductase (DHFR) or the *Schizosaccharomyces pombe* TPI gene (described by P. R. Russell, Gene 40, 1985, pp. 125-130), or one which confers resistance to a drug, e.g., ampicillin, kanamycin, tetracyclin, chloramphenicol, neomycin, hygromycin or methotrexate. For *Saccharomyces cerevisiae*, selectable markers include ura3 and leu2. For filamentous fungi, selectable markers include amdS, pyrG, arcB, niaD and sC.

The term "control sequences" is defined herein to include all components, which are necessary or advantageous for the expression of the polypeptide of the invention. Each control sequence can be native or foreign to the nucleic acid sequence encoding the polypeptide. Such control sequences include, but are not limited to, a leader sequence, polyadenylation sequence, propeptide sequence, promoter, enhancer or upstream activating sequence, signal peptide sequence, and transcription terminator. At a minimum, the control sequences include a promoter.

A wide variety of expression control sequences can be used in the present invention. Such useful expression control sequences include the expression control sequences associated with structural genes of the foregoing expression vectors as well as any sequence known to control the expression of genes of prokaryotic or eukaryotic cells or their viruses, and various combinations thereof.

Examples of suitable control sequences for directing transcription in mammalian cells include the early and late promoters of SV40 and adenovirus, e.g., the adenovirus 2 major late promoter, the MT-1 (metallothionein gene) promoter, the human cytomegalovirus immediate-early gene promoter (CMV), the human elongation factor 1α (EF-1α) promoter, the *Drosophila* minimal heat shock protein 70 promoter, the Rous Sarcoma Virus (RSV) promoter, the human ubiquitin C (UbC) promoter, the human growth hormone terminator, SV40 or adenovirus Elb region polyadenylation signals and the Kozak consensus sequence (Kozak, M. *J Mol Biol* 1987 Aug. 20; 196(4):947-50).

In order to improve expression in mammalian cells a synthetic intron can be inserted in the 5' untranslated region of the nucleotide sequence encoding the polypeptide. An example of a synthetic intron is the synthetic intron from the plasmid pCI-Neo (available from Promega Corporation, WI, USA).

Examples of suitable control sequences for directing transcription in insect cells include the polyhedrin promoter, the P10 promoter, the *Autographa californica* polyhedrosis virus basic protein promoter, the baculovirus immediate early gene 1 promoter and the baculovirus 39K delayed-early gene promoter, and the SV40 polyadenylation sequence. Examples of suitable control sequences for use in yeast host cells include the promoters of the yeast α-mating system, the yeast triose phosphate isomerase (TPI) promoter, promoters from yeast glycolytic genes or alcohol dehydrogenase genes, the ADH2-4c promoter, and the inducible GAL promoter. Examples of suitable control sequences for use in filamentous fungal host cells include the ADH3 promoter and terminator, a promoter derived from the genes encoding *Aspergillus oryzae* TAKA amylase triose phosphate isomerase or alkaline protease, an *A. niger* α-amylase, *A. niger* or *A. nidulans* glucoamylase, *A. nidulans* acetamidase, *Rhizomucor miehei* aspartic proteinase or lipase, the TPI1 terminator and the ADH3 terminator. Examples of suitable control sequences for use in bacterial host cells include promoters of the lac system, the trp system, the TAC or TRC system, and the major promoter regions of phage lambda.

The presence or absence of a signal peptide will, e.g., depend on the expression host cell used for the production of the polypeptide to be expressed (whether it is an intracellular or extracellular polypeptide) and whether it is desirable to obtain secretion. For use in filamentous fungi, the signal peptide can conveniently be derived from a gene encoding an *Aspergillus* sp. amylase or glucoamylase, a gene encoding a *Rhizomucor miehei* lipase or protease or a *Humicola lanuginosa* lipase. The signal peptide is preferably derived from a gene encoding *A. oryzae* TAKA amylase, *A. niger* neutral α-amylase, *A. niger* acid-stable amylase, or *A. niger* glucoamylase. For use in insect cells, the signal peptide can conveniently be derived from an insect gene (cf. WO 90/05783), such as the *Lepidopteran manduca sexta* adipokinetic hormone precursor, (cf. U.S. Pat. No. 5,023,328), the honeybee meiittin (Invitrogen), ecdysteroid UDPglucosyl-transferase (egt) (Murphy et al., Protein Expression and Purification 4, 349-357 (1993) or human pancreatic lipase (hpl) (Methods in Enzymology 284, pp. 262-272, 1997). A preferred signal peptide for use in mammalian cells is that of hFVII or the murine Ig kappa light chain signal peptide (Coloma, M (1992) J. Imm. Methods 152:89-104). For use in yeast cells suitable signal peptides have been found to be the α-factor signal peptide from *S. cereviciae* (cf. U.S. Pat. No. 4,870,008), a modified carboxypeptidase signal peptide (cf. L. A. Valls et al., Cell 48, 1987, pp. 887-897), the yeast BAR1 signal peptide (cf. WO 87/02670), the yeast aspartic protease 3 (YAP3) signal peptide (cf. M. Egel-Mitani et al., Yeast 6, 1990, pp. 127-137), and the synthetic leader sequence TA57 (WO98/32867). For use in *E. coli* cells a suitable signal peptide have been found to be the signal peptide ompA (EP581821).

The nucleotide sequence of the invention encoding a FVII polypeptide, whether prepared by site-directed mutagenesis, synthesis, PCR or other methods, can optionally include a nucleotide sequence that encode a signal peptide. The signal peptide is present when the polypeptide is to be secreted from the cells in which it is expressed. Such signal peptide, if present, should be one recognized by the cell chosen for expression of the polypeptide. The signal peptide can be homologous (e.g., be that normally associated with hFVII) or heterologous (i.e., originating from another source than hFVII) to the polypeptide or can be homologous or heterologous to the host cell, i.e., be a signal peptide normally expressed from the host cell or one which is not normally expressed from the host cell. Accordingly, the signal peptide can be prokaryotic, e.g., derived from a bacterium such as *E. coli*, or eukaryotic, e.g., derived from a mammalian, or insect or yeast cell.

Any suitable host can be used to produce the polypeptide or polypeptide part of the conjugate of the invention, including bacteria, fungi (including yeasts), plant, insect, mammal, or other appropriate animal cells or cell lines, as well as transgenic animals or plants. Examples of bacterial host cells include grampositive bacteria such as strains of *Bacillus*, e.g.,

*B. brevis* or *B. subtilis*, *Pseudomonas* or *Streptomyces*, or gramnegative bacteria, such as strains of *E. coli*. The introduction of a vector into a bacterial host cell can, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278). Examples of suitable filamentous fungal host cells include strains of *Aspergillus*, e.g., *A. oryzae*, *A. niger*, or *A. nidulans*, *Fusarium* or *Trichoderma*. Fungal cells can be transformed by a process involving protoplast formation, transformation of the protoplasts, and regeneration of the cell wall in a manner known per se. Suitable procedures for transformation of *Aspergillus* host cells are described in EP 238 023 and U.S. Pat. No. 5,679,543. Suitable methods for transforming *Fusarium* species are described by Malardier et al., 1989, *Gene* 78: 147-156 and WO 96/00787. Examples of suitable yeast host cells include strains of *Saccharomyces*, e.g., *S. cerevisiae*, *Schizosaccharomyces*, *Klyveromyces*, *Pichia*, such as *P. pastoris* or *P. methanolica*, *Hansenula*, such as *H. Polymorpha* or *Yarrowia*. Yeast can be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; Hinnen et al., 1978, *Proceedings of the National Academy of Sciences USA* 75: 1920: and as disclosed by Clontech Laboratories, Inc, Palo Alto, Calif., USA (in the product protocol for the Yeastmaker™ Yeast Transformation System Kit). Examples of suitable insect host cells include a *Lepidoptora* cell line, such as *Spodoptera frugiperda* (Sf9 or Sf21) or *Trichoplusioa ni* cells (High Five) (U.S. Pat. No. 5,077,214). Transformation of insect cells and production of heterologous polypeptides therein can be performed as described by Invitrogen. Examples of suitable mammalian host cells include Chinese hamster ovary (CHO) cell lines, (e.g., CHO-K1; ATCC CCL-61), Green Monkey cell lines (COS) (e.g., COS 1 (ATCC CRL-1650), COS 7 (ATCC CRL-1651)); mouse cells (e.g., NS/O), Baby Hamster Kidney (BHK) cell lines (e.g., ATCC CRL-1632 or ATCC CCL-10), and human cells (e.g., HEK 293 (ATCC CRL-1573)), as well as plant cells in tissue culture. Additional suitable cell lines are known in the art and available from public depositories such as the American Type Culture Collection, Rockville, Md. Also, the mammalian cell, such as a CHO cell, can be modified to express sialyltransferase, e.g., 1,6-sialyltransferase, e.g., as described in U.S. Pat. No. 5,047,335, in order to provide improved glycosylation of the FVII or FVIIa polypeptide.

In order to increase secretion it can be of particular interest to produce the polypeptide of the invention together with an endoprotease, in particular a PACE (Paired basic amino acid converting enzyme) (e.g., as described in U.S. Pat. No. 5,986, 079), such as a Kex2 endoprotease (e.g., as described in WO 00/28065).

Methods for introducing exogeneous DNA into mammalian host cells include calcium phosphate-mediated transfection, electroporation, DEAE-dextran mediated transfection, liposome-mediated transfection, viral vectors and the transfection method described by Life Technologies Ltd, Paisley, UK using Lipofectamin 2000. These methods are well known in the art and e.g., described by Ausbel et al. (eds.), 1996, Current Protocols in Molecular Biology, John Wiley & Sons, New York, USA. The cultivation of mammalian cells are conducted according to established methods, e.g., as disclosed in (Animal Cell Biotechnology, Methods and Protocols, Edited by Nigel Jenkins, 1999, Human Press Inc, Totowa, N.J., USA and Harrison M A and Rae I F, General Techniques of Cell Culture, Cambridge University Press 1997).

In the production methods of the present invention, the cells are cultivated in a nutrient medium suitable for production of the polypeptide using methods known in the art. For example, the cell can be cultivated by shake flask cultivation, small-scale or large-scale fermentation (including continuous, batch, fed-batch, or solid state fermentations) in laboratory or industrial fermenters performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or can be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The resulting polypeptide can be recovered by methods known in the art. For example, the polypeptide can be recovered from the nutrient medium by conventional procedures including, but not limited to, centrifugation, filtration, extraction, spray drying, evaporation, or precipitation.

The polypeptides can be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Single chain FVII can be purified and activated to two-chain FVIIa by a number of methods as described in the literature (Broze and Majerus, 1980, J. Biol. Chem. 255: 1242-47 and Hedner and Kisiel, 1983, J. Clin. Invest. 71:1836-41). Another method whereby single chain FVII can be purified is by incorporation of Zn ions during purification as described in U.S. Pat. No. 5,700,914.

In a preferred embodiment, the polypeptide is purified as a single chain FVII, which further is PEGylated. The PEGylated FVII single chain polypeptide is activated by either use of an immobilized enzyme (e.g., factors IIa, IXa, Xa and XIIa) or by autoactivation using a positively charged ion exchange matrix or the like.

It is advantageous to first purify FVII in its single chain form, then PEGylate (if desired) and last activate by one of the methods described above or by autoactivation as described by Pedersen et al, 1989, Biochemistry 28: 9331-36. The advantage of carrying out PEGylation before activation is that PEGylation of the new aminoterminal formed by cleavage of R152-I153 is avoided. PEGylation of this new amino terminal would render the molecule inactive since the formation of a hydrogen bond between D242 and the amino terminal of I153 is necessary for activity.

Pharmaceutical Composition of the Invention and its Use

In a further aspect, the present invention relates to a composition, in particular to a pharmaceutical composition, comprising a polypeptide or conjugate (including an inactive conjugate as described further above) of the invention and a pharmaceutically acceptable carrier or excipient.

The conjugate, the polypeptide or the pharmaceutical composition according to the invention can be used as a medicament.

Preferably, the polypeptide or the (active) conjugate can be used for the manufacture of a medicament for the treatment or prophylaxis of a FVIIa/TF-related disease or disorder in a mammal. For example, the polypeptide or the (active) conjugate can be used for the manufacture of a medicament for the treatment or prophylaxis of diseases wherein increased clot formation is desirable, such as treatment of patients having diseases resulting in inadequate blood coagulation in response to damage to blood vessels. In particular, the polypeptide or the (active) conjugate can be used for the manufacture of a medicament for the treatment of hemophiliacs, hemophiliacs with inhibitors to FVIII and FIX, patients with thrombocytopenia, patients with thrombocytopathies, such as Glanzmann's thrombastenia platelet release defects and storage pool defects, patients with von Willebrand's disease, patients with liver diseases, or otherwise healthy people with severe bleeding problems, e.g., due to trauma or major surgery, who have developed inhibitors to FVIIa, bleeding disorders such as hemophiliacs and other typically associated with severe tissue damages.

Analogously, the inactive conjugate of the invention can be used for the manufacture of a medicament for the treatment or prophylaxis of a FVIIa/TF-related disease or disorder in a mammal. For example, the inactive conjugate of the invention can be used for the manufacture of a medicament for the treatment or prophylaxis of diseases where decreased clot formation is desirable, such as prophylaxis or treatment of patients being in hypercoagulable states, such as patients with sepsis, deep-vein thrombosis, patients in risk of myocardial infections or thrombotic stroke, pulmonary embolism, patients with acute coronary syndromes (myocardial infarction and unstable angina pectoris), patients undergoing coronary cardiac, prevention of cardiac events and restonosis for patients receiving angioplasty, patients with peripheral vascular diseases. The inactive conjugate of the invention can also be used for the manufacture of a medicament for the treatment of respiratory diseases, tumor growth and metastasis.

In another aspect, the polypeptide, the (active) conjugate or the pharmaceutical composition comprising the (active) conjugate of the invention can be used in a method for treating a mammal having a FVIIa/TF-related disease or disorder (such as one or more of the diseases or disorders mentioned above), comprising administering to a mammal in need thereof an effective amount of such a polypeptide, conjugate or composition.

Analogously, the inactive conjugate or the pharmaceutical composition comprising the inactive conjugate of the invention can be used in a method for treating a mammal having a FVIIa/TF-related disease or disorder (such as one or more of the diseases or disorders mentioned above), comprising administering to a mammal in need thereof an effective amount of such an inactivated conjugate or composition.

The polypeptides or conjugates of the invention is administered to patients in a therapeutically effective dose, normally one approximately paralleling that employed in therapy with rFVII such as NovoSeven®, or at higher dosage. By "therapeutically effective dose" herein is meant a dose that is sufficient to produce the desired effects in relation to the condition for which it is administered. The exact dose will depend on the circumstances, and will be ascertainable by one skilled in the art using known techniques. Normally, the dose should be capable of preventing or lessening the severity or spread of the condition or indication being treated. It will be apparent to those of skill in the art that an effective amount of a polypeptide, conjugate or composition of the invention depends, inter alia, upon the disease, the dose, the administration schedule, whether the polypeptide or conjugate or composition is administered alone or in conjunction with other therapeutic agents, the plasma half-life of the compositions, and the general health of the patient. Preferably, the polypeptide, conjugate, or composition of the invention is administered in an effective dose, in particular a dose which is sufficient to normalize the coagulation disorder.

The polypeptide or conjugate of the invention is preferably administered in a composition including a pharmaceutically acceptable carrier or excipient. "Pharmaceutically acceptable" means a carrier or excipient that does not cause any untoward effects in patients to whom it is administered. Such pharmaceutically acceptable carriers and excipients are well known in the art (see, for example, Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]).

The polypeptide or conjugate of the invention can be formulated into pharmaceutical compositions by well-known methods. Suitable formulations are described by Remington's Pharmaceutical Sciences by E. W. Martin (Mark Publ. Co., 16th Ed., 1980).

The polypeptide or conjugate of the invention can be used "as is" and/or in a salt form thereof. Suitable salts include, but are not limited to, salts with alkali metals or alkaline earth metals, such as sodium, potassium, calcium and magnesium, as well as e.g., zinc salts. These salts or complexes can be present as a crystalline and/or amorphous structure.

The pharmaceutical composition of the invention can be administered alone or in conjunction with other therapeutic agents. These agents can be incorporated as part of the same pharmaceutical composition or can be administered separately from the polypeptide or conjugate of the invention, either concurrently or in accordance with another treatment schedule. In addition, the polypeptide, conjugate or pharmaceutical composition of the invention can be used as an adjuvant to other therapies.

A "patient" for the purposes of the present invention includes both humans and other mammals. Thus the methods are applicable to both human therapy and veterinary applications.

The pharmaceutical composition of the polypeptide or conjugate of the invention can be formulated in a variety of forms, e.g., as a liquid, gel, lyophilized, or as a compressed solid. The preferred form will depend upon the particular indication being treated and will be apparent to one skilled in the art.

In particular, the pharmaceutical composition of the polypeptide or conjugate of the invention can be formulated in lyophilised or stable soluble form. The polypeptide or the conjugate can be lyophilised by a variety of procedures known in the art. A polypeptide or the conjugate can be a stable soluble form by the removal or shielding of proteolytic degradation sites. The advantage of obtaining a stable soluble preparation lies in easier handling for the patient and, in the case of emergencies, quicker action, which potentially can become life saving. The preferred form will depend upon the particular indication being treated and will be apparent to one of skill in the art.

The administration of the formulations of the present invention can be performed in a variety of ways, including, but not limited to, orally, subcutaneously, intravenously, intracerebrally, intranasally, transdermally, intraperitoneally, intramuscularly, intrapulmonary, vaginally, rectally, intraocularly, or in any other acceptable manner. The formulations can be administered continuously by infusion, although bolus injection is acceptable, using techniques well known in the art, such as pumps or implantation. In some instances the formulations can be directly applied as a solution or spray.

Parenterals

A preferred example of a pharmaceutical composition is a solution designed for parenteral administration. Although in many cases pharmaceutical solution formulations are provided in liquid form, appropriate for immediate use, such parenteral formulations can also be provided in frozen or in lyophilized form. In the former case, the composition must be thawed prior to use. The latter form is often used to enhance the stability of the active compound contained in the composition under a wider variety of storage conditions, as it is recognized by those skilled in the art that lyophilized preparations are generally more stable than their liquid counterparts. Such lyophilized preparations are reconstituted prior to use by the addition of one or more suitable pharmaceutically acceptable diluents such as sterile water for injection or sterile physiological saline solution.

In case of parenterals, they are prepared for storage as lyophilized formulations or aqueous solutions by mixing, as appropriate, the polypeptide having the desired degree of purity with one or more pharmaceutically acceptable carriers, excipients or stabilizers typically employed in the art (all of which are termed "excipients"), for example buffering agents, stabilizing agents, preservatives, isotonifiers, non-ionic surfactants or detergents, antioxidants and/or other miscellaneous additives.

Buffering agents help to maintain the pH in the range which approximates physiological conditions. They are typically present at a concentration ranging from about 2 mM to about 50 mM Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additional possibilities are phosphate buffers, histidine buffers and trimethylamine salts such as Tris.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur-containing reducing agents, such as urea, glutathione, thioctic acid, sodium thioglycolate, thioglycerol, α-monothioglycerol and sodium thiosulfate; low molecular weight polypeptides (i.e., <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on the active protein weight.

Preservatives are added to retard microbial growth, and are typically added in amounts of about 0.2%-1% (w/v). Suitable preservatives for use with the present invention include phenol, benzyl alcohol, meta-cresol, methyl paraben, propyl paraben, octadecyldimethylbenzyl ammonium chloride, benzalkonium halides (e.g., benzalkonium chloride, bromide or iodide), hexamethonium chloride, alkyl parabens such as methyl or propyl paraben, catechol, resorcinol, cyclohexanol and 3-pentanol.

Isotonicifiers are added to ensure isotonicity of liquid compositions and include polyhydric sugar alcohols, preferably trihydric or higher sugar alcohols, such as glycerin, erythritol, arabitol, xylitol, sorbitol and mannitol. Polyhydric alcohols can be present in an amount between 0.1% and 25% by weight, typically 1% to 5%, taking into account the relative amounts of the other ingredients.

Non-ionic surfactants or detergents (also known as "wetting agents") can be present to help solubilizing the therapeutic agent as well as to protect the therapeutic polypeptide against agitation-induced aggregation, which also permits the formulation to be exposed to shear surface stress without causing denaturation of the polypeptide. Suitable non-ionic surfactants include polysorbates (20, 80, etc.), polyoxamers (184, 188 etc.), Pluronic® polyols, polyoxyethylene sorbitan monoethers (Tween®-20, Tween®-80, etc.).

Additional miscellaneous excipients include bulking agents or fillers (e.g., starch), chelating agents (e.g., EDTA), antioxidants (e.g., ascorbic acid, methionine, vitamin E) and cosolvents.

The active ingredient can also be entrapped in microcapsules prepared, for example, by coascervation techniques or by interfacial polymerization, for example hydroxymethylcellulose, gelatin or poly-(methylmethacylate) microcapsules, in colloidal drug delivery systems (for example liposomes, albumin microspheres, microemulsions, nanoparticles and nanocapsules) or in macroemulsions. Such techniques are disclosed in Remington's Pharmaceutical Sciences, supra.

Parenteral formulations to be used for in vivo administration must be sterile. This is readily accomplished, for example, by filtration through sterile filtration membranes.

Sustained Release Preparations

Examples of sustained-release preparations include semipermeable matrices of solid hydrophobic polymers containing the polypeptide or conjugate, the matrices having a suitable form such as a film or microcapsules. Examples of sustained-release matrices include polyesters, hydrogels (for example, poly(2-hydroxyethyl-methacrylate) or poly(vinylalcohol)), polylactides, copolymers of L-glutamic acid and ethyl-L-glutamate, non-degradable ethylene-vinyl acetate, degradable lactic acid-glycolic acid copolymers such as the ProLease® technology or Lupron Depot® (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for long periods such as up to or over 100 days, certain hydrogels release proteins for shorter time periods. When encapsulated polypeptides remain in the body for a long time, they can denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

The invention is further described in the following non-limiting examples.

Materials and Methods

Methods Used to Determine the Amino Acids to be Modified

Accessible Surface Area (ASA)

The computer program Access (B. Lee and F. M. Richards, J. Mol. Biol. 55: 379-400 (1971)) version 2 (© 1983 Yale University) are used to compute the accessible surface area (ASA) of the individual atoms in the structure. This method typically uses a probe-size of 1.4 Å and defines the Accessible Surface Area (ASA) as the area formed by the center of the probe. Prior to this calculation all water molecules and all hydrogen atoms should be removed from the coordinate set, as should other atoms not directly related to the protein.

Fractional ASA of Side Chain

The fractional ASA of the side chain atoms is computed by division of the sum of the ASA of the atoms in the side chain with a value representing the ASA of the side chain atoms of that residue type in an extended Ala-x-Ala tripeptide (See Hubbard, Campbell & Thornton (1991) J. Mol. Biol. 220, 507-530). For this example the CA atom is regarded as a part of the side chain of Glycine residues but not for the remaining residues. The following table is used as standard 100% ASA for the side chain:

| | |
|---|---|
| Ala | 69.23 Å$^2$ |
| Arg | 200.35 Å$^2$ |
| Asn | 106.25 Å$^2$ |
| Asp | 102.06 Å$^2$ |
| Cys | 96.69 Å$^2$ |
| Gln | 140.58 Å$^2$ |
| Glu | 134.61 Å$^2$ |
| Gly | 32.28 Å$^2$ |
| His | 147.00 Å$^2$ |
| Ile | 137.91 Å$^2$ |
| Leu | 140.76 Å$^2$ |
| Lys | 162.50 Å$^2$ |
| Met | 156.08 Å$^2$ |
| Phe | 163.90 Å$^2$ |
| Pro | 119.65 Å$^2$ |
| Ser | 78.16 Å$^2$ |
| Thr | 101.67 Å$^2$ |
| Trp | 210.89 Å$^2$ |
| Tyr | 176.61 Å$^2$ |
| Val | 114.14 Å$^2$ |

Residues not detected in the structure are defined as having 100% exposure as they are thought to reside in flexible regions. The gamma-carboxy glutamic acids at positions 6, 7, 14, 16, 19, 20, 25, 26, 29 and 35 are all defined as being 100% exposed.

Determining Distances Between Atoms

The distance between atoms is most easily determined using molecular graphics software e.g., InsightII® v. 98.0, MSI INC.

Catalytic Site Region

The catalytic site region is defined as any residues having at least one atom within 10 Å of any atom in the catalytic triad (residues H193, D242, S344).

Determination of Tissue Factor Binding Site

The receptor-binding site is defined as comprising of all residues having their accessible surface area changed upon receptor binding. This is determined by at least two ASA calculations; one on the isolated ligand(s) in the ligand(s)/receptor(s) complex and one on the complete ligand(s)/receptor(s) complex.

Methods for Testing FVII and FVIIa Properties

Measurement of Functional In Vivo Half-Life

Measurement of in vivo biological half-life can be carried out in a number of ways as described in the literature. An example of an assay for the measurement of in vivo half-life of rFVIIa or variants thereof is described in FDA reference number 96-0597. Briefly, FVII clotting activities are measured in plasma drawn prior to and during a 24-hour period after administration of the conjugate, polypeptide or composition. The median apparent volume of distribution at steady state is measured and the median clearance determined.

Measurement of Reduced Sensitivity to Proteolytic Degradation

A composition containing the conjugate (100-750 µg/ml, preferably 600 µg/ml), 1.5 mg $Ca^{2+}$/ml (as calcium chloride), mannitol (30 mg/ml), polysorbate 80 (0.1 mg/ml), sodium chloride (3 mg/ml) and glycyl-glycine buffer (1.3 mg/ml, pH 5.5) is prepared.

A similar composition containing wild-type rFVIIa is prepared.

The initial clotting activity or, alternatively, the initial amidolytic activity is then determined as described in the section entitled "Method for measuring the clotting activity" or as described in the section entitled "Method of measuring low levels of catalytic activity" or "Method of measuring the catalytic activity."

The compositions are then incubated at 37° C. until the composition containing the wild-type rFVII has lost at least 25%, preferably at least 50%, of its initial clotting or amidolytic activity.

The clotting or amidolytic activity of the composition containing the conjugate of the invention is then measured.

The reduced sensitivity to proteolytic degradation of the conjugate of the invention as compared to wild-type rFVIIa is then expressed in percentage.

Alternative Methods for Measuring Reduced Sensitivity to Proteolytic Degradation Proteolytic degradation can be measured using the assay described in U.S. Pat. No. 5,580,560, Example 5, where proteolysis is autoproteolysis.

Furthermore, reduced proteolysis can be tested in an in vivo model using radiolabelled samples and comparing proteolysis of wild type and conjugates by withdrawing blood samples and subjecting these to SDS-PAGE and autoradiography.

Irrespectively of the assay used for determining proteolytic degradation, "reduced proteolytic degradation" is intended to mean a measurable reduction in cleavage compared to that obtained by non-conjugated wild type FVIIa as measured by gel scanning of Coomassie stained SDS-PAGE gels, HPLC or as measured by conserved catalytic activity in comparison to wild type using the chromogenic assay described below.

Determination of the Molecular Weight of rFVII and Conjugates thereof

The molecular weight of conjugated or unconjugated rFVII or conjugates thereof is determined by either SDS-PAGE, gel filtration, Western Blots, matrix assisted laser desorption mass spectrometry or equilibrium centrifugation, e.g., SDS-PAGE according to Laemmli, U.K., Nature Vol 227 (1970), pp. 680-85.

Method of Measuring Low Levels of Catalytic Activity

The amidolytic activity in dilute samples of FVII/FVIIa and fermentation liquid/conditioned medium can be determined using COASET® FVII (Chromogenix, Art. No 82 19 00). The amidolytic activity is determined in accordance with the manufacturer's instructions. Briefly, FX is present in surplus and converted to FXa by FVIIa at 37° C. The generated FXa then hydrolyses the chromogenic substrate S2765 (N-α-Cbo-D-Arg-Gly-Arg-pNA) resulting in liberation of the chromophoric molecule, para-nitro-anillin (pNA) absorbing light at wavelength 405 nm. The reaction is stopped by addition of acetic acid. The amount of FVII/FVIIa in the sample is determined by comparison to a standard curve prepared from FVIIa (ranging from 125 pg/ml to 1 ng/ml in assay buffer).

Method of Measuring the Catalytic Activity

The ability of the conjugates to cleave small peptide substrates can be measured using the chromogenic substrate S-2288 (D-Ile-Pro-Arg-p-nitroanilide). Recombinant FVIIa is diluted in 0.1 M Tris, 0.1 M NaCl, 5 mM $CaCl_2$, pH 8.3 containing 0.1% BSA. The reaction is started by addition of the S-2288 substrate to 1 mM and the absorption at 405 nm is measured after incubation for 30 min. at 37° C.

Method of Measuring the Clotting Activity

FVIIa activity is measured using a standard one-stage clotting assay essentially as described in WO92/15686. Briefly, the sample to be tested is diluted in 50 mM Tris (pH 7.5), 0.1% BSA and 100 µl is incubated with 100 µl of FVII deficient plasma and 200 µl of thromboplastin C containing 10 mM $Ca^{++}$. Clotting times are measured and compared to a standard curve using a pool of citrated normal human plasma in serial dilution.

Method of Measuring the Anticoagulant Activity

The anticoagulant activity of an inactive FVII or FVIIa conjugate can be measured using the one-stage clotting assay described above (Method of measuring the clotting activity) where the inactive conjugate competes with wild-type FVII for a limited amount of relipidated tissue factor. The assay is performed essentially as described in WO 92/15686, example III, which is hereby incorporated as reference. The ability of the inactive conjugate to prolong the clotting time of wild-type FVII is recorded and taken as a measure of anticoagulant activity.

EXAMPLES

Example 1

The X-ray structure of hFVIIa in complex with soluble tissue factor by Banner et. al., J Mol Biol, 1996; 285:2089 is used for this example. It is noted that the numbering of residues in the reference does not follow the sequence. Here we have used the sequential numbering according to SEQ ID NO:1. The gamma-carboxy glutamic acids at positions 6, 7, 14, 16, 19, 20, 25, 26, 29 and 35 are all here named GLU (three letter abbreviation) or E (one letter abbreviation). Residues 143-152 are not present in the structure.

Surface Exposure

Performing fractional ASA calculations on FVII fragments alone combined with the definition of accessibilities of non standard and/or missing residues described in the methods resulted in the following residues having more than 25% of their side chain exposed to the surface: A1, N2, A3, F4, L5, E6, E7, L8, R9, P10, S12, L13, E14, E16, K18, E19, E20, Q21, S23, F24, E25, E26, R28, E29, F31, K32, D33, A34, E35, R36, K38, L39, W41, I42, S43, S45, G47, D48, Q49, A51, S52, S53, Q56, G58, S60, K62, D63, Q64, L65, Q66, S67, I69, F71, L73, P74, A75, E77, G78, R79, E82, T83, H84, K85, D86, D87, Q88, L89, I90, V92, N93, E94, G97, E99, S103, D104, H105, T106, G107, T108, K109, S111, R113, E116, G117, S119, L120, L121, A122, D123, G124, V125, S126, T128, P129, T130, V131, E132, I140, L141, E142, K143, R144, N145, A146, S147, K148, P149, Q150, G151, R152, G155, K157, V158, P160, K161, E163, L171, N173, G174, A175, N184, T185, I186, H193, K197, K199, N200, R202, N203, I205, S214, E215, H216, D217, G218, D219, S222, R224, S232, T233, V235, P236, G237, T238, T239, N240, H249, Q250, P251, V253, T255, D256, E265, R266, T267, E270, R271, F275, V276, R277, F278, L280, L287, L288, D289, R290, G291, A292, T293, L295, E296, N301, M306, T307, Q308, D309, L311, Q312, Q313, R315, K316, V317, G318, D319, S320, P321, N322, T324, E325, Y326, Y332, S333, D334, S336, K337, K341, G342, H351, R353, G354, Q366, G367, T370, V371, G372, R379, E385, Q388, K389, R392, S393, E394, P395, R396, P397, G398, V399, L400, L401, R402, P404 and P406.

The following residues had more than 50% of their side chain exposed to the surface: A1, A3, F4, L5, E6, E7, L8, R9, P10, E14, E16, K18, E19, E20, Q21, S23, E25, E26, E29, K32, A34, E35, R36, K38, L39, I42, S43, G47, D48, A51, S52, S53, Q56, G58, S60, K62, L65, Q66, S67, I69, F71, L73, P74, A75, E77, G78, R79, E82, H84, K85, D86, D87, Q88, L89, I90, V92, N93, E94, G97, T106, G107, T108, K109, S111, E116, S119, L121, A122, D123, G124, V131, E132, L141, E142, K143, R144, N145, A146, S147, K148, P149, Q150, G151, R152, G155, K157, P160, N173, G174, A175, K197, K199, N200, R202, S214, E215, H216, G218, R224, V235, P236, G237, T238, H249, Q250, V253, D256, T267, F275, R277, F278, L288, D289, R290, G291, A292, T293, L295, N301, M306, Q308, D309, L311, Q312, Q313, R315, K316, G318, D319, N322, E325, D334, K341, G354, G367, V371, E385, K389, R392, E394, R396, P397, G398, R402, P404 and P406.

Tissue Factor Binding Site

Performing ASA calculations the following residues in human FVII change their ASA in the complex. These residues were defined as constituting the receptor binding site: L13, K18, F31, E35, R36, L39, F40, I42, S43, S60, K62, D63, Q64, L65, I69, C70, F71, C72, L73, P74, F76, E77, G78, R79, E82, K85, Q88, I90, V92, N93, E94, R271, A274, F275, V276, R277, F278, R304, L305, M306, T307, Q308, D309, Q312, Q313, E325 and R379.

Active Site Region

The active site region is defined as any residue having at least one atom within a distance of 10 Å from any atom in the catalytic triad (residues H193, D242, S344): I153, Q167, V168, L169, L170, L171, Q176, L177, C178, G179, G180, T181, V188, V189, S190, A191, A192, H193, C194, F195, D196, K197, I198, W201, V228, I229, I230, P231, S232, T233, Y234, V235, P236, G237, T238, T239, N240, H241, D242, I243, A244, L245, L246, V281, S282, G283, W284, G285, Q286, T293, T324, E325, Y326, M327, F328, D338, S339, C340, K341, G342, D343, S344, G345, G346, P347, H348, L358, T359, G360, I361, V362, S363, W364, G365, C368, V376, Y377, T378, R379, V380, Q382, Y383, W386, L387, L400 and F405.

The Ridge of the Active Site Binding Cleft

The ridge of the active site binding cleft region was defined by visual inspection of the FVIIa structure 1FAK.pdb as: N173, A175, K199, N200, N203, D289, R290, G291, A292, P321 and T370.

Example 2

Design of an Expression Cassette for Expression of Human Blood Coagulation Factor VII in Mammalian Cells The DNA sequence shown in SEQ ID NO:2, encompassing the short form of the full length cDNA encoding human blood coagulation factor VII with its native short signal peptide (Hagen et al., 1986. PNAS 83:2412), was synthesized in order to facilitate high expression in mammalian cells. First the ATG start codon context was modified according to the Kozak consensus sequence (Kozak, M. *J Mol Biol* 1987 Aug. 20; 196(4):947-50), so that there is a perfect match to the consensus sequence upstream of the ATG start codon. Secondly the open reading frame of the native human blood coagulation factor cDNA was modified by making a bias in the codon usage towards the codons frequently used in highly expressed human genes. Further, two translational stop codons was inserted at the end of the open reading frame in order to facilitate efficient translational stop. The fully synthetic and expression optimized human FVII gene was assembled from 70-mer DNA oligonucleotides and finally amplified using end primers inserting BamHI and HindIII sites at the 5' and 3' ends respectively using standard PCR techniques, which resulted in the following sequence (SEQ ID NO:4):

```
ggatcccgccaccatggtcagccaggccctccgcctcctgtgcctgctcc
tggggctgcagggctgcctggctgccgtcttcgtcacccaggaggaagcc
catggcgtcctgcatcgccggcgccgggccaatgcctttctggaagagct
ccgccctggctccctggaacgcgaatgcaaagaggaacagtgcagctttg
aggaagcccgggagattttcaaagacgctgagcggaccaaactgttttgg
attagctatagcgatggcgatcagtgcgcctccagcccttgccagaacgg
gggctcctgcaaagaccagctgcagagctatatctgcttctgcctgcctg
cctttgaggggcgcaattgcgaaacccataaggatgaccagctgatttgc
gtcaacgaaaacggggggctgcgagcagtactgcagcgatcacacgggcac
gaagcggagctgccgctgccacgaaggctatagcctcctggctgacgggg
tgtcctgcacgcccacggtggaataccct tgcgggaagattcccat tcta
gaaaagcggaacgctagcaaacccagggccggatcgtcggcgggaaggt
ctgccctaaggggggagtgccctggcaggtcctgctcctggtcaacgggg
cccagctgtgcggcgggaccctcatcaataccatttgggtcgtgtccgcc
```

-continued
```
gctcactgcttcgataagattaagaattggcggaacctcatcgctgtgct
cggcgaacacgatctgtccgagcatgacggggacgaacagtcccgccggg
tggctcaggtcatcattccctccacctatgtgcctggcacgaccaatcac
gatatcgctctgctccgcctccaccagcccgtcgtgctcaccgatcacgt
cgtgcctctgtgcctgcctgagcggacctttagcgaacgcacgctggctt
tcgtccgctttagcctcgtgtccggctggggccagctgctcgaccggggc
gctaccgctctcgagctgatggtgctcaacgtccccggctgatgaccca
ggactgcctgcagcagtcccgcaaagtgggggactcccccaatatcacgg
agtatatgttttgcgctggctatagcgatggctccaaggatagctgcaag
ggggactccggcgggccccatgccacgcactatcgcgggacctggtacct
caccgggatcgtcagctggggccagggctgcgccacggtggggcactttg
gcgtctacacgcgcgtcagccagtacattgagtggctgcagaagctcatg
cggagcgaacccggcccggggtgctcctgcgggccctttcccttgata
aaagctt
```

A vector for the cloning of the generated PCR product encompassing the expression cassette for native human blood coagulation factor VII was prepared by cloning the intron from pCINeo (Promega). The synthetic intron from pCI-Neo was amplified using standard PCR conditions as described above and the primers:

```
CBProFpr174:
5'- AGCTGGCTAGCCACTGGGCAGGTAAGTATCA -3'
and

CBProFpr175:
5'- TGGCGGGATCCTTAAGAGCTGTAATTGAACT -3'
``` resulting in a 332 bp PCR fragment. The fragment was cut with NheI and BamHI before cloning into pcDNA3.1/HygR (obtained from In Vitro Gen) resulting in PF#34.

The expression cassette for native human blood coagulation factor VII was cloned between the BamHI and HindIII sites of PF#34, resulting in plasmid PF#226.

Example 3

Construction of Expression Cassettes Encoding Variant Forts of Human Blood Coagulation Factor VII that are Having an Additional In Vivo Glycosylation Site.

Sequence overhang extension (SOE) PCR was used for generating constructs having variant human blood coagulation factor open reading frames with substituted codons. In the SOE-PCR both the N-terminal part and the C-terminal part of the FVII open reading frame was first amplified in individual primary PCRs.

For example, in order to change the codons for R315 and V317 to the codons for N315 and T317 the following primers were used pair vice for the primary PCR's:

```
CBProFpr216:  5'-CTTAAGGATCCCGCCACCATGGTCAGCCAG-3'
and

CBProFpr229:  5'-GGAGTCCCCGGTTTTGTTGGACTGCTGC-3',
and

CBProFpr221:  5'-ACTTAAGCTTTTATCAAGGGA-3'
and

CBProFpr228:  5'-GCAGCAGTCCAACAAAACCGGGGACTCC-3'.
```

The primary PCR products were then combined and the terminal primers (CBProFpr216 and CBProFpr221) added resulting in the secondary full-length product encoding the desired R315N+V317T FVII variant. The secondary PCR product was trimmed with BamHI and HindIII before cloning into the vector PF#34 between the BamHI and HindIII sites resulting in PF#249.

Furthermore, in cases where the introduced mutation(s) were sufficiently close to a unique restriction endo-nuclease site in the expression plasmid variant genes were constructed using construction procedure encompassing a single PCR step and a subsequent cloning. For instance, the substitution K143N+N145T was introduced by use of the PCR primers:

```
CBProFpr226:  5'-CATTCTAGAAAACCGGACCGCTAGCAAACC-3'
and

CBProFpr221:  5'-ACTTAAGCTTTTATCAAGGGA-3'
``` in a single PCR reaction.

The PCR product was subsequently cloned using the restriction endo-nuclease sites XbaI and HindIII.

Using the above strategy, the following glycosylation conjugates were prepared and their amidolytic activities were tested as described in the section entitled Method of measuring low levels of catalytic activity. Furthermore, some of the conjugates were subjected to the one-stage clotting assay described in the section entitled Method of measuring the clotting activity. The obtained results are compiled in the following table.

| Glycosylation Conjugate | Amidolytic activity | Clotting activity |
|---|---|---|
| T106N | + | + |
| K143N + N145T | + | nd |
| V253N | + | nd |
| R290N + A292T | − | nd |
| G291N | − | nd |
| R315N + V317T | + | + |
| K143N + N145T + R315N + V317T | + | nd |

+: Activity measurable;
−: Activity not measurable;
nd: not determined

Example 4

Improvement of Glycosylation Site Utility by Introduction of Another Proximal (N-Terminally Located) Glycosylation Site.

In order to prevent autolysis of wild type human FVII a glycosylation site was introduced at position 315 by making the substitutions: R315N and V317T as described above, resulting in PF#249.

Upon transfection of CHO K1 cells, using Lipofactamine 2000, low transient expression levels were obtained. Assaying the twenty-four hour transient supernatant by the amidiolytic assay, COASET® FVII, indicated that the variant was active. After selection using 400 µg/ml Hygromycin B a pool of stable clones was obtained. This pool expresses the R315N+V317T variant at approximately 0.2 µg/ml allowing for Western blotting analysis for determination of the degree of usage of the introduced glycosylation site. A twenty-four hour supernatant from the stable pool was assayed by Western blotting and revealed partial usage of the introduced glycosylation site at position 315, approximately one-half of the fully processed secreted protein is glycosylated. However, if the native glycosylation site at position 145 is moved to position 143, by making the substitutions K143N+N145T, the introduced glycosylation site at position 315 is completely glycosylated as judged by Western blotting.

Example 5

Expression of FVII in HEK 293 Cells

The cell line HEK 293 (ATCC# CRL-1573) was seeded at 20% confluence in T-25 flasks using DMEM, high glucose 10% heat inactivated FCS (Gibco/BRL Cat# 10091), 5 µg/ml phylloquinone and allowed to grow until confluent. The confluent mono cell layer was transfected with 1, 2, 5, 10 and 20 µg of the plasmid p226 described above using the Lipofectamine 2000 transfection agent (Life technologies) according to the manufactures instructions. After 24 hours post transfection a medium sample was drawn. The FVII concentration in the 24 hour transient expression experiments was on average 0.15 µg/ml.

Subsequently, selection medium containing 100 µg/ml Hygromycin B was administered to the cells. After three weeks of selection, with renewal of the medium every 3rd or 4th day, the Hygromycin resistant cells were confluent in the flasks transfected with 1 µg of plasmid DNA and 2 µg of plasmid DNA. The cells from each of the five flasks were harvested and pooled. The resulting stable pool of transfectants expressing native human blood coagulation factor VII was frozen in liquid nitrogen according to standard procedures.

Example 6

Generation of HEK293 Cells Stably Expressing FVII.

A vial of HEK293 PF#226 transfectant pool was thawed and the cells seeded in a 75 cm² tissue flask containing 15 ml of DMEM high glucose, 10% FCS, phylloquinone (5 µg/ml), 100 U/l penicillin, 100 µg/l streptomycin, which was used for all subsequent experiments, and grown for 24 hours. The cells were harvested, diluted and plated in 96 well micro titer plates at a cell density of ½ cell/well. After 12 days colonies of about 20-100 cells were present in the wells and those wells containing only one colony were labeled. After a further two days of growth an additional 100 µl medium was added to all wells. Two days later the media in all wells containing only one colony were changed. The first colonies were transferred to 25 cm² tissue flasks culturing after 3 days and depending on the level of confluency the colonies were transferred to 25 cm² tissue flasks culturing the next 11 days. When confluent in T-25 tissue flasks the medium was changed and clones allowed to secrete FVII into the growth medium for 24 hours, after which the supernatants were harvested and assayed for the presence of factor VII using the COASET FVII amidolytic assay. One clone, C18, was found to express 29 µg/ml FVII.

Example 7

Expression of FVII Glycosylation Variants with No Amidolytic Activity Capable of Inhibiting the Function of FVIIa The expression plasmids for expression of the active site ridge mutants R290N+A292T and G291N were constructed essentially as described in example 3.

Using the amidiolytic assay COASET® FVII (see above) the ability of the two FVII glycosylation variants, R290N+A292T and G291N, to inhibit the activity of rFVIIa was evaluated. The plasmids PF#250 encoding R290N+A292T and the plasmid PF#294 encoding G291N were transfected into near confluent serum grown HEK293 cells using Lipofectamin 2000. The transfected cells were incubated at 37° C. with 5% $CO_2$ for three hours post transfection before the medium was changed to serum free medium (DMEM, ITS-A, ExCyte, Phylloquinone, P/S). Forty hours post transfection the conditioned medium was harvested and cleared by centrifugation for analysis.

A standard curve was made from rFVIIa: 0.0125 ng, 0.025 ng, 0.05 ng, 0.075 ng and 0.1 ng. Fifty µl aliquots of undiluted, 2-fold diluted, 5 fold diluted, 10-fold diluted and 50-fold diluted condition medium from either of the two inactive glycosylation variants R290N+A292T and G291N or conditioned medium from a mock transfection were spiked with 0.025 ng rFVIIa. When assayed in the COASET FVII assay 0.025 ng of FVIIa corresponded to a signal of $OD_{405}$=0.35 (first run) and $OD_{405}$=0.26 (second run).

The obtained results are compiled in the following table:

| Glycosylation Conjugate | Dilution | $OD_{405}$ | |
|---|---|---|---|
| Standard | | 0.35 | 0.26 |
| Mock | 50 | 0.38 | 0.19 |
| | 25 | 0.31 | 0.16 |
| | 10 | 0.21 | 0.15 |
| | 5 | 0.22 | 0.14 |
| | 1 | 0.08 | 0.07 |
| R290N + A292T | 50 | 0.23 | — |
| | 25 | 0.12 | — |
| | 10 | 0.07 | — |
| | 5 | 0.04 | — |
| | 1 | 0.04 | — |
| G291N | 50 | — | 0.16 |
| | 25 | — | 0.08 |
| | 10 | — | 0.06 |
| | 5 | — | 0.05 |
| | 1 | — | 0.04 |

As it appears from the above data the glycosylation conjugates G291N and R290N+A292T inhibit the function rFVIIa.

Example 8

Purification of FVII and Subsequent Activation

Purification of wild-type Factor VII and conjugates thereof was performed at 4° C. The supernatant from cells expressing the conjugate (or wild-type FVII) was sterile filtered (0.22 µm) and diluted 2 fold in cold milliQ water. EDTA was added to 5 mM, pH adjusted to 8.6 and conductivity was below 10 mS/cm. The sample was applied onto a Q-sepharose Fast Flow resin (Pharmacia) equilibrated at 4° C. in 10 mM Tris pH 8.6. After application of the sample the column washed in 10 mM Tris (pH 8.6), 150 mM NaCl, until the absorption at 280 nm reached baseline levels. Then the column was equilibrated in 10 mM Tris (pH 8.6), 100 mM NaCl. Bound conjugate (or wild-type FVII) was eluted with 10 mM Tris (pH 8.6), 100 mM NaCl, 5 mM $CaCl_2$. Fractions enriched in conjugate (or wild-type FVII) was pooled and concentrated by dialysis or by using Vivaspin concentration units (Vivascience).

Auto-activation of the conjugate (or wild-type FVII) was obtained by concentration and incubation of the eluted protein in 10 mM Tris (pH 7.8-8.6), 100 mM NaCl, 5 mM $CaCl_2$.

Alternatively, the conjugate (or wild-type FVII) was activated at 37° C. by Factor Xa coupled to CNBr-activated sepharose in 10 mM Tris (pH 7.4-8.0) 100 mM NaCl, 5 mM $CaCl_2$.

The conjugate (or wild-type FVIIa) was buffer-exchanged into a solution containing 10 mM $CaCl_2$, 50 mM NaCl, 3% mannitol, 0.05% Tween80, buffered at pH 5.6 and sterilfiltered before storage at −80° C.

Example 9

N-Terminal Pegylation of FVII

Factor VII was conjugated with methoxy polyethylene glycol (mPEG) having a molecular weight of about 5 kDa using M-PEG-CHO (M-ALD-5000, obtained from Shearwater) in a buffer containing 10 mM sodium citrate, 20 mM $CaCl_2$, 100 mM NaCl, pH 5.5. M-PEG-CHO was present in 50-100-fold molar excess, and the protein concentration was 0.2-0.5 mg/ml. The reaction was carried out in 300-1500 µl batches at room temperature for 1 hour with agitation, and $NaBH_3CN$ was added to 500-1000 fold excess and incubation continued over night with agitation at room temperature.

PEGylated FVII was buffer exchanged to buffer A (10 mM Tris pH 7.6) and applied at 4° C. on a mono Q column (Pharmacia) equilibrated in buffer A. Bound protein was eluted in a gradient from 0-100% B (10 mM Tris (pH 7.6), 500 mM NaCl) over 40 column volumes.

Example 10

Pharmakokinetic Studies in Rats

Both wild-type FVII and the conjugates of the invention are formulated in 1.3 mg/ml glycyl-glycin buffer pH 5.5 containing 1.5 mg/ml $CaCl_2$, 30 mg/ml mannitol, 0.1 mg/ml polysorbat 80 and 3 mg/ml NaCl. For determination of in vivo half-life each of the preparations are administered to Sprague-Dawley rats as one intra venous bolus injection. The injections are given slowly over about 10 seconds to reduce potential risk of heart failure due to high $C^{2+}$ concentration. Blood samples are drawn from each of the nine anaesthetized rats at suitable intervals, e.g., 1 minute, 15 minutes, 30 minutes, 45 minutes and 1 hour after injection. The blood samples are collected in 1 ml tubes containing 50 µl Citrate-phosphate-dextrose solution with adenine (Sigma #C4431) in order to prevent coagulation. Immediately after collection the samples are stored at about 0° C. until centrifugation and subsequent collection of the citrate plasma supernatants for assay. Samples are assayed by the one-stage clotting assay as described in the section Method of measuring the clotting activity and the half-lives are then calculated.

While the foregoing invention has been described in some detail for purposes of clarity and understanding, it will be clear to one skilled in the art from a reading of this disclosure that various changes in form and detail can be made without departing from the true scope of the invention. For example, all the techniques, methods, compositions, apparatus and systems described above can be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A nucleic acid comprising a nucleotide sequence which encodes a polypeptide comprising an amino acid sequence which (a) differs from the hFVII or hFVIIa sequence SEQ ID NO:1 in 1-15 amino acid residues and (b) comprises an introduced in vivo N-glycosylation site relative to SEQ ID NO:1, wherein the introduced in vivo N-glycosylation site comprises the substitution V253N.

2. The nucleic acid of claim 1, wherein the encoded polypeptide further comprises at least one additional introduced in vivo N-glycosylation site.

3. The nucleic acid of claim 2, wherein the at least one additional introduced in vivo N-glycosylation site comprises the substitution I205S/T.

4. The nucleic acid of claim 2, wherein the at least one additional introduced in vivo N-glycosylation site comprises the substitutions R315N+V317S/T.

5. The nucleic acid of claim 2, wherein the encoded polypeptide comprises two additional introduced in vivo N-glycosylation sites comprising the substitutions I205S/T and T267N.

6. The nucleic acid of claim 2, wherein the additional introduced in vivo N-glycosylation site is introduced in a position relative to SEQ ID NO:1 occupied by an amino acid residue with more than 25% of its side chain exposed to the solvent.

7. The nucleic acid of claim 2, wherein the additional introduced in vivo N-glycosylation site comprises an amino acid substitution in a position selected from the group consisting of 28-48, 139-147, 286-294, 311-319, 338-345 and 388-406 relative to SEQ ID NO:1.

8. An expression vector comprising the nucleic acid of claim 1.

9. A host cell comprising the nucleic acid of claim 1.

10. The host cell of claim 9, wherein the host cell is a eukaryotic host cell.

* * * * *

SEQUENCE LISTING

<160> NUMBER OF SEQ ID NOS: 19

<210> SEQ ID NO 1
<211> LENGTH: 406
<212> TYPE: PRT
<213> ORGANISM: Homo sapiens
<220> FEATURE:
<221> NAME/KEY: MOD_RES
<222> LOCATION: (6)..(7)
<223> OTHER INFORMATION: Gamma carboxyglutamic acid or glutamic acid
<220> FEATURE:
<221> NAME/KEY: MOD_RES
<222> LOCATION: (14)
<223> OTHER INFORMATION: Gamma carboxyglutamic acid or glutamic acid
<220> FEATURE:
<221> NAME/KEY: MOD_RES
<222> LOCATION: (16)
<223> OTHER INFORMATION: Gamma carboxyglutamic acid or glutamic acid
<220> FEATURE:
<221> NAME/KEY: MOD_RES
<222> LOCATION: (19)..(20)
<223> OTHER INFORMATION: Gamma carboxyglutamic acid or glutamic acid
<220> FEATURE:
<221> NAME/KEY: MOD_RES
<222> LOCATION: (25)..(26)
<223> OTHER INFORMATION: Gamma carboxyglutamic acid or glutamic acid
<220> FEATURE:
<221> NAME/KEY: MOD_RES
<222> LOCATION: (29)
<223> OTHER INFORMATION: Gamma carboxyglutamic acid or glutamic acid
<220> FEATURE:
<221> NAME/KEY: MOD_RES
<222> LOCATION: (35)
<223> OTHER INFORMATION: Gamma carboxyglutamic acid or glutamic acid

<400> SEQUENCE: 1

```
Ala Asn Ala Phe Leu Xaa Xaa Leu Arg Pro Gly Ser Leu Xaa Arg Xaa
 1               5                  10                  15

Cys Lys Xaa Xaa Gln Cys Ser Phe Xaa Xaa Ala Arg Xaa Ile Phe Lys
            20                  25                  30

Asp Ala Xaa Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
    130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205
```

-continued

```
Gly Glu His Asp Leu Ser Glu His Asp Gly Asp Gln Ser Arg Arg
    210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
        275                 280                 285

Asp Arg Gly Ala Thr Ala Leu Glu Leu Met Val Leu Asn Val Pro Arg
    290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
            340                 345                 350

Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
    370                 375                 380

Glu Trp Leu Gln Lys Leu Met Arg Ser Glu Pro Arg Pro Gly Val Leu
385                 390                 395                 400

Leu Arg Ala Pro Phe Pro
                405

<210> SEQ ID NO 2
<211> LENGTH: 1338
<212> TYPE: DNA
<213> ORGANISM: Homo sapiens
<220> FEATURE:
<221> NAME/KEY: CDS
<222> LOCATION: (115)..(1332)

<400> SEQUENCE: 2
atggtcagcc aggccctccg cctcctgtgc ctgctcctgg ggctgcaggg ctgcctggct    60
gccgtcttcg tcacccagga ggaagcccat ggcgtcctgc atcgccggcg ccgg gcc     117
                                                              Ala
                                                              1 aat gcc ttt ctg gaa gag ctc cgc cct ggc tcc ctg gaa cgc gaa tgc     165
Asn Ala Phe Leu Glu Glu Leu Arg Pro Gly Ser Leu Glu Arg Glu Cys
        5                   10                  15 aaa gag gaa cag tgc agc ttt gag gaa gcc cgg gag att ttc aaa gac    213
Lys Glu Glu Gln Cys Ser Phe Glu Glu Ala Arg Glu Ile Phe Lys Asp
    20                  25                  30 gct gag cgg acc aaa ctg ttt tgg att agc tat agc gat ggc gat cag    261
Ala Glu Arg Thr Lys Leu Phe Trp Ile Ser Tyr Ser Asp Gly Asp Gln
35                  40                  45 tgc gcc tcc agc cct tgc cag aac ggg ggc tcc tgc aaa gac cag ctg    309
Cys Ala Ser Ser Pro Cys Gln Asn Gly Gly Ser Cys Lys Asp Gln Leu
 50                  55                  60                  65 cag agc tat atc tgc ttc tgc ctg cct gcc ttt gag ggg cgc aat tgc    357
Gln Ser Tyr Ile Cys Phe Cys Leu Pro Ala Phe Glu Gly Arg Asn Cys
                70                  75                  80 gaa acc cat aag gat gac cag ctg att tgc gtc aac gaa aac ggg ggc    405
Glu Thr His Lys Asp Asp Gln Leu Ile Cys Val Asn Glu Asn Gly Gly
            85                  90                  95
```

```
tgc gag cag tac tgc agc gat cac acg ggc acg aag cgg agc tgc cgc       453
Cys Glu Gln Tyr Cys Ser Asp His Thr Gly Thr Lys Arg Ser Cys Arg
        100                 105                 110 tgc cac gaa ggc tat agc ctc ctg gct gac ggg gtg tcc tgc acg ccc       501
Cys His Glu Gly Tyr Ser Leu Leu Ala Asp Gly Val Ser Cys Thr Pro
    115                 120                 125 acg gtg gaa tac cct tgc ggg aag att ccc att cta gaa aag cgg aac       549
Thr Val Glu Tyr Pro Cys Gly Lys Ile Pro Ile Leu Glu Lys Arg Asn
130                 135                 140                 145 gct agc aaa ccc cag ggc cgg atc gtc ggc ggg aag gtc tgc cct aag       597
Ala Ser Lys Pro Gln Gly Arg Ile Val Gly Gly Lys Val Cys Pro Lys
                150                 155                 160 ggg gag tgc ccc tgg cag gtc ctg ctc ctg gtc aac ggg gcc cag ctg       645
Gly Glu Cys Pro Trp Gln Val Leu Leu Leu Val Asn Gly Ala Gln Leu
            165                 170                 175 tgc ggg ggg acc ctc atc aat acc att tgg gtc gtg tcc gcc gct cac       693
Cys Gly Gly Thr Leu Ile Asn Thr Ile Trp Val Val Ser Ala Ala His
        180                 185                 190 tgc ttc gat aag att aag aat tgg cgg aac ctc atc gct gtg ctc ggc       741
Cys Phe Asp Lys Ile Lys Asn Trp Arg Asn Leu Ile Ala Val Leu Gly
    195                 200                 205 gaa cac gat ctg tcc gag cat gac ggg gac gaa cag tcc cgc cgg gtg       789
Glu His Asp Leu Ser Glu His Asp Gly Asp Glu Gln Ser Arg Arg Val
210                 215                 220                 225 gct cag gtc atc att ccc tcc acc tat gtg cct ggc acg acc aat cac       837
Ala Gln Val Ile Ile Pro Ser Thr Tyr Val Pro Gly Thr Thr Asn His
                230                 235                 240 gat atc gct ctg ctc cgc ctc cac cag ccc gtc gtg ctc acc gat cac       885
Asp Ile Ala Leu Leu Arg Leu His Gln Pro Val Val Leu Thr Asp His
            245                 250                 255 gtc gtg cct ctg tgc ctg cct gag cgg acc ttt agc gaa cgc acg ctg       933
Val Val Pro Leu Cys Leu Pro Glu Arg Thr Phe Ser Glu Arg Thr Leu
        260                 265                 270 gct ttc gtc cgc ttt agc ctc gtg tcc ggc tgg ggc cag ctg ctc gac       981
Ala Phe Val Arg Phe Ser Leu Val Ser Gly Trp Gly Gln Leu Leu Asp
    275                 280                 285 cgg ggc gct acc gct ctc gag ctg atg gtg ctc aac gtc ccc cgg ctg      1029
Arg Gly Ala Thr Ala Leu Glu Leu Met Val Leu Asn Val Pro Arg Leu
290                 295                 300                 305 atg acc cag gac tgc ctg cag cag tcc cgc aaa gtg ggg gac tcc ccc      1077
Met Thr Gln Asp Cys Leu Gln Gln Ser Arg Lys Val Gly Asp Ser Pro
                310                 315                 320 aat atc acg gag tat atg ttt tgc gct ggc tat agc gat ggc tcc aag      1125
Asn Ile Thr Glu Tyr Met Phe Cys Ala Gly Tyr Ser Asp Gly Ser Lys
            325                 330                 335 gat agc tgc aag ggg gac tcc ggc ggg ccc cat gcc acg cac tat cgc      1173
Asp Ser Cys Lys Gly Asp Ser Gly Gly Pro His Ala Thr His Tyr Arg
        340                 345                 350 ggg acc tgg tac ctc acc ggg atc gtc agc tgg ggc cag ggc tgc gcc      1221
Gly Thr Trp Tyr Leu Thr Gly Ile Val Ser Trp Gly Gln Gly Cys Ala
    355                 360                 365 acg gtg ggg cac ttt ggc gtc tac acg cgc gtc agc cag tac att gag      1269
Thr Val Gly His Phe Gly Val Tyr Thr Arg Val Ser Gln Tyr Ile Glu
370                 375                 380                 385 tgg ctg cag aag ctc atg cgg agc gaa ccc cgg ccc ggg gtg ctc ctg      1317
Trp Leu Gln Lys Leu Met Arg Ser Glu Pro Arg Pro Gly Val Leu Leu
                390                 395                 400 cgg gcc cct ttc cct tgataa                                           1338
Arg Ala Pro Phe Pro
```

405

<210> SEQ ID NO 3
<211> LENGTH: 406
<212> TYPE: PRT
<213> ORGANISM: Homo sapiens

<400> SEQUENCE: 3

| | | | | | | | | | | | | | |
|---|---|---|---|---|---|---|---|---|---|---|---|---|---|
| Ala | Asn | Ala | Phe | Leu | Glu | Glu | Leu | Arg | Pro | Gly | Ser | Leu | Glu | Arg | Glu |
| 1 | | | | 5 | | | | | 10 | | | | | 15 | |
| Cys | Lys | Glu | Glu | Gln | Cys | Ser | Phe | Glu | Glu | Ala | Arg | Glu | Ile | Phe | Lys |
| | | | 20 | | | | | 25 | | | | | 30 | | |
| Asp | Ala | Glu | Arg | Thr | Lys | Leu | Phe | Trp | Ile | Ser | Tyr | Ser | Asp | Gly | Asp |
| | | 35 | | | | | 40 | | | | | 45 | | | |
| Gln | Cys | Ala | Ser | Ser | Pro | Cys | Gln | Asn | Gly | Gly | Ser | Cys | Lys | Asp | Gln |
| | 50 | | | | | 55 | | | | | 60 | | | | |
| Leu | Gln | Ser | Tyr | Ile | Cys | Phe | Cys | Leu | Pro | Ala | Phe | Glu | Gly | Arg | Asn |
| 65 | | | | | 70 | | | | | 75 | | | | | 80 |
| Cys | Glu | Thr | His | Lys | Asp | Asp | Gln | Leu | Ile | Cys | Val | Asn | Glu | Asn | Gly |
| | | | | 85 | | | | | 90 | | | | | 95 | |
| Gly | Cys | Glu | Gln | Tyr | Cys | Ser | Asp | His | Thr | Gly | Thr | Lys | Arg | Ser | Cys |
| | | | 100 | | | | | 105 | | | | | 110 | | |
| Arg | Cys | His | Glu | Gly | Tyr | Ser | Leu | Leu | Ala | Asp | Gly | Val | Ser | Cys | Thr |
| | | 115 | | | | | 120 | | | | | 125 | | | |
| Pro | Thr | Val | Glu | Tyr | Pro | Cys | Gly | Lys | Ile | Pro | Ile | Leu | Glu | Lys | Arg |
| | 130 | | | | | 135 | | | | | 140 | | | | |
| Asn | Ala | Ser | Lys | Pro | Gln | Gly | Arg | Ile | Val | Gly | Gly | Lys | Val | Cys | Pro |
| 145 | | | | | 150 | | | | | 155 | | | | | 160 |
| Lys | Gly | Glu | Cys | Pro | Trp | Gln | Val | Leu | Leu | Leu | Val | Asn | Gly | Ala | Gln |
| | | | | 165 | | | | | 170 | | | | | 175 | |
| Leu | Cys | Gly | Gly | Thr | Leu | Ile | Asn | Thr | Ile | Trp | Val | Val | Ser | Ala | Ala |
| | | | 180 | | | | | 185 | | | | | 190 | | |
| His | Cys | Phe | Asp | Lys | Ile | Lys | Asn | Trp | Arg | Asn | Leu | Ile | Ala | Val | Leu |
| | | 195 | | | | | 200 | | | | | 205 | | | |
| Gly | Glu | His | Asp | Leu | Ser | Glu | His | Asp | Gly | Asp | Glu | Gln | Ser | Arg | Arg |
| | 210 | | | | | 215 | | | | | 220 | | | | |
| Val | Ala | Gln | Val | Ile | Ile | Pro | Ser | Thr | Tyr | Val | Pro | Gly | Thr | Thr | Asn |
| 225 | | | | | 230 | | | | | 235 | | | | | 240 |
| His | Asp | Ile | Ala | Leu | Leu | Arg | Leu | His | Gln | Pro | Val | Val | Leu | Thr | Asp |
| | | | | 245 | | | | | 250 | | | | | 255 | |
| His | Val | Val | Pro | Leu | Cys | Leu | Pro | Glu | Arg | Thr | Phe | Ser | Glu | Arg | Thr |
| | | | 260 | | | | | 265 | | | | | 270 | | |
| Leu | Ala | Phe | Val | Arg | Phe | Ser | Leu | Val | Ser | Gly | Trp | Gly | Gln | Leu | Leu |
| | | 275 | | | | | 280 | | | | | 285 | | | |
| Asp | Arg | Gly | Ala | Thr | Ala | Leu | Glu | Leu | Met | Val | Leu | Asn | Val | Pro | Arg |
| | 290 | | | | | 295 | | | | | 300 | | | | |
| Leu | Met | Thr | Gln | Asp | Cys | Leu | Gln | Gln | Ser | Arg | Lys | Val | Gly | Asp | Ser |
| 305 | | | | | 310 | | | | | 315 | | | | | 320 |
| Pro | Asn | Ile | Thr | Glu | Tyr | Met | Phe | Cys | Ala | Gly | Tyr | Ser | Asp | Gly | Ser |
| | | | | 325 | | | | | 330 | | | | | 335 | |
| Lys | Asp | Ser | Cys | Lys | Gly | Asp | Ser | Gly | Gly | Pro | His | Ala | Thr | His | Tyr |
| | | | 340 | | | | | 345 | | | | | 350 | | |
| Arg | Gly | Thr | Trp | Tyr | Leu | Thr | Gly | Ile | Val | Ser | Trp | Gly | Gln | Gly | Cys |
| | | 355 | | | | | 360 | | | | | 365 | | | |

```
Ala Thr Val Gly His Phe Gly Val Tyr Thr Arg Val Ser Gln Tyr Ile
    370                 375                 380

Glu Trp Leu Gln Lys Leu Met Arg Ser Glu Pro Arg Pro Gly Val Leu
385                 390                 395                 400

Leu Arg Ala Pro Phe Pro
                405
```

```
<210> SEQ ID NO 4
<211> LENGTH: 1357
<212> TYPE: DNA
<213> ORGANISM: Artificial Sequence
<220> FEATURE:
<223> OTHER INFORMATION: Description of Artificial Sequence:  Expression
      cassette for expression of FVII in mammalian cells

<400> SEQUENCE: 4
ggatcccgcc accatggtca gccaggccct ccgcctcctg tgcctgctcc tggggctgca      60
gggctgcctg gctgccgtct tcgtcaccca ggaggaagcc catggcgtcc tgcatcgccg     120
gcgccgggcc aatgcctttc tggaagagct ccgccctggc tccctggaac gcgaatgcaa     180
agaggaacag tgcagctttg aggaagcccg ggagattttc aaagacgctg agcggaccaa     240
actgttttgg attagctata gcgatggcga tcagtgcgcc tccagccctt gccagaacgg     300
gggctcctgc aaagaccagc tgcagagcta tatctgcttc tgcctgcctg cctttgaggg     360 cgcaattgc gaaacccata aggatgacca gctgatttgc gtcaacgaaa acggggctg     420 cgagcagtac tgcagcgatc acacgggcac gaagcggagc tgccgctgcc acgaaggcta     480
tagcctcctg gctgacgggg tgtcctgcac gcccacggtg aataccctt gcgggaagat     540 tcccattcta gaaaagcgga acgctagcaa accccagggc cggatcgtcg gcgggaaggt     600
ctgccctaag ggggagtgcc cctggcaggt cctgctcctg gtcaacgggg cccagctgtg     660
cggcgggacc ctcatcaata ccatttgggt cgtgtccgcc gctcactgct tcgataagat     720
taagaattgg cggaacctca tcgctgtgct cggcgaacac gatctgtccg agcatgacgg     780
ggacgaacag tcccgccggg tggctcaggt catcattccc tccacctatg tgcctggcac     840
gaccaatcac gatatcgctc tgctccgcct ccaccagccc gtcgtgctca ccgatcacgt     900
cgtgcctctg tgcctgcctg agcggacctt tagcgaacgc acgctggctt tcgtccgctt     960
tagcctcgtg tccggctggg gccagctgct cgaccggggc gctaccgctc tcgagctgat    1020
ggtgctcaac gtccccggc tgatgaccca ggactgcctg cagcagtccc gcaaagtggg    1080
ggactccccc aatatcacgg agtatatgtt ttgcgctggc tatagcgatg gctccaagga    1140
tagctgcaag ggggactccg gcgggccccca tgccacgcac tatcgcggga cctggtacct    1200
caccgggatc gtcagctggg gccagggctg cgccacggtg gggcactttg gcgtctacac    1260
gcgcgtcagc cagtacattg agtggctgca gaagctcatg cggagcgaac cccggcccgg    1320
ggtgctcctg cgggccccctt tcccttgata aagctt                             1357
```

```
<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence:  Primer
      CBProFpr174

<400> SEQUENCE: 5
agctggctag ccactgggca ggtaagtatc a                                     31
```

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Primer
      CBProFpr175

<400> SEQUENCE: 6
tggcgggatc cttaagagct gtaattgaac t                                    31

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Primer
      CBProFpr216

<400> SEQUENCE: 7
cttaaggatc ccgccaccat ggtcagccag                                      30

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Primer
      CBProFpr229

<400> SEQUENCE: 8
ggagtccccg gttttgttgg actgctgc                                        28

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Primer
      CBProFpr221

<400> SEQUENCE: 9
acttaagctt ttatcaaggg a                                               21

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Primer
      CBProFpr228

<400> SEQUENCE: 10
gcagcagtcc aacaaaaccg gggactcc                                        28

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Primer
      CBProFpr226

<400> SEQUENCE: 11
cattctagaa aaccggaccg ctagcaaacc                                      30

```
<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: synthetic
      peptide tag

<400> SEQUENCE: 12

His His His His His His
 1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: synthetic
      peptide tag

<400> SEQUENCE: 13

Met Lys His His His His His His
 1               5

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: synthetic
      peptide tag

<400> SEQUENCE: 14

Met Lys His His Ala His His Gln His His
 1               5                  10

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: synthetic
      peptide tag

<400> SEQUENCE: 15

Met Lys His Gln His Gln His Gln His Gln His Gln His Gln
 1               5                  10

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: synthetic
      peptide tag

<400> SEQUENCE: 16

Met Lys His Gln His Gln His Gln His Gln His Gln His Gln Gln
 1               5                  10                  15

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: synthetic
      peptide tag

<400> SEQUENCE: 17
```

```
Glu Gln Lys Leu Ile Ser Glu Glu Asp Leu
 1               5                   10

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: synthetic
      peptide tag

<400> SEQUENCE: 18

Asp Tyr Lys Asp Asp Asp Asp Lys
 1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: synthetic
      peptide tag

<400> SEQUENCE: 19

Tyr Pro Tyr Asp Val Pro Asp Tyr Ala
 1               5
```